US005871742A

United States Patent [19]
Saitoh et al.

[11] Patent Number: 5,871,742
[45] Date of Patent: Feb. 16, 1999

[54] **RECOMBINANT AVIPOX VIRUS ENCODING POLYPEPTIDE OF *MYCOPLASMA GALLISEPTICUM*, AND UTILIZED A LIVE VACCINE**

[75] Inventors: Shuji Saitoh; Setsuko Ohkawa, both of Yokohama; Sakiko Saeki; Ikuroh Ohsawa, both of Tokyo; Hirono Funato, Soka; Yoshikazu Iritani, Kyoto; Shigemi Aoyama, Koka-gun; Kiyohito Takahashi, Kurita-gun, all of Japan

[73] Assignees: Nippon Zeon Co., Ltd, Tokyo; Shionogi & Co., Ltd., Osaka, both of Japan

[21] Appl. No.: 525,742
[22] PCT Filed: Mar. 31, 1994
[86] PCT No.: PCT/JP94/00541
 § 371 Date: Sep. 25, 1995
 § 102(e) Date: Sep. 25, 1995
[87] PCT Pub. No.: WO94/23019
 PCT Pub. Date: Oct. 13, 1994

[30] Foreign Application Priority Data

Mar. 31, 1993 [JP] Japan ..................................... 5-074139
Sep. 30, 1993 [JP] Japan ..................................... 5-245625

[51] Int. Cl.⁶ ........................ A61K 39/295; A61K 39/12; C12N 15/31; C07K 7/01
[52] U.S. Cl. ..................................... 424/199.1; 424/264.1; 424/214.1; 424/215.1; 424/190.1; 424/232.1; 424/192.1; 435/69.1; 435/69.3; 435/70.1; 435/320.1; 536/23.4; 536/23.7; 530/350; 530/820; 530/825; 930/200
[58] Field of Search ............................... 424/199.1, 264.1, 424/214.1, 215.1, 190.1, 232.1, 192.1; 435/69.1, 69.3, 70.1, 320.1; 536/23.4, 23.7; 530/350, 820, 825; 930/200

[56] References Cited

U.S. PATENT DOCUMENTS 5,093,258  3/1992  Cohen et al. ....................... 435/235.1
5,196,514  3/1993  Avakian et al. ........................ 530/350

FOREIGN PATENT DOCUMENTS 0 308 220   3/1989   European Pat. Off. .
0345021     5/1989   European Pat. Off. .
0 404 576  12/1990   European Pat. Off. .
1-168279    7/1989   Japan .
2-111795    4/1990   Japan .
9002564     3/1990   WIPO .

OTHER PUBLICATIONS

Avakian et al, "Evaluation of Sodium Dodecyl Sulfate–Polyacrylamide Gel Electrophoresis Purified Proteins of *Mycoplasma gallisepticum* and *M. synoviae* as Antigens in a Dot–Enzyme–Linked Immunosorbent Assay", Avian Diseases, vol. 34, pp. 575–584, 1990.

Molecular and Cellular Biology, vol. 10, No. 2, (1990), Wilson C. et al.: "Abenant membrane insertion of a cytoplasmic tail delection mutant of the hemagglutinin neuraminidase glycoprotein of newcastle disease virus", see pp. 449–457.

WO, A, 9324646 (Nippon Zeon Co., Ltd., Shionogi & Co., Ltd.), Dec. 9, 1993 (Sep. 12,1993) & AU, A, 9340903.

*Primary Examiner*—Marian C. Knode
*Assistant Examiner*—Ali R. Salimi
*Attorney, Agent, or Firm*—Armstrong, Westerman, Hattori, McLeland & Naughton

[57] ABSTRACT

A polypeptide exhibiting the antigenicity of *Mycoplasma gallisepticum*, a fused polypeptide comprising the above polypeptide and, connected to the N-terminus thereof, a signal membrane anchor of a type II outer-membrane polypeptide of a virus that infects birds, or a polypeptide capable of reacting with a mycoplasma-immune serum or a mycoplasma-infected serum and exhibiting a substantially pure antigenecity, respectively having amino acid sequences of about 32 kDa, about 40 kDa, or about 70 kDa. The expression with a recombinant virus of a polypeptide modified to such an extent as to exhibit an antigenicity equivalent to that of any of the above polypeptides. The use of a recombinant virus as a live vaccine.

21 Claims, 18 Drawing Sheets

(RESTRICTION ENZYME MAP OF TM-81)

E: EcoR I, Pv: Pvu II, Sp: Spa I, H: Hind III
Hc: Hinc II, G: Bgl II

E: EcoR I
V: EcoR V
G: Bgl II
Sac: Sac I
X: Xba I
Ss: Ssp I
Sp: Spe I

*MUTAGENETIC SITE OF NUCLEOTIDE

A, Ava II; Alu, Alu I; B, BamH I; Dra,
Dra I; E, EcoR I; ET, EcoT22 I; G, Bgl II;
H, Hind III; Hc, Hinc II; K, Kpn I; Sac,
Sac I; Sm, Sma I; X, Xba I; Xho, Xho I

- TTM1 GENE
- SYNTHETIC PROMOTOR
- FPV-DERIVED DNA
- lacZ GENE
- HN GENE

A, Ava II; Alu, Alu I; B, BamH I; Dra,
Dra I; E, EcoR I; ET, EcoRT22 I; G, Bgl II;
H, Hind III; Hc, Hinc II; K, Kpn I; Sac,
Sac I; Sm, Sma I; X, Xba I; Xho, Xho I

- TTM1 GENE
- SYNTHETIC PROMOTOR
- FPV-DERIVED DNA
- lacZ GENE
- HN GENE

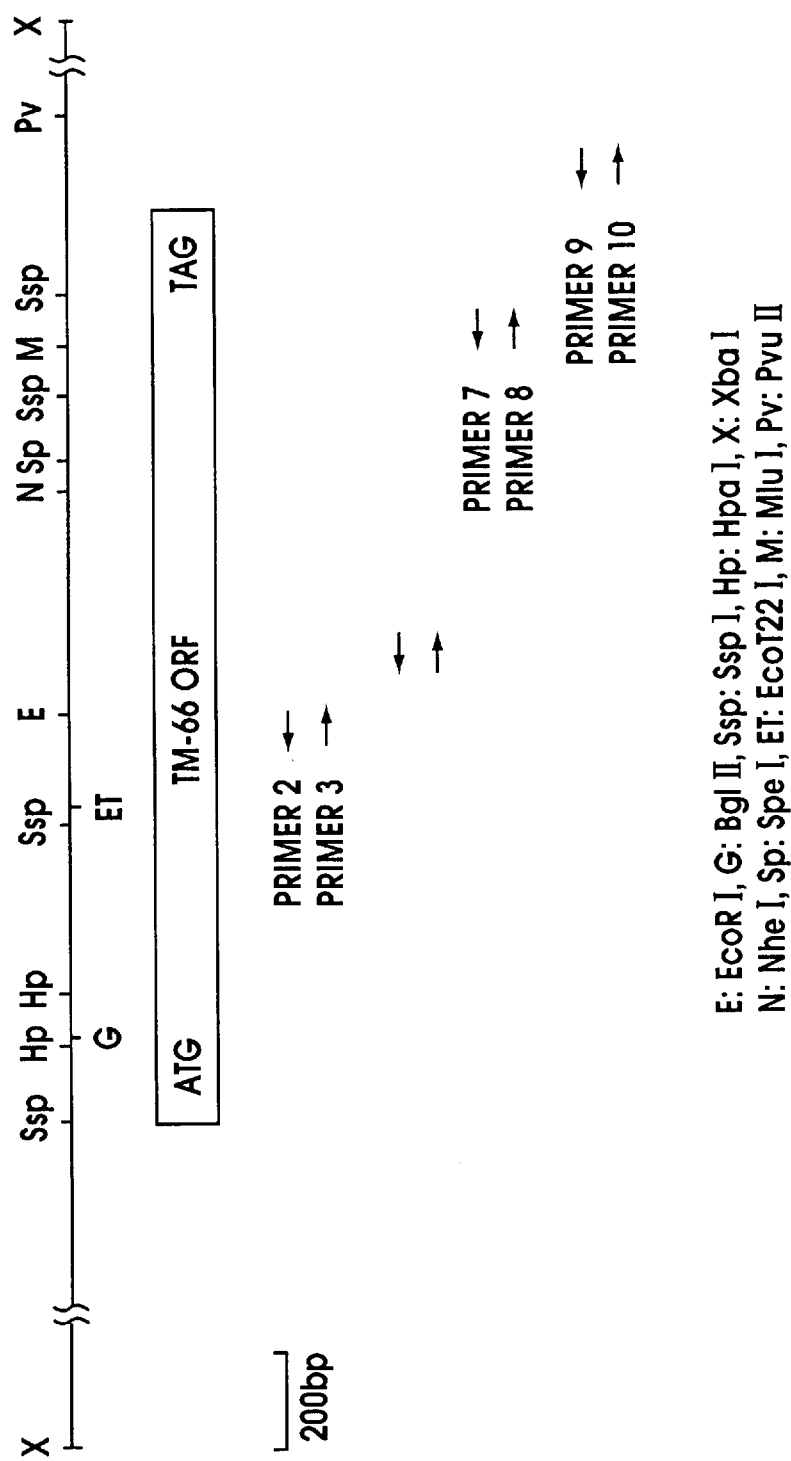

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 2369 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 171..2153

( x i ) SEQUENCE DESCRIPTION: SEQ ID NO:1:

```
GTCTGGGGTT  GGTTTGATCA  GCGAAAATAA  ACCCGATTTA  TTACTTACTG  AACTTTATAT        60

ATTCTTTAGA  TAATAATAGA  CGTGGTGAAC  GTAAGTTATT  GGCTTAACTT  TAAGTGAAAA       120

GAAAAAACAT  TTTAAAGTTT  GTTAGTTTAT  TAGGTATTGT  TTCGTTTGTA  ATG TTA         176
                                                            Met Leu
                                                              1

GCA GCT GCT AGT TGT ACT TCA GCA GCT ACA CCA ACT CCA AAC CCT GAA             224
Ala Ala Ala Ser Cys Thr Ser Ala Ala Thr Pro Thr Pro Asn Pro Glu
         5               10                  15

CCA AAA CCA ACT CCA AAC CCT GAA CCA AAA CCA GAT CCA ATG CCA AAC             272
Pro Lys Pro Thr Pro Asn Pro Glu Pro Lys Pro Asp Pro Met Pro Asn
     20              25                  30

CCT CCT AGT GGT GGT AAC ATG AAT GGT GGA AAC ACC AAC CCA AGT GAT             320
Pro Pro Ser Gly Gly Asn Met Asn Gly Gly Asn Thr Asn Pro Ser Asp
 35              40                  45                      50

GGG CAA GGC ATG ATG AAT GCA GCT GCT AAA GAA TTA GCA GAC GCA AAA             368
Gly Gln Gly Met Met Asn Ala Ala Ala Lys Glu Leu Ala Asp Ala Lys
                     55                  60                  65

GCT GCT TTA ACT ACT TTG ATT AAT GGT GAA ACT GCA AAT CTT GCG TCA             416
Ala Ala Leu Thr Thr Leu Ile Asn Gly Glu Thr Ala Asn Leu Ala Ser
             70                  75                  80

TAT GAA GAC TAT GCT AAG ATC AAA AGT GAA TTA ACA TCA GCG TAT GAA             464
Tyr Glu Asp Tyr Ala Lys Ile Lys Ser Glu Leu Thr Ser Ala Tyr Glu
         85                  90                  95

ACA GCT AAA GCA GTT TCA GCT AAA ACT GGT GCA ACT CTA AAT GAG GTT             512
Thr Ala Lys Ala Val Ser Ala Lys Thr Gly Ala Thr Leu Asn Glu Val
     100             105                 110

AAT GAG GCA AAA ACT ACA TTA GAT GCT GCT ATT AAA AAA GCT GCT AGT             560
Asn Glu Ala Lys Thr Thr Leu Asp Ala Ala Ile Lys Lys Ala Ala Ser
115             120                 125                     130

GCT AAG AAT GAT TTT GAT GCA CAG CAC GGG TCA CTA GTG GAA GCA TAT             608
Ala Lys Asn Asp Phe Asp Ala Gln His Gly Ser Leu Val Glu Ala Tyr
                 135                 140                 145

AAC AAT CTA AAA GAA ACG TTA AAA GAA GAA AAA ACT AAT TTA GAT TCT             656
Asn Asn Leu Lys Glu Thr Leu Lys Glu Glu Lys Thr Asn Leu Asp Ser
             150                 155                 160

CTT GCA AAC GAA AAT TAT GCA GCA ATC AGA ACT AAT CTT AAT AGT TTA             704
Leu Ala Asn Glu Asn Tyr Ala Ala Ile Arg Thr Asn Leu Asn Ser Leu
         165                 170                 175

TAT GAA AAA GCC AAT ACT ATT GTT ACA GCT ACT TTA GAC CCT GCT ACT             752
Tyr Glu Lys Ala Asn Thr Ile Val Thr Ala Thr Leu Asp Pro Ala Thr
     180                 185                 190
```

| | | | | | | | | | | | | | | | | |
|---|---|---|---|---|---|---|---|---|---|---|---|---|---|---|---|---|
| GGA | AAT | ATT | CCT | GAA | GTT | ATG | AGT | GTA | ACA | CAA | GCT | AAT | CAA | GAT | ATT | 800 |
| Gly | Asn | Ile | Pro | Glu | Val | Met | Ser | Val | Thr | Gln | Ala | Asn | Gln | Asp | Ile | |
| 195 | | | | 200 | | | | | 205 | | | | | | 210 | |
| ACT | AAT | GCA | ACT | TCA | AGA | CTA | ATA | GCT | TGA | AAA | CAA | AAT | GCT | GAT | AAT | 848 |
| Thr | Asn | Ala | Thr | Ser | Arg | Leu | Ile | Ala | Trp | Lys | Gln | Asn | Ala | Asp | Asn | |
| | | | | 215 | | | | 220 | | | | | 225 | | | |
| TTA | GCT | AAC | AGT | TTT | ATC | AAA | CAG | TCT | TTA | GTT | AAA | AAT | AAT | TTG | ACT | 896 |
| Leu | Ala | Asn | Ser | Phe | Ile | Lys | Gln | Ser | Leu | Val | Lys | Asn | Asn | Leu | Thr | |
| | | | 230 | | | | | 235 | | | | | 240 | | | |
| AGA | GTT | GAT | GTA | GCA | AAT | AAT | CAG | GAG | CAA | CCA | GCA | AAT | TAC | AGT | TTT | 944 |
| Arg | Val | Asp | Val | Ala | Asn | Asn | Gln | Glu | Gln | Pro | Ala | Asn | Tyr | Ser | Phe | |
| | | | 245 | | | | | 250 | | | | | 255 | | | |
| GTT | GGT | TTT | AGT | GTT | AAT | GTT | GAT | ACT | CCT | AAC | TGA | AAT | TTT | GCG | CAA | 992 |
| Val | Gly | Phe | Ser | Val | Asn | Val | Asp | Thr | Pro | Asn | Trp | Asn | Phe | Ala | Gln | |
| | 260 | | | | | 265 | | | | | 270 | | | | | |
| AGA | AAA | GTT | TGG | GCC | TCT | GAA | AAT | ACT | CCT | TTA | GCA | ACT | ACA | CCA | GCT | 1040 |
| Arg | Lys | Val | Trp | Ala | Ser | Glu | Asn | Thr | Pro | Leu | Ala | Thr | Thr | Pro | Ala | |
| 275 | | | | | 280 | | | | | 285 | | | | | 290 | |
| GAA | GAT | GCA | ACA | CAA | CAA | GCT | GCA | TCC | TTA | ACA | GAT | GTT | TCA | TGA | ATC | 1088 |
| Glu | Asp | Ala | Thr | Gln | Gln | Ala | Ala | Ser | Leu | Thr | Asp | Val | Ser | Trp | Ile | |
| | | | | 295 | | | | | 300 | | | | | 305 | | |
| TAT | AGT | TTA | AAT | GGT | GCT | GAA | GCT | AAA | TAC | ACA | TTA | AGC | TTT | CGT | TAC | 1136 |
| Tyr | Ser | Leu | Asn | Gly | Ala | Glu | Ala | Lys | Tyr | Thr | Leu | Ser | Phe | Arg | Tyr | |
| | | | 310 | | | | | 315 | | | | | 320 | | | |
| TTT | GGA | GCT | GAA | AAA | ACA | GCT | TAC | TTA | TAT | TTC | CCT | TAT | AAA | TTA | GTT | 1184 |
| Phe | Gly | Ala | Glu | Lys | Thr | Ala | Tyr | Leu | Tyr | Phe | Pro | Tyr | Lys | Leu | Val | |
| | | 325 | | | | | 330 | | | | | 335 | | | | |
| AAA | ACT | AGT | GAT | AAT | GTT | GGT | TTA | CAA | TAT | AAG | TTA | AAT | GGT | GGT | GAT | 1232 |
| Lys | Thr | Ser | Asp | Asn | Val | Gly | Leu | Gln | Tyr | Lys | Leu | Asn | Gly | Gly | Asp | |
| | | 340 | | | | | 345 | | | | | 350 | | | | |
| ACT | AAA | CAA | ATT | AAC | TTT | GTA | CAA | ACT | CCA | GCT | TCT | GGT | TCA | AGT | GAT | 1280 |
| Thr | Lys | Gln | Ile | Asn | Phe | Val | Gln | Thr | Pro | Ala | Ser | Gly | Ser | Ser | Asp | |
| 355 | | | | | 360 | | | | | 365 | | | | | 370 | |
| GTT | GCT | GCT | AAT | GAA | GAA | GAA | ACT | ATG | GCT | AGT | CCT | GCT | GAA | ATG | CAG | 1328 |
| Val | Ala | Ala | Asn | Glu | Glu | Glu | Thr | Met | Ala | Ser | Pro | Ala | Glu | Met | Gln | |
| | | | | 375 | | | | 380 | | | | | 385 | | | |
| TCA | GCA | CCA | ACT | GTT | GAC | GAT | ATT | AAG | ATT | GCT | AAA | GTC | GCT | TTA | TCT | 1376 |
| Ser | Ala | Pro | Thr | Val | Asp | Asp | Ile | Lys | Ile | Ala | Lys | Val | Ala | Leu | Ser | |
| | | | 390 | | | | | 395 | | | | | 400 | | | |
| AAT | CTA | AAA | TTC | AAT | TCA | AAC | ACA | ATT | GAA | TTT | AGT | GTC | CCT | ACA | GGT | 1424 |
| Asn | Leu | Lys | Phe | Asn | Ser | Asn | Thr | Ile | Glu | Phe | Ser | Val | Pro | Thr | Gly | |
| | | 405 | | | | | 410 | | | | | 415 | | | | |
| AAA | GCA | GCT | CCT | ATG | ATT | GGA | AAT | ATG | TAT | TTA | ACT | TCA | TCT | AAT | TCG | 1472 |
| Lys | Ala | Ala | Pro | Met | Ile | Gly | Asn | Met | Tyr | Leu | Thr | Ser | Ser | Asn | Ser | |
| | 420 | | | | | 425 | | | | | 430 | | | | | |
| GAA | GTT | AAT | AAA | AAC | AAA | ATT | TAT | GAT | GAT | CTA | TTC | GGC | AAC | AGC | TTT | 1520 |
| Glu | Val | Asn | Lys | Asn | Lys | Ile | Tyr | Asp | Asp | Leu | Phe | Gly | Asn | Ser | Phe | |
| 435 | | | | | 440 | | | | | 445 | | | | | 450 | |
| AAT | AAT | GAA | AAT | AAT | CCA | ACC | GCG | GTT | ACT | GTT | GAC | CTA | TTA | AAA | GGT | 1568 |
| Asn | Asn | Glu | Asn | Asn | Pro | Thr | Ala | Val | Thr | Val | Asp | Leu | Leu | Lys | Gly | |
| | | | | 455 | | | | 460 | | | | | 465 | | | |
| TAT | AGT | CTT | GCT | GCT | AGT | TAC | AGT | ATA | TAT | GTT | CGC | CAA | TTC | AAT | GAT | 1616 |
| Tyr | Ser | Leu | Ala | Ala | Ser | Tyr | Ser | Ile | Tyr | Val | Arg | Gln | Phe | Asn | Asp | |
| | | | 470 | | | | | 475 | | | | | 480 | | | |
| TTA | AAT | ATT | CAA | AAT | GGC | ACT | GAT | ATG | GCA | AGA | TCT | CGA | ACA | GTA | TAC | 1664 |
| Leu | Asn | Ile | Gln | Asn | Gly | Thr | Asp | Met | Ala | Arg | Ser | Arg | Thr | Val | Tyr | |
| | | 485 | | | | | 490 | | | | | 495 | | | | |
| TTA | GTT | GGG | TTA | ATT | GGT | AGT | AAT | GCA | AGT | AGA | TCA | ATT | AGG | AAC | CTA | 1712 |
| Leu | Val | Gly | Leu | Ile | Gly | Ser | Asn | Ala | Ser | Arg | Ser | Ile | Arg | Asn | Leu | |
| | 500 | | | | | 505 | | | | | 510 | | | | | |

| | | | | | | | | | | | | | | | |
|---|---|---|---|---|---|---|---|---|---|---|---|---|---|---|---|
| TCA | AAT | GTA | AGA | ACT | TCT | CCT | AAC | ACG | GTT | AGT | ACC | AAT | AGA | ACA | TTT | 1760 |
| Ser | Asn | Val | Arg | Thr | Ser | Pro | Asn | Thr | Val | Ser | Thr | Asn | Arg | Thr | Phe |
| 515 | | | | 520 | | | | 525 | | | | | | 530 | |
| ACA | ATA | TAT | GTA | AAT | GCT | CCA | AAG | TCA | GGT | GAT | TAT | TAT | CTA | AGT | GGT | 1808 |
| Thr | Ile | Tyr | Val | Asn | Ala | Pro | Lys | Ser | Gly | Asp | Tyr | Tyr | Leu | Ser | Gly |
| | | | | 535 | | | | 540 | | | | | 545 | | |
| TCG | TAT | CTT | ACA | AAT | CAA | AAT | AGA | AAT | ATT | AAA | TTC | TTA | AAT | AGC | AGC | 1856 |
| Ser | Tyr | Leu | Thr | Asn | Gln | Asn | Arg | Asn | Ile | Lys | Phe | Leu | Asn | Ser | Ser |
| | | | 550 | | | | 555 | | | | | 560 | | | |
| TCT | GAT | CAG | ACT | AGT | AGT | AAT | TCT | CTA | ACA | CTA | AAT | GTT | AAG | GCT | CAA | 1904 |
| Ser | Asp | Gln | Thr | Ser | Ser | Asn | Ser | Leu | Thr | Leu | Asn | Val | Lys | Ala | Gln |
| | | 565 | | | | 570 | | | | | 575 | | | | |
| ACA | AAT | TGA | GAG | ACT | TTA | GGA | AAT | TTC | GAT | ACA | TCT | AAT | AAT | ACG | AAT | 1952 |
| Thr | Asn | Trp | Glu | Thr | Leu | Gly | Asn | Phe | Asp | Thr | Ser | Asn | Asn | Thr | Asn |
| | 580 | | | | 585 | | | | 590 | | | | | | |
| ATT | GTT | ACT | AAT | AGT | GGA | TCA | AGC | ACA | ACA | ACA | GGC | CGG | ACT | TTA | AAT | 2000 |
| Ile | Val | Thr | Asn | Ser | Gly | Ser | Ser | Thr | Thr | Thr | Gly | Arg | Thr | Leu | Asn |
| 595 | | | | 600 | | | | 605 | | | | | 610 | | |
| TTA | AAA | CAA | GGA | TTA | AAC | AAA | ATT | GTT | ATC | AGT | GGA | GTA | GGT | AAT | GGT | 2048 |
| Leu | Lys | Gln | Gly | Leu | Asn | Lys | Ile | Val | Ile | Ser | Gly | Val | Gly | Asn | Gly |
| | | | 615 | | | | 620 | | | | | 625 | | | |
| AAT | ACT | CCT | TTC | ATA | GGT | AAC | TTA | ACA | TTT | ACT | TTG | ATG | GAT | AAA | ACA | 2096 |
| Asn | Thr | Pro | Phe | Ile | Gly | Asn | Leu | Thr | Phe | Thr | Leu | Met | Asp | Lys | Thr |
| | | 630 | | | | 635 | | | | | 640 | | | | |
| GCT | AGT | CCT | GTA | GTT | GAT | GAC | ACT | ATT | TTA | GAA | GGA | TCT | ATA | GAA | GCT | 2144 |
| Ala | Ser | Pro | Val | Val | Asp | Asp | Thr | Ile | Leu | Glu | Gly | Ser | Ile | Glu | Ala |
| | | 645 | | | | 650 | | | | | 655 | | | | |
| GGT | TCA | AAA | TAAAAAATTA | TGTTTTTTA | AATCTTTTTT | CAAGGATCAT | | | | | | | | | | 2193 |
| Gly | Ser | Lys | | | | | | | | | | | | | |
| | | 660 | | | | | | | | | | | | | |

| | | | | | |
|---|---|---|---|---|---|
| GTTTCTGTTT | AAACGCTAAG | TTAGTTAGAT | AATAAAATAA | AAGTTATTTG | TTTTACTCCA | 2253 |
| TGTAATATGG | CATGAAATCT | GAATCAAACT | TCAGATTTCA | TGTTTTTTTT | ATTAAGGAAG | 2313 |
| CAAATATGAG | ATACTAGCAG | CCTTTTGTCT | ACTATACTTA | TGATCGAACT | AGATCT | 2369 |

( 2 ) INFORMATION FOR SEQ ID NO:2:

( i ) SEQUENCE CHARACTERISTICS:
        ( A ) LENGTH: 661 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Leu | Ala | Ala | Ala | Ser | Cys | Thr | Ser | Ala | Ala | Thr | Pro | Thr | Pro | Asn |
| 1 | | | | 5 | | | | 10 | | | | 15 | | | |
| Pro | Glu | Pro | Lys | Pro | Thr | Pro | Asn | Pro | Glu | Pro | Lys | Pro | Asp | Pro | Met |
| | | | 20 | | | | 25 | | | | 30 | | | | |
| Pro | Asn | Pro | Pro | Ser | Gly | Gly | Asn | Met | Asn | Gly | Gly | Asn | Thr | Asn | Pro |
| | | 35 | | | | 40 | | | | 45 | | | | | |
| Ser | Asp | Gly | Gln | Gly | Met | Met | Asn | Ala | Ala | Ala | Lys | Glu | Leu | Ala | Asp |
| | 50 | | | | 55 | | | | 60 | | | | | | |
| Ala | Lys | Ala | Ala | Leu | Thr | Thr | Leu | Ile | Asn | Gly | Glu | Thr | Ala | Asn | Leu |
| 65 | | | | 70 | | | | 75 | | | | | 80 | | |
| Ala | Ser | Tyr | Glu | Asp | Tyr | Ala | Lys | Ile | Lys | Ser | Glu | Leu | Thr | Ser | Ala |
| | | | 85 | | | | 90 | | | | 95 | | | | |
| Tyr | Glu | Thr | Ala | Lys | Ala | Val | Ser | Ala | Lys | Thr | Gly | Ala | Thr | Leu | Asn |
| | | | 100 | | | | 105 | | | | 110 | | | | |
| Glu | Val | Asn | Glu | Ala | Lys | Thr | Thr | Leu | Asp | Ala | Ala | Ile | Lys | Lys | Ala |

-continued

|  |  |  | 115 |  |  |  | 120 |  |  |  | 125 |  |  |  |
|---|---|---|---|---|---|---|---|---|---|---|---|---|---|---|
| Ala | Ser | Ala | Lys | Asn | Asp | Phe | Asp | Ala | Gln | His | Gly | Ser | Leu | Val | Glu |
|  | 130 |  |  |  |  | 135 |  |  |  |  | 140 |  |  |  |
| Ala | Tyr | Asn | Asn | Leu | Lys | Glu | Thr | Leu | Lys | Glu | Lys | Thr | Asn | Leu |
| 145 |  |  |  |  | 150 |  |  |  |  | 155 |  |  |  | 160 |
| Asp | Ser | Leu | Ala | Asn | Glu | Asn | Tyr | Ala | Ala | Ile | Arg | Thr | Asn | Leu | Asn |
|  |  |  |  | 165 |  |  |  |  | 170 |  |  |  |  | 175 |
| Ser | Leu | Tyr | Glu | Lys | Ala | Asn | Thr | Ile | Val | Thr | Ala | Thr | Leu | Asp | Pro |
|  |  |  | 180 |  |  |  |  | 185 |  |  |  |  | 190 |  |
| Ala | Thr | Gly | Asn | Ile | Pro | Glu | Val | Met | Ser | Val | Thr | Gln | Ala | Asn | Gln |
|  |  | 195 |  |  |  |  | 200 |  |  |  |  | 205 |  |  |
| Asp | Ile | Thr | Asn | Ala | Thr | Ser | Arg | Leu | Ile | Ala | Trp | Lys | Gln | Asn | Ala |
|  |  | 210 |  |  |  |  | 215 |  |  |  |  | 220 |  |  |
| Asp | Asn | Leu | Ala | Asn | Ser | Phe | Ile | Lys | Gln | Ser | Leu | Val | Lys | Asn | Asn |
| 225 |  |  |  |  | 230 |  |  |  |  | 235 |  |  |  |  | 240 |
| Leu | Thr | Arg | Val | Asp | Val | Ala | Asn | Asn | Gln | Gln | Pro | Ala | Asn | Tyr |
|  |  |  |  | 245 |  |  |  |  | 250 |  |  |  |  | 255 |
| Ser | Phe | Val | Gly | Phe | Ser | Val | Asn | Val | Asp | Thr | Pro | Asn | Trp | Asn | Phe |
|  |  |  | 260 |  |  |  |  | 265 |  |  |  |  | 270 |  |
| Ala | Gln | Arg | Lys | Val | Trp | Ala | Ser | Glu | Asn | Thr | Pro | Leu | Ala | Thr | Thr |
|  |  | 275 |  |  |  |  | 280 |  |  |  |  | 285 |  |  |
| Pro | Ala | Glu | Asp | Ala | Thr | Gln | Gln | Ala | Ala | Ser | Leu | Thr | Asp | Val | Ser |
|  | 290 |  |  |  |  | 295 |  |  |  |  | 300 |  |  |  |
| Trp | Ile | Tyr | Ser | Leu | Asn | Gly | Ala | Glu | Ala | Lys | Tyr | Thr | Leu | Ser | Phe |
| 305 |  |  |  |  | 310 |  |  |  |  | 315 |  |  |  |  | 320 |
| Arg | Tyr | Phe | Gly | Ala | Glu | Lys | Thr | Ala | Tyr | Leu | Tyr | Phe | Pro | Tyr | Lys |
|  |  |  |  | 325 |  |  |  |  | 330 |  |  |  |  | 335 |
| Leu | Val | Lys | Thr | Ser | Asp | Asn | Val | Gly | Leu | Gln | Tyr | Lys | Leu | Asn | Gly |
|  |  |  | 340 |  |  |  |  | 345 |  |  |  |  | 350 |  |
| Gly | Asp | Thr | Lys | Gln | Ile | Asn | Phe | Val | Gln | Thr | Pro | Ala | Ser | Gly | Ser |
|  |  | 355 |  |  |  |  | 360 |  |  |  |  | 365 |  |  |
| Ser | Asp | Val | Ala | Ala | Asn | Glu | Glu | Glu | Thr | Met | Ala | Ser | Pro | Ala | Glu |
|  | 370 |  |  |  |  | 375 |  |  |  |  | 380 |  |  |  |
| Met | Gln | Ser | Ala | Pro | Thr | Val | Asp | Asp | Ile | Lys | Ile | Ala | Lys | Val | Ala |
| 385 |  |  |  |  | 390 |  |  |  |  | 395 |  |  |  |  | 400 |
| Leu | Ser | Asn | Leu | Lys | Phe | Asn | Ser | Asn | Thr | Ile | Glu | Phe | Ser | Val | Pro |
|  |  |  |  | 405 |  |  |  |  | 410 |  |  |  |  | 415 |
| Thr | Gly | Lys | Ala | Ala | Pro | Met | Ile | Gly | Asn | Met | Tyr | Leu | Thr | Ser | Ser |
|  |  |  | 420 |  |  |  |  | 425 |  |  |  |  | 430 |  |
| Asn | Ser | Glu | Val | Asn | Lys | Asn | Lys | Ile | Tyr | Asp | Asp | Leu | Phe | Gly | Asn |
|  |  | 435 |  |  |  |  | 440 |  |  |  |  | 445 |  |  |
| Ser | Phe | Asn | Asn | Glu | Asn | Asn | Pro | Thr | Ala | Val | Thr | Val | Asp | Leu | Leu |
| 450 |  |  |  |  | 455 |  |  |  |  | 460 |  |  |  |  |
| Lys | Gly | Tyr | Ser | Leu | Ala | Ala | Ser | Tyr | Ser | Ile | Tyr | Val | Arg | Gln | Phe |
| 465 |  |  |  |  | 470 |  |  |  |  | 475 |  |  |  |  | 480 |
| Asn | Asp | Leu | Asn | Ile | Gln | Asn | Gly | Thr | Asp | Met | Ala | Arg | Ser | Arg | Thr |
|  |  |  |  | 485 |  |  |  |  | 490 |  |  |  |  | 495 |
| Val | Tyr | Leu | Val | Gly | Leu | Ile | Gly | Ser | Asn | Ala | Ser | Arg | Ser | Ile | Arg |
|  |  |  | 500 |  |  |  |  | 505 |  |  |  |  | 510 |  |
| Asn | Leu | Ser | Asn | Val | Arg | Thr | Ser | Pro | Asn | Thr | Val | Ser | Thr | Asn | Arg |
|  |  | 515 |  |  |  |  | 520 |  |  |  |  | 525 |  |  |
| Thr | Phe | Thr | Ile | Tyr | Val | Asn | Ala | Pro | Lys | Ser | Gly | Asp | Tyr | Tyr | Leu |
|  |  | 530 |  |  |  |  | 535 |  |  |  |  | 540 |  |  |

| Ser | Gly | Ser | Tyr | Leu | Thr | Asn | Gln | Asn | Arg | Asn | Ile | Lys | Phe | Leu | Asn |
| 545 | | | | | 550 | | | | 555 | | | | | | 560 |

| Ser | Ser | Ser | Asp | Gln | Thr | Ser | Ser | Asn | Ser | Leu | Thr | Leu | Asn | Val | Lys |
| | | | | 565 | | | | | 570 | | | | | 575 | |

| Ala | Gln | Thr | Asn | Trp | Glu | Thr | Leu | Gly | Asn | Phe | Asp | Thr | Ser | Asn | Asn |
| | | | 580 | | | | | 585 | | | | | 590 | | |

| Thr | Asn | Ile | Val | Thr | Asn | Ser | Gly | Ser | Ser | Thr | Thr | Thr | Gly | Arg | Thr |
| | | 595 | | | | | 600 | | | | | 605 | | | |

| Leu | Asn | Leu | Lys | Gln | Gly | Leu | Asn | Lys | Ile | Val | Ile | Ser | Gly | Val | Gly |
| | | 610 | | | | 615 | | | | | 620 | | | | |

| Asn | Gly | Asn | Thr | Pro | Phe | Ile | Gly | Asn | Leu | Thr | Phe | Thr | Leu | Met | Asp |
| 625 | | | | | 630 | | | | | 635 | | | | | 640 |

| Lys | Thr | Ala | Ser | Pro | Val | Val | Asp | Asp | Thr | Ile | Leu | Glu | Gly | Ser | Ile |
| | | | | 645 | | | | | 650 | | | | | 655 | |

| Glu | Ala | Gly | Ser | Lys |
| | | | 660 | |

( 2 ) INFORMATION FOR SEQ ID NO:3:

( i ) SEQUENCE CHARACTERISTICS:
        ( A ) LENGTH: 1387 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 202..1305

( x i ) SEQUENCE DESCRIPTION: SEQ ID NO:3:

```
AAAAACATCA GATTGTTAAT CTGATATCTT TGCTTAAAAA AACACAAAAT CTTCTAACAA      60

AATCCTAAAT AAATAAGCCG TTAAATTAAC TAAAAAATTA AAAAAATGGT TTTTCTTATC     120

AACCAAAATT CTCTAGTAAT AAACGCTTAT TTATTTTTAT TTTTAGTCAT CTTTTAAGAT     180

ATAAATATAT CTTAATATTC T ATG AAT AAG AAA AGA ATC ATC TTA AAG ACT       231
                        Met Asn Lys Lys Arg Ile Ile Leu Lys Thr
                         1               5                    10

ATT AGT TTG TTA GGT ACA ACA TCC TTT CTT AGC ATT GGG ATT TCT AGC       279
Ile Ser Leu Leu Gly Thr Thr Ser Phe Leu Ser Ile Gly Ile Ser Ser
             15                  20                  25

TGT ATG TCT ATT ACT AAA AAA GAC GCA AAC CCA AAT AAT GGC CAA ACC       327
Cys Met Ser Ile Thr Lys Lys Asp Ala Asn Pro Asn Asn Gly Gln Thr
         30                  35                  40

CAA TTA CAA GCA GCG CGA ATG GAG TTA ACT GAT CTA ATC AAT GCT AAA       375
Gln Leu Gln Ala Ala Arg Met Glu Leu Thr Asp Leu Ile Asn Ala Lys
     45                  50                  55

GCA AGG ACA TTA GCT TCA CTA CAA GAC TAT GCT AAG ATT GAA GCT AGT       423
Ala Arg Thr Leu Ala Ser Leu Gln Asp Tyr Ala Lys Ile Glu Ala Ser
 60                  65                  70

TTA TCA TCT GCT TAT AGT GAA GCT GAA ACA GTT AAC AAT AAC CTT AAT       471
Leu Ser Ser Ala Tyr Ser Glu Ala Glu Thr Val Asn Asn Asn Leu Asn
 75              80                  85                      90

GCA ACA CTA GAA CAA CTA AAA ATG GCT AAA ACT AAT TTA GAA TCA GCC       519
Ala Thr Leu Glu Gln Leu Lys Met Ala Lys Thr Asn Leu Glu Ser Ala
                 95                 100                 105

ATC AAC CAA GCT AAT ACG GAT AAA ACG ACT TTT GAT AAT GAA CAT CCA       567
Ile Asn Gln Ala Asn Thr Asp Lys Thr Thr Phe Asp Asn Glu His Pro
             110                 115                 120

AAT TTA GTT GAA GCA TAC AAA GCA CTA AAA ACC ACT TTA GAA CAA CGT       615
```

```
Asn  Leu  Val  Glu  Ala  Tyr  Lys  Ala  Leu  Lys  Thr  Thr  Leu  Glu  Gln  Arg
          125                      130                    135

GCT  ACT  AAC  CTT  GAA  GGT  TTA  GCT  TCA  ACT  GCT  TAT  AAT  CAG  ATT  CGT        663
Ala  Thr  Asn  Leu  Glu  Gly  Leu  Ala  Ser  Thr  Ala  Tyr  Asn  Gln  Ile  Arg
     140                      145                    150

AAT  AAT  TTA  GTG  GAT  CTA  TAC  AAT  AAT  GCT  AGT  AGT  TTA  ATA  ACT  AAA        711
Asn  Asn  Leu  Val  Asp  Leu  Tyr  Asn  Asn  Ala  Ser  Ser  Leu  Ile  Thr  Lys
155                      160                    165                      170

ACA  CTA  GAT  CCA  CTA  AAT  GGG  GGA  ATG  CTT  TTA  GAT  TCT  AAT  GAG  ATT        759
Thr  Leu  Asp  Pro  Leu  Asn  Gly  Gly  Met  Leu  Leu  Asp  Ser  Asn  Glu  Ile
               175                      180                      185

ACT  ACA  GTT  AAT  CGG  AAT  ATT  AAT  AAT  ACG  TTA  TCA  ACT  ATT  AAT  GAA        807
Thr  Thr  Val  Asn  Arg  Asn  Ile  Asn  Asn  Thr  Leu  Ser  Thr  Ile  Asn  Glu
               190                      195                      200

CAA  AAG  ACT  AAT  GCT  GAT  GCA  TTA  TCT  AAT  AGT  TTT  ATT  AAA  AAA  GTG        855
Gln  Lys  Thr  Asn  Ala  Asp  Ala  Leu  Ser  Asn  Ser  Phe  Ile  Lys  Lys  Val
          205                      210                    215

ATT  CAA  AAT  AAT  GAA  CAA  AGT  TTT  GTA  GGG  ACT  TTT  ACA  AAC  GCT  AAT        903
Ile  Gln  Asn  Asn  Glu  Gln  Ser  Phe  Val  Gly  Thr  Phe  Thr  Asn  Ala  Asn
          220                      225                    230

GTT  CAA  CCT  TCA  AAC  TAC  AGT  TTT  GTT  GCT  TTT  AGT  GCT  GAT  GTA  ACA        951
Val  Gln  Pro  Ser  Asn  Tyr  Ser  Phe  Val  Ala  Phe  Ser  Ala  Asp  Val  Thr
235                      240                    245                      250

CCC  GTC  AAT  TAT  AAA  TAT  GCA  AGA  AGG  ACC  GTT  TGG  AAT  GGT  GAT  GAA        999
Pro  Val  Asn  Tyr  Lys  Tyr  Ala  Arg  Arg  Thr  Val  Trp  Asn  Gly  Asp  Glu
               255                      260                      265

CCT  TCA  AGT  AGA  ATT  CTT  GCA  AAC  ACG  AAT  AGT  ATC  ACA  GAT  GTT  TCT       1047
Pro  Ser  Ser  Arg  Ile  Leu  Ala  Asn  Thr  Asn  Ser  Ile  Thr  Asp  Val  Ser
               270                      275                      280

TGG  ATT  TAT  AGT  TTA  GCT  GGA  ACA  AAC  ACG  AAG  TAC  CAA  TTT  AGT  TTT       1095
Trp  Ile  Tyr  Ser  Leu  Ala  Gly  Thr  Asn  Thr  Lys  Tyr  Gln  Phe  Ser  Phe
          285                      290                    295

AGC  AAC  TAT  GGT  CCA  TCA  ACT  GGT  TAT  TTA  TAT  TTC  CCT  TAT  AAG  TTG       1143
Ser  Asn  Tyr  Gly  Pro  Ser  Thr  Gly  Tyr  Leu  Tyr  Phe  Pro  Tyr  Lys  Leu
          300                      305                    310

GTT  AAA  GCA  GCT  GAT  GCT  AAT  AAC  GTT  GGA  TTA  CAA  TAC  AAA  TTA  AAT       1191
Val  Lys  Ala  Ala  Asp  Ala  Asn  Asn  Val  Gly  Leu  Gln  Tyr  Lys  Leu  Asn
315                      320                    325                      330

AAT  GGA  AAT  GTT  CAA  CAA  GTT  GAG  TTT  GCC  ACT  TCA  ACT  AGT  GCA  AAT       1239
Asn  Gly  Asn  Val  Gln  Gln  Val  Glu  Phe  Ala  Thr  Ser  Thr  Ser  Ala  Asn
                    335                      340                    345

AAT  ACT  ACA  GCT  AAT  CCA  ACT  CAG  CAG  TTG  ATG  AGA  TTA  AAG  TTG  CTA       1287
Asn  Thr  Thr  Ala  Asn  Pro  Thr  Gln  Gln  Leu  Met  Arg  Leu  Lys  Leu  Leu
               350                      355                    360

AAA  TCG  TTT  TAT  CAG  GTT  TAAGATTTGG  CCAAAACACA  ATCGAATTAA                     1335
Lys  Ser  Phe  Tyr  Gln  Val
          365

GTGTTCCAAC  GGGTGAAGGA  AATATGAATA  AAGTTGCGCC  AATGATTGGC  AA                       1387
```

( 2 ) INFORMATION FOR SEQ ID NO:4:

( i ) SEQUENCE CHARACTERISTICS:
        ( A ) LENGTH: 368 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Asn  Lys  Lys  Arg  Ile  Ile  Leu  Lys  Thr  Ile  Ser  Leu  Leu  Gly  Thr
1                  5                    10                     15
```

| | | | | | | | | | | | | | | |
|---|---|---|---|---|---|---|---|---|---|---|---|---|---|---|
| Thr | Ser | Phe | Leu<br>20 | Ser | Ile | Gly | Ile | Ser<br>25 | Ser | Cys | Met | Ser | Ile<br>30 | Thr | Lys |
| Lys | Asp | Ala<br>35 | Asn | Pro | Asn | Asn | Gly<br>40 | Gln | Thr | Gln | Leu | Gln<br>45 | Ala | Ala | Arg |
| Met | Glu<br>50 | Leu | Thr | Asp | Leu | Ile<br>55 | Asn | Ala | Lys | Ala | Arg<br>60 | Thr | Leu | Ala | Ser |
| Leu<br>65 | Gln | Asp | Tyr | Ala | Lys<br>70 | Ile | Glu | Ala | Ser | Leu<br>75 | Ser | Ser | Ala | Tyr | Ser<br>80 |
| Glu | Ala | Glu | Thr | Val<br>85 | Asn | Asn | Asn | Leu | Asn<br>90 | Ala | Thr | Leu | Glu | Gln<br>95 | Leu |
| Lys | Met | Ala | Lys<br>100 | Thr | Asn | Leu | Glu | Ser<br>105 | Ala | Ile | Asn | Gln | Ala<br>110 | Asn | Thr |
| Asp | Lys | Thr<br>115 | Thr | Phe | Asp | Asn | Glu<br>120 | His | Pro | Asn | Leu | Val<br>125 | Glu | Ala | Tyr |
| Lys | Ala<br>130 | Leu | Lys | Thr | Thr | Leu<br>135 | Glu | Gln | Arg | Ala | Thr<br>140 | Asn | Leu | Glu | Gly |
| Leu<br>145 | Ala | Ser | Thr | Ala | Tyr<br>150 | Asn | Gln | Ile | Arg | Asn<br>155 | Asn | Leu | Val | Asp | Leu<br>160 |
| Tyr | Asn | Asn | Ala | Ser<br>165 | Ser | Leu | Ile | Thr | Lys<br>170 | Thr | Leu | Asp | Pro | Leu<br>175 | Asn |
| Gly | Gly | Met | Leu<br>180 | Leu | Asp | Ser | Asn | Glu<br>185 | Ile | Thr | Thr | Val | Asn<br>190 | Arg | Asn |
| Ile | Asn | Asn<br>195 | Thr | Leu | Ser | Thr | Ile<br>200 | Asn | Glu | Gln | Lys | Thr<br>205 | Asn | Ala | Asp |
| Ala | Leu<br>210 | Ser | Asn | Ser | Phe | Ile<br>215 | Lys | Lys | Val | Ile | Gln<br>220 | Asn | Asn | Glu | Gln |
| Ser<br>225 | Phe | Val | Gly | Thr | Phe<br>230 | Thr | Asn | Ala | Asn | Val<br>235 | Gln | Pro | Ser | Asn | Tyr<br>240 |
| Ser | Phe | Val | Ala | Phe<br>245 | Ser | Ala | Asp | Val | Thr<br>250 | Pro | Val | Asn | Tyr | Lys<br>255 | Tyr |
| Ala | Arg | Arg | Thr<br>260 | Val | Trp | Asn | Gly | Asp<br>265 | Glu | Pro | Ser | Ser | Arg<br>270 | Ile | Leu |
| Ala | Asn | Thr<br>275 | Asn | Ser | Ile | Thr | Asp<br>280 | Val | Ser | Trp | Ile | Tyr<br>285 | Ser | Leu | Ala |
| Gly | Thr<br>290 | Asn | Thr | Lys | Tyr | Gln<br>295 | Phe | Ser | Phe | Ser | Asn<br>300 | Tyr | Gly | Pro | Ser |
| Thr<br>305 | Gly | Tyr | Leu | Tyr | Phe<br>310 | Pro | Tyr | Lys | Leu | Val<br>315 | Lys | Ala | Ala | Asp | Ala<br>320 |
| Asn | Asn | Val | Gly | Leu<br>325 | Gln | Tyr | Lys | Leu | Asn<br>330 | Asn | Gly | Asn | Val<br>335 | Gln | Gln |
| Val | Glu | Phe | Ala<br>340 | Thr | Ser | Thr | Ser | Ala<br>345 | Asn | Asn | Thr | Thr | Ala<br>350 | Asn | Pro |
| Thr | Gln | Gln<br>355 | Leu | Met | Arg | Leu | Lys<br>360 | Leu | Leu | Lys | Ser | Phe<br>365 | Tyr | Gln | Val |

( 2 ) INFORMATION FOR SEQ ID NO:5:

( i ) SEQUENCE CHARACTERISTICS:
    ( A ) LENGTH: 1945 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 97..1038

( x i ) SEQUENCE DESCRIPTION: SEQ ID NO:5:

```
CGTACGTTTT AATGGCTATT GGGCTCTTAT TTTATTGTCA GGATTGCACT AACAGCAGTT          60

ATAGCAAGCC CAATTAACTC AGTAGAAGTT ACAGAG ATG ATG AAT GGT CAA GAA          114
                                        Met Met Asn Gly Gln Glu
                                         1               5

GTC ACA ACA ACT AAA AAG ATT AGT ACG TTT GCC TTC TTA ATC AAC ATG          162
Val Thr Thr Thr Lys Lys Ile Ser Thr Phe Ala Phe Leu Ile Asn Met
             10              15                      20

TTA CCA AAT TAC CAA CTA AGT ACA CTT GGT TAC TTA CAG ATT ACA GCA          210
Leu Pro Asn Tyr Gln Leu Ser Thr Leu Gly Tyr Leu Gln Ile Thr Ala
            25                  30                  35

GCT GCT GCT GGA CTT GTA GTA GGG ATT GTA TTA CTT GCA TTA GGC GCA          258
Ala Ala Ala Gly Leu Val Val Gly Ile Val Leu Leu Ala Leu Gly Ala
 40                      45                  50

ACA TTC TTT GTT AAA ACT AGA CGT AAA ACA AAT GAA ATG CTT GCT GCA          306
Thr Phe Phe Val Lys Thr Arg Arg Lys Thr Asn Glu Met Leu Ala Ala
 55                  60                  65                   70

CTT CAA GAT GCT GAA GAA GAA GAA GTG GCA CAA GAA GAA CAA GCT GAA          354
Leu Gln Asp Ala Glu Glu Glu Glu Val Ala Gln Glu Glu Gln Ala Glu
                 75                  80                  85

GAA AAT GTT GAA GTC ACT CCA ACT CAA CAA GCT GAA GTT AAG ACT GAA          402
Glu Asn Val Glu Val Thr Pro Thr Gln Gln Ala Glu Val Lys Thr Glu
             90                  95                 100

CAA TTA ATT GGC ACA CAA TTA GTA ACA ACT GAT GTA GCT AGC AAT CAA          450
Gln Leu Ile Gly Thr Gln Leu Val Thr Thr Asp Val Ala Ser Asn Gln
            105                 110                 115

GCT GCA GGT ACT GAA CAA GTT GAA GGT GAT TTA TTA CCT CCT AGT CAA          498
Ala Ala Gly Thr Glu Gln Val Glu Gly Asp Leu Leu Pro Pro Ser Gln
 120                 125                 130

CAA CCA ACG GAA ATG CGT CCA GCT CCT TCA CCA ATG GGT AGT CCT AAG          546
Gln Pro Thr Glu Met Arg Pro Ala Pro Ser Pro Met Gly Ser Pro Lys
135                 140                 145                 150

TTA TTA GGT CCA AAC CAA GCT GGT CAT CCA CAA CAC GGA CCA CGT CCG          594
Leu Leu Gly Pro Asn Gln Ala Gly His Pro Gln His Gly Pro Arg Pro
            155                 160                 165

ATG AAT GCT CAT CCA GGT CAA CCA CGT CCT CCA ATG GGT AGT CCT AAG          642
Met Asn Ala His Pro Gly Gln Pro Arg Pro Pro Met Gly Ser Pro Lys
                170                 175                 180

TTA TTA GGT CCA AAC CAA GCT GGT CAT CCA AGA CCC ATG CCA AAT GGT          690
Leu Leu Gly Pro Asn Gln Ala Gly His Pro Arg Pro Met Pro Asn Gly
            185                 190                 195

CCA CAA AAC CAA CAA GGT CCA AGA CCA ATG AAC CCT CAA GGC AAT CCT          738
Pro Gln Asn Gln Gln Gly Pro Arg Pro Met Asn Pro Gln Gly Asn Pro
    200                 205                 210

CGT CCT GGA CCA GCT GGC CCA CGA CCT AAC GGC CCA CAA AAT TCT CAA          786
Arg Pro Gly Pro Ala Gly Pro Arg Pro Asn Gly Pro Gln Asn Ser Gln
215                 220                 225                 230

CCA CGT CCT CAA CCA GCT GGC CCA CGT CCA ATG GGA GCT GGT AGA TCT          834
Pro Arg Pro Gln Pro Ala Gly Pro Arg Pro Met Gly Ala Gly Arg Ser
                235                 240                 245

AAC CAA CCA AGA CCA ATG CCA AAT GGT CCA CAA AAC CAA CAA GGT CCA          882
Asn Gln Pro Arg Pro Met Pro Asn Gly Pro Gln Asn Gln Gln Gly Pro
            250                 255                 260

AGA CCA ATG AAC CCT CAA GGC AAT CCT CGT CCT CAA CCA GCT GGT GTC          930
Arg Pro Met Asn Pro Gln Gly Asn Pro Arg Pro Gln Pro Ala Gly Val
                265                 270                 275

AGA CCT AAC AGC CCA CAA GCT AAC CAG CCA GGA CCA CGT CCA ACG CCA          978
Arg Pro Asn Ser Pro Gln Ala Asn Gln Pro Gly Pro Arg Pro Thr Pro
 280                 285                 290
```

```
AAT AAT CCT CAA GGA CCA CGG CCA ATG GGT CCA AGA CCA AAT GGA GGA       1026
Asn Asn Pro Gln Gly Pro Arg Pro Met Gly Pro Arg Pro Asn Gly Gly
295                 300                 305                 310

CCA AAC CGA GCT TAATTAACCA ATAGATTAGC TCTAAATTTG AAAACAGTTC            1078
Pro Asn Arg Ala

ATTTCCTAGA AAATGAACTG TTTTTTTTAT TATTTGTAAG TAAATTTATT AATCAACCGC      1138

TTGTTTTGTT GAATAAAGAT AGATCACAAC ATCTTCTTGA TTTACATCTT TAATTTGCAT      1198

ATTATTGATC ATTAAAGGGA TCTTGATGAT CTGATACATC TTGTTATTCT CATAATCAAG      1258

ATAATTAAGA TGTGAAGCAC TAAAAGCAAA TAGCTCTTGT TCAGATTGGA TTAGTTCTTT      1318

AGCATTATTT AAGAACGACT GATCATCACT CAGTAATAAT AAGATCTGAT TCAAGTTTTT      1378

GATATCAGTT GCTACTTCTT GATTAACAT CAATGTTTCA TAGCGTGATA ATAAGGATTT       1438

AAAACGGTGA ATGATTGATG TCGTTGCACT TTTCTCATCG TTGGTTTCAA CGTATTGAAA      1498

AGTGTTCATT AAGTTAATGT ATTCTTGCTG GTATTTCTTA TTAATCTGAT CAGGGTTATC      1558

TGAATAGATT AAGATGTTCT TATTAGTTTG ATCAACAATA ACCATCGTTG CTTTCATTAA      1618

AGCTCAGTAA GTAAATAGTT TTTCAATCTT ATGCTTTAAT AAAAACGGGA TGATATTCTT      1678

ATGTAGGTTA AACTTATTAA AAATAAGTTT TGCAATCTGG TTGACTAGTT TATGATCAAC      1738

CTGGTTGATA GTTAATTTCT TAAGCATAAG AAGATTTTAA ATATTTAAA AAAACTATTG       1798

CTGATATGTT AAAATAGTTA AGGTATAAAA ATAATAAATT AAATATGGCT CGTAGAGATG      1858

ATCTAACCGG GCTTGGTCCT TTAGCAGGAA ATAATCGTTC TCATGCTTTA AACATTACCA      1918

AGCGTCGTTG AAACTTAAAC CTACAAA                                         1945
```

(2) INFORMATION FOR SEQ ID NO:6:

(i) SEQUENCE CHARACTERISTICS:
        (A) LENGTH: 314 amino acids
        (B) TYPE: amino acid
        (D) TOPOLOGY: linear (ii) MOLECULE TYPE: protein (xi) SEQUENCE DESCRIPTION: SEQ ID NO:6:

```
Met Met Asn Gly Gln Glu Val Thr Thr Thr Lys Lys Ile Ser Thr Phe
1               5                   10                  15

Ala Phe Leu Ile Asn Met Leu Pro Asn Tyr Gln Leu Ser Thr Leu Gly
            20                  25                  30

Tyr Leu Gln Ile Thr Ala Ala Ala Ala Gly Leu Val Val Gly Ile Val
        35                  40                  45

Leu Leu Ala Leu Gly Ala Thr Phe Phe Val Lys Thr Arg Arg Lys Thr
    50                  55                  60

Asn Glu Met Leu Ala Ala Leu Gln Asp Ala Glu Glu Glu Val Ala
65                  70                  75                  80

Gln Glu Glu Gln Ala Glu Glu Asn Val Glu Val Thr Pro Thr Gln Gln
                85                  90                  95

Ala Glu Val Lys Thr Glu Gln Leu Ile Gly Thr Gln Leu Val Thr Thr
            100                 105                 110

Asp Val Ala Ser Asn Gln Ala Ala Gly Thr Glu Gln Val Glu Gly Asp
        115                 120                 125

Leu Leu Pro Pro Ser Gln Gln Pro Thr Glu Met Arg Pro Ala Pro Ser
    130                 135                 140

Pro Met Gly Ser Pro Lys Leu Leu Gly Pro Asn Gln Ala Gly His Pro
145                 150                 155                 160
```

| | | | | | | | | | | | | | | |
|---|---|---|---|---|---|---|---|---|---|---|---|---|---|---|
| Gln | His | Gly | Pro | Arg 165 | Pro | Met | Asn | Ala | His 170 | Pro | Gly | Gln | Pro | Arg 175 | Pro |
| Pro | Met | Gly | Ser 180 | Pro | Lys | Leu | Leu | Gly 185 | Pro | Asn | Gln | Ala | Gly 190 | His | Pro |
| Arg | Pro | Met 195 | Pro | Asn | Gly | Pro | Gln 200 | Asn | Gln | Gly | Arg 205 | Pro | Met |
| Asn | Pro 210 | Gln | Gly | Asn | Pro | Arg 215 | Pro | Gly | Pro | Ala | Gly 220 | Pro | Arg | Pro | Asn |
| Gly 225 | Pro | Gln | Asn | Ser | Gln 230 | Pro | Arg | Pro | Gln | Pro 235 | Ala | Gly | Pro | Arg | Pro 240 |
| Met | Gly | Ala | Gly | Arg 245 | Ser | Asn | Gln | Pro | Arg 250 | Pro | Met | Pro | Asn | Gly 255 | Pro |
| Gln | Asn | Gln | Gln 260 | Gly | Pro | Arg | Pro | Met 265 | Asn | Pro | Gln | Gly | Asn 270 | Pro | Arg |
| Pro | Gln | Pro 275 | Ala | Gly | Val | Arg | Pro 280 | Asn | Ser | Pro | Gln | Ala 285 | Asn | Gln | Pro |
| Gly | Pro 290 | Arg | Pro | Thr | Pro | Asn 295 | Asn | Pro | Gln | Gly | Pro 300 | Arg | Pro | Met | Gly |
| Pro 305 | Arg | Pro | Asn | Gly | Gly 310 | Pro | Asn | Arg | Ala | | | | | | |

( 2 ) INFORMATION FOR SEQ ID NO:7:

( i ) SEQUENCE CHARACTERISTICS:
        ( A ) LENGTH: 2014 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 54..1883

( x i ) SEQUENCE DESCRIPTION: SEQ ID NO:7:

| | | | | | | | | | | | | | | |
|---|---|---|---|---|---|---|---|---|---|---|---|---|---|---|
| TTTATTTTA | TTTTTGGTAA | ATCTTTTAAA | ATATAAATAT | ATTTAATAT | TCT | ATG Met 1 | | | | | | | | 56 |
| AAT Asn | AAA Lys | AAA Lys | AGA Arg 5 | ATC Ile | ATC Ile | TTA Leu | AAG Lys | ACT Thr 10 | ATT Ile | AGC Ser | TTG Leu | TTA Leu | GGT Gly 15 | ACA Thr | ACA Thr | 104 |
| TCC Ser | TTT Phe | CTT Leu | AGT Ser 20 | ATT Ile | GGG Gly | ATT Ile | TCT Ser | AGC Ser 25 | TGT Cys | ATG Met | TCT Ser | ATT Ile | ACT Thr 30 | AAA Lys | AAA Lys | 152 |
| GAT Asp | GCA Ala | AAC Asn 35 | CCA Pro | AAT Asn | AAT Asn | GGC Gly | CAA Gln 40 | ACC Thr | CAA Gln | TTA Leu | GAA Glu | GCA Ala 45 | GCG Ala | CGA Arg | ATG Met | 200 |
| GAG Glu | TTA Leu 50 | ACA Thr | GAT Asp | CTA Leu | ATC Ile 55 | AAT Asn | GCT Ala | AAA Lys | GCG Ala | ATG Met 60 | ACA Thr | TTA Leu | GCT Ala | TCA Ser | CTA Leu 65 | 248 |
| CAA Gln | GAC Asp | TAT Tyr | GCC Ala | AAG Lys 70 | ATT Ile | GAA Glu | GCT Ala | AGT Ser | TTA Leu 75 | TCA Ser | TCT Ser | GCT Ala | TAT Tyr | AGT Ser 80 | GAA Glu | 296 |
| GCT Ala | GAA Glu | ACA Thr | GTT Val 85 | AAC Asn | AAT Asn | AAC Asn | CTT Leu | AAT Asn 90 | GCA Ala | ACA Thr | TTA Leu | GAA Glu | CAA Gln 95 | CTA Leu | AAA Lys | 344 |
| ATG Met | GCT Ala | AAA Lys 100 | ACT Thr | AAT Asn | TTA Leu | GAA Glu | TCA Ser 105 | GCC Ala | ATC Ile | AAC Asn | CAA Gln | GCT Ala 110 | AAT Asn | ACG Thr | GAT Asp | 392 |
| AAA | ACG | ACT | TTT | GAT | AAT | GAA | CAC | CCA | AAT | TTA | GTT | GAA | GCA | TAC | AAA | 440 |

-continued

| | | | | | | | | | | | | | | | | |
|---|---|---|---|---|---|---|---|---|---|---|---|---|---|---|---|---|
| | Lys | Thr 115 | Thr | Phe | Asp | Asn | Glu 120 | His | Pro | Asn | Leu | Val 125 | Glu | Ala | Tyr | Lys |
| GCA Ala 130 | CTA Leu | AAA Lys | ACC Thr | ACT Thr | TTA Leu 135 | GAA Glu | CAA Gln | CGT Arg | GCT Ala | ACT Thr 140 | AAC Asn | CTT Leu | GAA Glu | GGT Gly | TTG Leu 145 | 488 |
| TCA Ser | TCA Ser | ACT Thr | GCT Ala | TAT Tyr 150 | AAT Asn | CAA Gln | ATT Ile | CGC Arg | AAT Asn 155 | AAT Asn | TTA Leu | GTG Val | GAT Asp | CTA Leu | TAC Tyr 160 | 536 |
| AAT Asn | AAA Lys | GCT Ala | AGT Ser 165 | AGT Ser | TTA Leu | ATA Ile | ACT Thr | AAA Lys 170 | ACA Thr | CTA Leu | GAT Asp | CCA Pro | CTA Leu 175 | AAT Asn | GGG Gly | 584 |
| GGA Gly | ACG Thr | CTT Leu 180 | TTA Leu | GAT Asp | TCT Ser | AAT Asn | GAG Glu 185 | ATT Ile | ACT Thr | ACA Thr | GCT Ala | AAT Asn 190 | AAG Lys | AAT Asn | ATT Ile | 632 |
| AAT Asn | AAT Asn 195 | ACG Thr | TTA Leu | TCA Ser | ACT Thr | ATT Ile 200 | AAT Asn | GAA Glu | CAA Gln | AAG Lys | ACT Thr 205 | AAT Asn | GCT Ala | GAT Asp | GCA Ala | 680 |
| TTA Leu 210 | GCT Ala | AAT Asn | AGT Ser | TTT Phe | ATT Ile 215 | AAA Lys | GAA Glu | GTG Val | ATT Ile | CAA Gln 220 | AAT Asn | AAT Asn | AAA Lys | CAA Gln | AGT Ser 225 | 728 |
| TTT Phe | GTA Val | GGA Gly | ATG Met | TTT Phe 230 | ACA Thr | AAC Asn | ACT Thr | AAT Asn | GTT Val 235 | CAA Gln | CCT Pro | TCA Ser | AAC Asn | TAT Tyr 240 | AGT Ser | 776 |
| TTT Phe | GTT Val | GCT Ala | TTT Phe 245 | AGT Ser | GCT Ala | GAT Asp | GTA Val | ACA Thr 250 | CCT Pro | GTT Val | AAT Asn | TAT Tyr | AAA Lys 255 | TAT Tyr | GCA Ala | 824 |
| AGA Arg | AGA Arg | ACG Thr 260 | GTT Val | TGA Trp | AAT Asn | GGT Gly | GAT Asp 265 | GAA Glu | CCT Pro | TCA Ser | AGT Ser | AGA Arg 270 | ATT Ile | CTT Leu | GCA Ala | 872 |
| AAC Asn | ACC Thr 275 | AAT Asn | AGT Ser | ATT Ile | ACT Thr | GAT Asp 280 | GTT Val | TCA Ser | TGA Trp | ATT Ile | TAT Tyr 285 | AGT Ser | TTA Leu | TCT Ser | GGA Gly | 920 |
| ACA Thr 290 | AAC Asn | ACG Thr | AAA Lys | TAC Tyr | CAA Gln 295 | TTT Phe | AGT Ser | TTT Phe | AGC Ser | AAC Asn 300 | TAC Tyr | GGT Gly | CCA Pro | TCA Ser | ACT Thr 305 | 968 |
| GGT Gly | TAT Tyr | TTA Leu | TAT Tyr | TTC Phe 310 | CCT Pro | TAT Tyr | AAG Lys | TTG Leu | GTT Val 315 | AAA Lys | GCG Ala | GCT Ala | GAT Asp | GCT Ala 320 | AGT Ser | 1016 |
| AAT Asn | GTT Val | GGA Gly | TTA Leu 325 | CAA Gln | TAC Tyr | AAA Lys | CTA Leu | AAT Asn 330 | AAT Asn | GGA Gly | AAT Asn | GTT Val | CAA Gln 335 | CCA Pro | GTT Val | 1064 |
| GAG Glu | TTT Phe | GCC Ala | ACT Thr 340 | TCA Ser | ACT Thr | AGC Ser | GCA Ala | AAT Asn 345 | AAT Asn | ACT Thr | ACA Thr | GCT Ala | AAT Asn 350 | CCA Pro | ACT Thr | 1112 |
| CCA Pro | GCA Ala 355 | GTT Val | GAT Asp | GAG Glu | ATT Ile | AAA Lys 360 | GTT Val | GCT Ala | AAA Lys | ATC Ile | GTT Val 365 | TTA Leu | TCA Ser | GGT Gly | TTA Leu | 1160 |
| AGA Arg 370 | TTT Phe | GGC Gly | CAA Gln | AAC Asn | ACA Thr 375 | ATC Ile | GAA Glu | TTA Leu | AGT Ser | GTT Val 380 | CCA Pro | ACG Thr | GGT Gly | GAA Glu | AGA Arg 385 | 1208 |
| AAT Asn | ATG Met | AAT Asn | AAA Lys | GTT Val 390 | GCC Ala | CCA Pro | ATG Met | ATT Ile | GGT Gly 395 | AAT Asn | ATG Met | TAT Tyr | ATT Ile | ACT Thr 400 | TCA Ser | 1256 |
| TCT Ser | AAT Asn | GCT Ala | GAA Glu 405 | GCA Ala | AAT Asn | AAA Lys | AAG Lys | CAA Gln 410 | ATT Ile | TAC Tyr | GAT Asp | AGT Ser | ATT Ile 415 | TTT Phe | GGA Gly | 1304 |
| AAC Asn | ACT Thr | TCA Ser | TCA Ser 420 | CAA Gln | ACT Thr | GCT Ala | AGC Ser | CAA Gln 425 | ACA Thr | TCT Ser | GTT Val | AGT Ser | GTT Val 430 | GAT Asp | CTA Leu | 1352 |
| TTA Leu | AAA Lys | GGA Gly | TAT Tyr | AGT Ser | CTT Leu | GCA Ala | ACT Thr | AGT Ser | TCA Ser | AGA Arg | ACA Thr | TAT Tyr | ATT Ile | CGT Arg | CAA Gln | 1400 |

| | | | | | | | | | | | | | | | |
|---|---|---|---|---|---|---|---|---|---|---|---|---|---|---|---|
|Leu|Lys|Gly|Tyr|Ser|Leu|Ala|Thr|Ser|Ser|Arg|Thr|Tyr|Ile|Arg|Gln|
| |435| | | |440| | | | |445| | | | | |

| | | | | | | | | | | | | | | | |
|---|---|---|---|---|---|---|---|---|---|---|---|---|---|---|---|
|TTT|ACT|GGT|TTA|ACA|GAT|AAT|GGC|GTA|CAA|ACC|TCT|GAC|CCA|GTT|TAT|
|Phe|Thr|Gly|Leu|Thr|Asp|Asn|Gly|Val|Gln|Thr|Ser|Asp|Pro|Val|Tyr|
|450| | | | |455| | | | |460| | | | |465|

1448

| | | | | | | | | | | | | | | | |
|---|---|---|---|---|---|---|---|---|---|---|---|---|---|---|---|
|TTA|ATT|GGT|TTG|ATT|GGT|GGT|CGT|CAG|GAT|CGT|ACA|GTT|GCA|ACT|GGT|
|Leu|Ile|Gly|Leu|Ile|Gly|Gly|Arg|Gln|Asp|Arg|Thr|Val|Ala|Thr|Gly|
| | | | |470| | | | |475| | | | |480| |

1496

| | | | | | | | | | | | | | | | |
|---|---|---|---|---|---|---|---|---|---|---|---|---|---|---|---|
|ACA|ACG|AAT|ATT|CAA|AAT|TCT|CCT|GAT|GTA|GAT|AAT|GAT|AAT|AGA|ACA|
|Thr|Thr|Asn|Ile|Gln|Asn|Ser|Pro|Asp|Val|Asp|Asn|Asp|Asn|Arg|Thr|
| | | |485| | | | |490| | | | |495| | |

1544

| | | | | | | | | | | | | | | | |
|---|---|---|---|---|---|---|---|---|---|---|---|---|---|---|---|
|TTC|ACA|ATA|TAT|GTA|AAT|GCA|CCA|ATA|AAC|GGG|AAC|TAT|CAC|ATA|AGT|
|Phe|Thr|Ile|Tyr|Val|Asn|Ala|Pro|Ile|Asn|Gly|Asn|Tyr|His|Ile|Ser|
| | |500| | | | |505| | | | |510| | | |

1592

| | | | | | | | | | | | | | | | |
|---|---|---|---|---|---|---|---|---|---|---|---|---|---|---|---|
|GGT|GCG|TAT|TTA|CAA|GGA|ACG|CGT|ACA|GCA|AGA|AGT|CTG|AAA|TTC|TCA|
|Gly|Ala|Tyr|Leu|Gln|Gly|Thr|Arg|Thr|Ala|Arg|Ser|Leu|Lys|Phe|Ser|
| |515| | | | |520| | | | |525| | | | |

1640

| | | | | | | | | | | | | | | | |
|---|---|---|---|---|---|---|---|---|---|---|---|---|---|---|---|
|TCC|GGT|ACA|AGT|GGC|AGT|AAT|AAT|GAA|GTT|ACA|GTC|CTT|GGT|TTA|GAA|
|Ser|Gly|Thr|Ser|Gly|Ser|Asn|Asn|Glu|Val|Thr|Val|Leu|Gly|Leu|Glu|
|530| | | | |535| | | | |540| | | | |545|

1688

| | | | | | | | | | | | | | | | |
|---|---|---|---|---|---|---|---|---|---|---|---|---|---|---|---|
|CAA|AGG|GAT|TGA|ACA|ATA|TTA|GGT|CAC|TTT|GAT|ACA|AAG|ATG|GAT|GGT|
|Gln|Arg|Asp|Trp|Thr|Ile|Leu|Gly|His|Phe|Asp|Thr|Lys|Met|Asp|Gly|
| | | |550| | | | |555| | | | |560| | |

1736

| | | | | | | | | | | | | | | | |
|---|---|---|---|---|---|---|---|---|---|---|---|---|---|---|---|
|ACT|ACT|ACT|ATT|TCA|TGA|ACA|AAT|ACA|GCA|AGC|AAA|AGA|ACT|CTA|ACC|
|Thr|Thr|Thr|Ile|Ser|Trp|Thr|Asn|Thr|Ala|Ser|Lys|Arg|Thr|Leu|Thr|
| | | |565| | | | |570| | | | |575| | | |

1784

| | | | | | | | | | | | | | | | |
|---|---|---|---|---|---|---|---|---|---|---|---|---|---|---|---|
|TTA|AAT|AAA|GGT|CTA|AAT|AAA|ATT|ATT|GTA|AGT|GGA|GGA|ACT|CAA|GAT|
|Leu|Asn|Lys|Gly|Leu|Asn|Lys|Ile|Ile|Val|Ser|Gly|Gly|Thr|Gln|Asp|
| | |580| | | | |585| | | | |590| | | |

1832

| | | | | | | | | | | | | | | | |
|---|---|---|---|---|---|---|---|---|---|---|---|---|---|---|---|
|AAC|ACA|AAT|GCT|CCA|TTT|ATC|GGT|AAC|TTA|ACA|TTT|ACT|CTC|CAT|CTA|
|Asn|Thr|Asn|Ala|Pro|Phe|Ile|Gly|Asn|Leu|Thr|Phe|Thr|Leu|His|Leu|
| |595| | | | |600| | | | |605| | | | |

1880

ACG TAGAAACTTC TATTGCAAGC TCTCAATCTG CACAACCAGT TAAAAAATAA  1933
Thr
610

GATGTTTATA TTACAGAAGC ACTGAGTTAG TTAAATAAAA TTATTAGTCC AGAACCAATC  1993

AAACGGTTCT GGTTTTTTTA T  2014

(2) INFORMATION FOR SEQ ID NO:8:

(i) SEQUENCE CHARACTERISTICS:
        (A) LENGTH: 610 amino acids
        (B) TYPE: amino acid
        (D) TOPOLOGY: linear (ii) MOLECULE TYPE: protein (xi) SEQUENCE DESCRIPTION: SEQ ID NO:8:

| | | | | | | | | | | | | | | | |
|---|---|---|---|---|---|---|---|---|---|---|---|---|---|---|---|
|Met|Asn|Lys|Lys|Arg|Ile|Ile|Leu|Lys|Thr|Ile|Ser|Leu|Leu|Gly|Thr|
|1| | | |5| | | | |10| | | | |15| |

| | | | | | | | | | | | | | | | |
|---|---|---|---|---|---|---|---|---|---|---|---|---|---|---|---|
|Thr|Ser|Phe|Leu|Ser|Ile|Gly|Ile|Ser|Ser|Cys|Met|Ser|Ile|Thr|Lys|
| | | |20| | | | |25| | | | |30| | |

| | | | | | | | | | | | | | | | |
|---|---|---|---|---|---|---|---|---|---|---|---|---|---|---|---|
|Lys|Asp|Ala|Asn|Pro|Asn|Asn|Gly|Gln|Thr|Gln|Leu|Glu|Ala|Ala|Arg|
| | |35| | | | |40| | | | |45| | | |

| | | | | | | | | | | | | | | | |
|---|---|---|---|---|---|---|---|---|---|---|---|---|---|---|---|
|Met|Glu|Leu|Thr|Asp|Leu|Ile|Asn|Ala|Lys|Ala|Met|Thr|Leu|Ala|Ser|
| |50| | | | |55| | | | |60| | | | |

| | | | | | | | | | | | | | | | |
|---|---|---|---|---|---|---|---|---|---|---|---|---|---|---|---|
|Leu|Gln|Asp|Tyr|Ala|Lys|Ile|Glu|Ala|Ser|Leu|Ser|Ser|Ala|Tyr|Ser|
|65| | | | |70| | | | |75| | | | |80|

| | | | | | | | | | | | | | | | |
|---|---|---|---|---|---|---|---|---|---|---|---|---|---|---|---|
|Glu|Ala|Glu|Thr|Val|Asn|Asn|Asn|Leu|Asn|Ala|Thr|Leu|Glu|Gln|Leu|
| | | | |85| | | | |90| | | | |95| |

| Lys | Met | Ala | Lys | Thr | Asn | Leu | Glu | Ser | Ala | Ile | Asn | Gln | Ala | Asn | Thr |
|---|---|---|---|---|---|---|---|---|---|---|---|---|---|---|---|
| | | | 100 | | | | 105 | | | | 110 | | | | |
| Asp | Lys | Thr | Thr | Phe | Asp | Asn | Glu | His | Pro | Asn | Leu | Val | Glu | Ala | Tyr |
| | 115 | | | | 120 | | | | | | 125 | | | | |
| Lys | Ala | Leu | Lys | Thr | Thr | Leu | Glu | Gln | Arg | Ala | Thr | Asn | Leu | Glu | Gly |
| | 130 | | | | 135 | | | | | 140 | | | | | |
| Leu | Ser | Ser | Thr | Ala | Tyr | Asn | Gln | Ile | Arg | Asn | Asn | Leu | Val | Asp | Leu |
| 145 | | | | | 150 | | | | | 155 | | | | | 160 |
| Tyr | Asn | Lys | Ala | Ser | Ser | Leu | Ile | Thr | Lys | Thr | Leu | Asp | Pro | Leu | Asn |
| | | | | 165 | | | | | 170 | | | | | 175 | |
| Gly | Gly | Thr | Leu | Leu | Asp | Ser | Asn | Glu | Ile | Thr | Thr | Ala | Asn | Lys | Asn |
| | | | | 180 | | | | 185 | | | | | 190 | | |
| Ile | Asn | Asn | Thr | Leu | Ser | Thr | Ile | Asn | Glu | Gln | Lys | Thr | Asn | Ala | Asp |
| | | 195 | | | | | 200 | | | | | 205 | | | |
| Ala | Leu | Ala | Asn | Ser | Phe | Ile | Lys | Glu | Val | Ile | Gln | Asn | Asn | Lys | Gln |
| | | 210 | | | | 215 | | | | | 220 | | | | |
| Ser | Phe | Val | Gly | Met | Phe | Thr | Asn | Thr | Asn | Val | Gln | Pro | Ser | Asn | Tyr |
| 225 | | | | | 230 | | | | | 235 | | | | | 240 |
| Ser | Phe | Val | Ala | Phe | Ser | Ala | Asp | Val | Thr | Pro | Val | Asn | Tyr | Lys | Tyr |
| | | | | 245 | | | | | 250 | | | | | 255 | |
| Ala | Arg | Arg | Thr | Val | Trp | Asn | Gly | Asp | Glu | Pro | Ser | Ser | Arg | Ile | Leu |
| | | | 260 | | | | | 265 | | | | | 270 | | |
| Ala | Asn | Thr | Asn | Ser | Ile | Thr | Asp | Val | Ser | Trp | Ile | Tyr | Ser | Leu | Ser |
| | | 275 | | | | | 280 | | | | | 285 | | | |
| Gly | Thr | Asn | Thr | Lys | Tyr | Gln | Phe | Ser | Phe | Ser | Asn | Tyr | Gly | Pro | Ser |
| | 290 | | | | | 295 | | | | | 300 | | | | |
| Thr | Gly | Tyr | Leu | Tyr | Phe | Pro | Tyr | Lys | Leu | Val | Lys | Ala | Ala | Asp | Ala |
| 305 | | | | | 310 | | | | | 315 | | | | | 320 |
| Ser | Asn | Val | Gly | Leu | Gln | Tyr | Lys | Leu | Asn | Asn | Gly | Asn | Val | Gln | Pro |
| | | | | 325 | | | | | 330 | | | | | 335 | |
| Val | Glu | Phe | Ala | Thr | Ser | Thr | Ser | Ala | Asn | Asn | Thr | Thr | Ala | Asn | Pro |
| | | | 340 | | | | | 345 | | | | | 350 | | |
| Thr | Pro | Ala | Val | Asp | Glu | Ile | Lys | Val | Ala | Lys | Ile | Val | Leu | Ser | Gly |
| | | 355 | | | | | 360 | | | | | 365 | | | |
| Leu | Arg | Phe | Gly | Gln | Asn | Thr | Ile | Glu | Leu | Ser | Val | Pro | Thr | Gly | Glu |
| | 370 | | | | | 375 | | | | | 380 | | | | |
| Arg | Asn | Met | Asn | Lys | Val | Ala | Pro | Met | Ile | Gly | Asn | Met | Tyr | Ile | Thr |
| 385 | | | | | 390 | | | | | 395 | | | | | 400 |
| Ser | Ser | Asn | Ala | Glu | Ala | Asn | Lys | Lys | Gln | Ile | Tyr | Asp | Ser | Ile | Phe |
| | | | | 405 | | | | | 410 | | | | | 415 | |
| Gly | Asn | Thr | Ser | Ser | Gln | Thr | Ala | Ser | Gln | Thr | Ser | Val | Ser | Val | Asp |
| | | | 420 | | | | | 425 | | | | | 430 | | |
| Leu | Leu | Lys | Gly | Tyr | Ser | Leu | Ala | Thr | Ser | Ser | Arg | Thr | Tyr | Ile | Arg |
| | | 435 | | | | | 440 | | | | | 445 | | | |
| Gln | Phe | Thr | Gly | Leu | Thr | Asp | Asn | Gly | Val | Gln | Thr | Ser | Asp | Pro | Val |
| | 450 | | | | | 455 | | | | | 460 | | | | |
| Tyr | Leu | Ile | Gly | Leu | Ile | Gly | Gly | Arg | Gln | Asp | Arg | Thr | Val | Ala | Thr |
| 465 | | | | | 470 | | | | | 475 | | | | | 480 |
| Gly | Thr | Thr | Asn | Ile | Gln | Asn | Ser | Pro | Asp | Val | Asp | Asn | Asp | Asn | Arg |
| | | | | 485 | | | | | 490 | | | | | 495 | |
| Thr | Phe | Thr | Ile | Tyr | Val | Asn | Ala | Pro | Ile | Asn | Gly | Asn | Tyr | His | Ile |
| | | | 500 | | | | | 505 | | | | | 510 | | |
| Ser | Gly | Ala | Tyr | Leu | Gln | Gly | Thr | Arg | Thr | Ala | Arg | Ser | Leu | Lys | Phe |

```
                            515                           520                             525
    Ser  Ser  Gly  Thr  Ser  Gly  Ser  Asn  Asn  Glu  Val  Thr  Val  Leu  Gly  Leu
         530                          535                     540

Glu  Gln  Arg  Asp  Trp  Thr  Ile  Leu  Gly  His  Phe  Asp  Thr  Lys  Met  Asp
    545                     550                     555                          560

Gly  Thr  Thr  Thr  Ile  Ser  Trp  Thr  Asn  Thr  Ala  Ser  Lys  Arg  Thr  Leu
                        565                     570                     575

Thr  Leu  Asn  Lys  Gly  Leu  Asn  Lys  Ile  Ile  Val  Ser  Gly  Gly  Thr  Gln
                   580                     585                          590

Asp  Asn  Thr  Asn  Ala  Pro  Phe  Ile  Gly  Asn  Leu  Thr  Phe  Thr  Leu  His
              595                     600                     605

Leu  Thr
         610
```

( 2 ) INFORMATION FOR SEQ ID NO:9:

( i ) SEQUENCE CHARACTERISTICS:
        ( A ) LENGTH: 2144 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 202..2046

( x i ) SEQUENCE DESCRIPTION: SEQ ID NO:9:

```
AAAAACATCA  GATTGTTAAT  CTGATATCTT  TGCTTAAAAA  AACACAAAAT  CTTCTAACAA         60

AATCCTAAAT  AAATAAGCCG  TTAAATTAAC  TAAAAAATTA  AAAAAATGGT  TTTTCTTATC        120

AACCAAAATT  CTCTAGTAAT  AAACGCTTAT  TTATTTTTAT  TTTTAGTCAT  CTTTTAAGAT        180

ATAAATATAT  CTTAATATTC  T  ATG  AAT  AAG  AAA  AGA  ATC  ATC  TTA  AAG  ACT   231
                           Met  Asn  Lys  Lys  Arg  Ile  Ile  Leu  Lys  Thr
                             1                   5                       10

ATT  AGT  TTG  TTA  GGT  ACA  ACA  TCC  TTT  CTT  AGC  ATT  GGG  ATT  TCT  AGC   279
Ile  Ser  Leu  Leu  Gly  Thr  Thr  Ser  Phe  Leu  Ser  Ile  Gly  Ile  Ser  Ser
               15                     20                          25

TGT  ATG  TCT  ATT  ACT  AAA  AAA  GAC  GCA  AAC  CCA  AAT  AAT  GGC  CAA  ACC   327
Cys  Met  Ser  Ile  Thr  Lys  Lys  Asp  Ala  Asn  Pro  Asn  Asn  Gly  Gln  Thr
               30                     35                          40

CAA  TTA  CAA  GCA  GCG  CGA  ATG  GAG  TTA  ACT  GAT  CTA  ATC  AAT  GCT  AAA   375
Gln  Leu  Gln  Ala  Ala  Arg  Met  Glu  Leu  Thr  Asp  Leu  Ile  Asn  Ala  Lys
               45                     50                          55

GCA  AGG  ACA  TTA  GCT  TCA  CTA  CAA  GAC  TAT  GCT  AAG  ATT  GAA  GCT  AGT   423
Ala  Arg  Thr  Leu  Ala  Ser  Leu  Gln  Asp  Tyr  Ala  Lys  Ile  Glu  Ala  Ser
          60                     65                          70

TTA  TCA  TCT  GCT  TAT  AGT  GAA  GCT  GAA  ACA  GTT  AAC  AAT  AAC  CTT  AAT   471
Leu  Ser  Ser  Ala  Tyr  Ser  Glu  Ala  Glu  Thr  Val  Asn  Asn  Asn  Leu  Asn
75                       80                     85                         90

GCA  ACA  CTA  GAA  CAA  CTA  AAA  ATG  GCT  AAA  ACT  AAT  TTA  GAA  TCA  GCC   519
Ala  Thr  Leu  Glu  Gln  Leu  Lys  Met  Ala  Lys  Thr  Asn  Leu  Glu  Ser  Ala
                         95                     100                        105

ATC  AAC  CAA  GCT  AAT  ACG  GAT  AAA  ACG  ACT  TTT  GAT  AAT  GAA  CAT  CCA   567
Ile  Asn  Gln  Ala  Asn  Thr  Asp  Lys  Thr  Thr  Phe  Asp  Asn  Glu  His  Pro
               110                    115                         120

AAT  TTA  GTT  GAA  GCA  TAC  AAA  GCA  CTA  AAA  ACC  ACT  TTA  GAA  CAA  CGT   615
Asn  Leu  Val  Glu  Ala  Tyr  Lys  Ala  Leu  Lys  Thr  Thr  Leu  Glu  Gln  Arg
          125                    130                         135

GCT  ACT  AAC  CTT  GAA  GGT  TTA  GCT  TCA  ACT  GCT  TAT  AAT  CAG  ATT  CGT   663
```

```
Ala  Thr  Asn  Leu  Glu  Gly  Leu  Ala  Ser  Thr  Ala  Tyr  Asn  Gln  Ile  Arg
     140                 145                      150

AAT  AAT  TTA  GTG  GAT  CTA  TAC  AAT  AAT  GCT  AGT  AGT  TTA  ATA  ACT  AAA       711
Asn  Asn  Leu  Val  Asp  Leu  Tyr  Asn  Asn  Ala  Ser  Ser  Leu  Ile  Thr  Lys
155                      160                      165                      170

ACA  CTA  GAT  CCA  CTA  AAT  GGG  GGA  ATG  CTT  TTA  GAT  TCT  AAT  GAG  ATT       759
Thr  Leu  Asp  Pro  Leu  Asn  Gly  Gly  Met  Leu  Leu  Asp  Ser  Asn  Glu  Ile
                    175                      180                      185

ACT  ACA  GTT  AAT  CGG  AAT  ATT  AAT  AAT  ACG  TTA  TCA  ACT  ATT  AAT  GAA       807
Thr  Thr  Val  Asn  Arg  Asn  Ile  Asn  Asn  Thr  Leu  Ser  Thr  Ile  Asn  Glu
               190                      195                      200

CAA  AAG  ACT  AAT  GCT  GAT  GCA  TTA  TCT  AAT  AGT  TTT  ATT  AAA  AAA  GTG       855
Gln  Lys  Thr  Asn  Ala  Asp  Ala  Leu  Ser  Asn  Ser  Phe  Ile  Lys  Lys  Val
          205                      210                      215

ATT  CAA  AAT  AAT  GAA  CAA  AGT  TTT  GTA  GGG  ACT  TTT  ACA  AAC  GCT  AAT       903
Ile  Gln  Asn  Asn  Glu  Gln  Ser  Phe  Val  Gly  Thr  Phe  Thr  Asn  Ala  Asn
     220                      225                      230

GTT  CAA  CCT  TCA  AAC  TAC  AGT  TTT  GTT  GCT  TTT  AGT  GCT  GAT  GTA  ACA       951
Val  Gln  Pro  Ser  Asn  Tyr  Ser  Phe  Val  Ala  Phe  Ser  Ala  Asp  Val  Thr
235                      240                      245                      250

CCC  GTC  AAT  TAT  AAA  TAT  GCA  AGA  AGG  ACC  GTT  TGG  AAT  GGT  GAT  GAA       999
Pro  Val  Asn  Tyr  Lys  Tyr  Ala  Arg  Arg  Thr  Val  Trp  Asn  Gly  Asp  Glu
                    255                      260                      265

CCT  TCA  AGT  AGA  ATT  CTT  GCA  AAC  ACG  AAT  AGT  ATC  ACA  GAT  GTT  TCT      1047
Pro  Ser  Ser  Arg  Ile  Leu  Ala  Asn  Thr  Asn  Ser  Ile  Thr  Asp  Val  Ser
               270                      275                      280

TGG  ATT  TAT  AGT  TTA  GCT  GGA  ACG  AAC  ACG  AAG  TAC  CAA  TTT  AGT  TTT      1095
Trp  Ile  Tyr  Ser  Leu  Ala  Gly  Thr  Asn  Thr  Lys  Tyr  Gln  Phe  Ser  Phe
          285                      290                      295

AGC  AAC  TAT  GGT  CCA  TCA  ACT  GGT  TAT  TTA  TAT  TTC  CCT  TAT  AAG  TTG      1143
Ser  Asn  Tyr  Gly  Pro  Ser  Thr  Gly  Tyr  Leu  Tyr  Phe  Pro  Tyr  Lys  Leu
300                      305                      310

GTT  AAA  GCA  GCT  GAT  GCT  AAT  AAC  GTT  GGA  TTA  CAA  TAC  AAA  TTA  AAT      1191
Val  Lys  Ala  Ala  Asp  Ala  Asn  Asn  Val  Gly  Leu  Gln  Tyr  Lys  Leu  Asn
315                      320                      325                      330

AAT  GGA  AAT  GTT  CAA  CAA  GTT  GAG  TTT  GCC  ACT  TCA  ACT  AGT  GCA  AAT      1239
Asn  Gly  Asn  Val  Gln  Gln  Val  Glu  Phe  Ala  Thr  Ser  Thr  Ser  Ala  Asn
                    335                      340                      345

AAT  ACT  ACA  GCT  AAT  CCA  ACT  CCA  GCA  GTT  GAT  GAG  ATT  AAA  GTT  GCT      1287
Asn  Thr  Thr  Ala  Asn  Pro  Thr  Pro  Ala  Val  Asp  Glu  Ile  Lys  Val  Ala
               350                      355                      360

AAA  ATC  GTT  TTA  TCA  GGT  TTA  AGA  TTT  GGC  CAA  AAC  ACA  ATC  GAA  TTA      1335
Lys  Ile  Val  Leu  Ser  Gly  Leu  Arg  Phe  Gly  Gln  Asn  Thr  Ile  Glu  Leu
          365                      370                      375

AGT  GTT  CCA  ACG  GGT  GAA  GGA  AAT  ATG  AAT  AAA  GTT  GCG  CCA  ATG  ATT      1383
Ser  Val  Pro  Thr  Gly  Glu  Gly  Asn  Met  Asn  Lys  Val  Ala  Pro  Met  Ile
     380                      385                      390

GGC  AAC  ATT  TAT  CTT  AGC  TCA  AAT  GAA  AAT  AAT  GCT  GAT  AAG  ATC  TAC      1431
Gly  Asn  Ile  Tyr  Leu  Ser  Ser  Asn  Glu  Asn  Asn  Ala  Asp  Lys  Ile  Tyr
395                      400                      405                      410

AAT  GAT  ATC  TTT  GGT  AAC  ACA  ATC  AAC  CAA  CAG  AAT  AAT  GCT  ATT  TCT      1479
Asn  Asp  Ile  Phe  Gly  Asn  Thr  Ile  Asn  Gln  Gln  Asn  Asn  Ala  Ile  Ser
                    415                      420                      425

GTA  ATG  GTT  AAT  ATG  GTT  GAG  GGA  TAT  AAT  TTA  GCT  AGT  AGT  TAT  TCT      1527
Val  Met  Val  Asn  Met  Val  Glu  Gly  Tyr  Asn  Leu  Ala  Ser  Ser  Tyr  Ser
               430                      435                      440

CCA  GCA  TAT  AAA  CCA  ATT  AAT  GTT  TCC  ACT  GGT  GGT  GGT  CAA  ACT  CAA      1575
Pro  Ala  Tyr  Lys  Pro  Ile  Asn  Val  Ser  Thr  Gly  Gly  Gly  Gln  Thr  Gln
          445                      450                      455

CCA  TAT  TAT  GTA  ATT  GGT  TGA  TTG  GGC  GCT  AGT  GAT  CAG  AAC  CCT  AGA      1623
```

|  |  |  |  |  |  |  |  |  |  |  |  |  |  |  |  |  |
|---|---|---|---|---|---|---|---|---|---|---|---|---|---|---|---|---|
| Pro | Tyr | Tyr | Val | Ile | Gly | Trp | Leu | Gly | Ala | Ser | Asp | Gln | Asn | Pro | Arg | |
|  | 460 |  |  |  | 465 |  |  |  |  | 470 |  |  |  |  |  | |
| AAC | GCT | GTG | GGA | ACC | AAC | ATG | AAC | GTA | CAA | AGA | GTT | CCA | GCA | ACA | AAT | 1671 |
| Asn | Ala | Val | Gly | Thr | Asn | Met | Asn | Val | Gln | Arg | Val | Pro | Ala | Thr | Asn |  |
| 475 |  |  |  | 480 |  |  |  |  | 485 |  |  |  |  |  | 490 |  |
| AGC | AAC | CAA | GGC | GGA | TAT | GCT | AGA | TAT | GTC | TCT | TTT | TAT | GTT | AAT | GCT | 1719 |
| Ser | Asn | Gln | Gly | Gly | Tyr | Ala | Arg | Tyr | Val | Ser | Phe | Tyr | Val | Asn | Ala |  |
|  |  |  |  | 495 |  |  |  |  | 500 |  |  |  |  | 505 |  |  |
| CCA | CAA | GCT | GGT | TCA | TAT | TAT | ATT | AGT | GGT | AAC | TAT | AAT | AGT | TTA | ACA | 1767 |
| Pro | Gln | Ala | Gly | Ser | Tyr | Tyr | Ile | Ser | Gly | Asn | Tyr | Asn | Ser | Leu | Thr |  |
|  |  |  | 510 |  |  |  |  | 515 |  |  |  |  | 520 |  |  |  |
| GCT | AGA | GGT | CTA | GCT | GTG | TCT | ACT | GAG | AAA | ACA | TTT | ACA | ACC | AAT | GTG | 1815 |
| Ala | Arg | Gly | Leu | Ala | Val | Ser | Thr | Glu | Lys | Thr | Phe | Thr | Thr | Asn | Val |  |
|  |  | 525 |  |  |  |  | 530 |  |  |  |  | 535 |  |  |  |  |
| ATC | AAG | ATC | ACT | CAC | TTA | CAA | GTA | ATT | AAT | GCC | ACT | AAT | AGA | ATC | TTA | 1863 |
| Ile | Lys | Ile | Thr | His | Leu | Gln | Val | Ile | Asn | Ala | Thr | Asn | Arg | Ile | Leu |  |
|  | 540 |  |  |  |  | 545 |  |  |  |  | 550 |  |  |  |  |  |
| ACC | TTT | GAT | ACT | AAA | ACA | AAA | AGA | GGA | ACT | GAT | AGT | AAT | AAC | GGT | AAT | 1911 |
| Thr | Phe | Asp | Thr | Lys | Thr | Lys | Arg | Gly | Thr | Asp | Ser | Asn | Asn | Gly | Asn |  |
| 555 |  |  |  |  | 560 |  |  |  |  | 565 |  |  |  |  | 570 |  |
| ATT | ACA | TTA | GAA | GCA | AAC | AAA | GAC | ACA | ATA | ACA | TTA | ACT | AAG | GGT | TGA | 1959 |
| Ile | Thr | Leu | Glu | Ala | Asn | Lys | Asp | Thr | Ile | Thr | Leu | Thr | Lys | Gly | Trp |  |
|  |  |  |  | 575 |  |  |  |  | 580 |  |  |  |  | 585 |  |  |
| AAC | AAA | CTT | TAT | GTT | TCA | GGT | AAT | AAT | AAT | GAC | AGT | GTA | GGT | ATT | GGT | 2007 |
| Asn | Lys | Leu | Tyr | Val | Ser | Gly | Asn | Asn | Asn | Asp | Ser | Val | Gly | Ile | Gly |  |
|  |  |  | 590 |  |  |  |  | 595 |  |  |  |  | 600 |  |  |  |
| AAT | CTT | ACT | TTT | ACA | TTA | ATG | CCA | CCA | CAA | ACT | AAT | TCA | TAATTAAGAT |  |  | 2056 |
| Asn | Leu | Thr | Phe | Thr | Leu | Met | Pro | Pro | Gln | Thr | Asn | Ser |  |  |  |  |
|  |  | 605 |  |  |  |  | 610 |  |  |  |  | 615 |  |  |  |  |
| ATATTAAACA | TACCCATTTA | GATAATCTAA | ATGGGTATCT | TTTTATTGA | AAATGGCGCA |  |  |  |  |  |  |  |  |  |  | 2116 |
| TGATGAAATC | AAAGTTAAGT | TCACTAGT |  |  |  |  |  |  |  |  |  |  |  |  |  | 2144 |

( 2 ) INFORMATION FOR SEQ ID NO:10:

( i ) SEQUENCE CHARACTERISTICS:
        ( A ) LENGTH: 615 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

|  |  |  |  |  |  |  |  |  |  |  |  |  |  |  |  |
|---|---|---|---|---|---|---|---|---|---|---|---|---|---|---|---|
| Met | Asn | Lys | Lys | Arg | Ile | Ile | Leu | Lys | Thr | Ile | Ser | Leu | Leu | Gly | Thr |
| 1 |  |  |  | 5 |  |  |  |  | 10 |  |  |  |  | 15 |  |
| Thr | Ser | Phe | Leu | Ser | Ile | Gly | Ile | Ser | Ser | Cys | Met | Ser | Ile | Thr | Lys |
|  |  |  | 20 |  |  |  | 25 |  |  |  |  | 30 |  |  |  |
| Lys | Asp | Ala | Asn | Pro | Asn | Asn | Gly | Gln | Thr | Gln | Leu | Gln | Ala | Ala | Arg |
|  |  | 35 |  |  |  |  | 40 |  |  |  |  | 45 |  |  |  |
| Met | Glu | Leu | Thr | Asp | Leu | Ile | Asn | Ala | Lys | Ala | Arg | Thr | Leu | Ala | Ser |
|  | 50 |  |  |  |  | 55 |  |  |  |  | 60 |  |  |  |  |
| Leu | Gln | Asp | Tyr | Ala | Lys | Ile | Glu | Ala | Ser | Leu | Ser | Ser | Ala | Tyr | Ser |
| 65 |  |  |  |  | 70 |  |  |  |  | 75 |  |  |  |  | 80 |
| Glu | Ala | Glu | Thr | Val | Asn | Asn | Asn | Leu | Asn | Ala | Thr | Leu | Glu | Gln | Leu |
|  |  |  |  | 85 |  |  |  |  | 90 |  |  |  |  | 95 |  |
| Lys | Met | Ala | Lys | Thr | Asn | Leu | Glu | Ser | Ala | Ile | Asn | Gln | Ala | Asn | Thr |
|  |  |  | 100 |  |  |  |  | 105 |  |  |  |  | 110 |  |  |
| Asp | Lys | Thr | Thr | Phe | Asp | Asn | Glu | His | Pro | Asn | Leu | Val | Glu | Ala | Tyr |
|  |  | 115 |  |  |  |  | 120 |  |  |  |  | 125 |  |  |  |
| Lys | Ala | Leu | Lys | Thr | Thr | Leu | Glu | Gln | Arg | Ala | Thr | Asn | Leu | Glu | Gly |

-continued

|     |     |     | 130 |     |     |     |     | 135 |     |     |     |     | 140 |     |
| --- | --- | --- | --- | --- | --- | --- | --- | --- | --- | --- | --- | --- | --- | --- |
| Leu | Ala | Ser | Thr | Ala | Tyr | Asn | Gln | Ile | Arg | Asn | Leu | Val | Asp | Leu |
| 145 |     |     |     |     | 150 |     |     |     |     | 155 |     |     |     | 160 |
| Tyr | Asn | Asn | Ala | Ser | Ser | Leu | Ile | Thr | Lys | Thr | Leu | Asp | Pro | Leu | Asn |
|     |     |     |     | 165 |     |     |     |     | 170 |     |     |     |     | 175 |
| Gly | Gly | Met | Leu | Leu | Asp | Ser | Asn | Glu | Ile | Thr | Thr | Val | Asn | Arg | Asn |
|     |     |     | 180 |     |     |     |     | 185 |     |     |     |     | 190 |
| Ile | Asn | Asn | Thr | Leu | Ser | Thr | Ile | Asn | Glu | Gln | Lys | Thr | Asn | Ala | Asp |
|     |     | 195 |     |     |     |     | 200 |     |     |     |     | 205 |
| Ala | Leu | Ser | Asn | Ser | Phe | Ile | Lys | Lys | Val | Ile | Gln | Asn | Asn | Glu | Gln |
|     | 210 |     |     |     |     | 215 |     |     |     |     | 220 |
| Ser | Phe | Val | Gly | Thr | Phe | Thr | Asn | Ala | Asn | Val | Gln | Pro | Ser | Asn | Tyr |
| 225 |     |     |     |     | 230 |     |     |     |     | 235 |     |     |     |     | 240 |
| Ser | Phe | Val | Ala | Phe | Ser | Ala | Asp | Val | Thr | Pro | Val | Asn | Tyr | Lys | Tyr |
|     |     |     |     | 245 |     |     |     |     | 250 |     |     |     |     | 255 |
| Ala | Arg | Arg | Thr | Val | Trp | Asn | Gly | Asp | Glu | Pro | Ser | Ser | Arg | Ile | Leu |
|     |     |     | 260 |     |     |     |     | 265 |     |     |     |     | 270 |
| Ala | Asn | Thr | Asn | Ser | Ile | Thr | Asp | Val | Ser | Trp | Ile | Tyr | Ser | Leu | Ala |
|     |     | 275 |     |     |     |     | 280 |     |     |     |     | 285 |
| Gly | Thr | Asn | Thr | Lys | Tyr | Gln | Phe | Ser | Phe | Ser | Asn | Tyr | Gly | Pro | Ser |
|     | 290 |     |     |     |     | 295 |     |     |     |     | 300 |
| Thr | Gly | Tyr | Leu | Tyr | Phe | Pro | Tyr | Lys | Leu | Val | Lys | Ala | Ala | Asp | Ala |
| 305 |     |     |     |     | 310 |     |     |     |     | 315 |     |     |     |     | 320 |
| Asn | Asn | Val | Gly | Leu | Gln | Tyr | Lys | Leu | Asn | Asn | Gly | Asn | Val | Gln | Gln |
|     |     |     |     | 325 |     |     |     |     | 330 |     |     |     |     | 335 |
| Val | Glu | Phe | Ala | Thr | Ser | Thr | Ser | Ala | Asn | Asn | Thr | Thr | Ala | Asn | Pro |
|     |     |     | 340 |     |     |     |     | 345 |     |     |     |     | 350 |
| Thr | Pro | Ala | Val | Asp | Glu | Ile | Lys | Val | Ala | Lys | Ile | Val | Leu | Ser | Gly |
|     |     | 355 |     |     |     |     | 360 |     |     |     |     | 365 |
| Leu | Arg | Phe | Gly | Gln | Asn | Thr | Ile | Glu | Leu | Ser | Val | Pro | Thr | Gly | Glu |
|     | 370 |     |     |     |     | 375 |     |     |     |     | 380 |
| Gly | Asn | Met | Asn | Lys | Val | Ala | Pro | Met | Ile | Gly | Asn | Ile | Tyr | Leu | Ser |
| 385 |     |     |     |     | 390 |     |     |     |     | 395 |     |     |     |     | 400 |
| Ser | Asn | Glu | Asn | Asn | Ala | Asp | Lys | Ile | Tyr | Asn | Asp | Ile | Phe | Gly | Asn |
|     |     |     |     | 405 |     |     |     |     | 410 |     |     |     |     | 415 |
| Thr | Ile | Asn | Gln | Gln | Asn | Asn | Ala | Ile | Ser | Val | Met | Val | Asn | Met | Val |
|     |     |     | 420 |     |     |     |     | 425 |     |     |     |     | 430 |
| Glu | Gly | Tyr | Asn | Leu | Ala | Ser | Ser | Tyr | Ser | Pro | Ala | Tyr | Lys | Pro | Ile |
|     |     | 435 |     |     |     |     | 440 |     |     |     |     | 445 |
| Asn | Val | Ser | Thr | Gly | Gly | Gly | Gln | Thr | Gln | Pro | Tyr | Tyr | Val | Ile | Gly |
|     | 450 |     |     |     |     | 455 |     |     |     |     | 460 |
| Trp | Leu | Gly | Ala | Ser | Asp | Gln | Asn | Pro | Arg | Asn | Ala | Val | Gly | Thr | Asn |
| 465 |     |     |     |     | 470 |     |     |     |     | 475 |     |     |     |     | 480 |
| Met | Asn | Val | Gln | Arg | Val | Pro | Ala | Thr | Asn | Ser | Asn | Gln | Gly | Gly | Tyr |
|     |     |     |     | 485 |     |     |     |     | 490 |     |     |     |     | 495 |
| Ala | Arg | Tyr | Val | Ser | Phe | Tyr | Val | Asn | Ala | Pro | Gln | Ala | Gly | Ser | Tyr |
|     |     |     | 500 |     |     |     |     | 505 |     |     |     |     | 510 |
| Tyr | Ile | Ser | Gly | Asn | Tyr | Asn | Ser | Leu | Thr | Ala | Arg | Gly | Leu | Ala | Val |
|     |     | 515 |     |     |     |     | 520 |     |     |     |     | 525 |
| Ser | Thr | Glu | Lys | Thr | Phe | Thr | Thr | Asn | Val | Ile | Lys | Ile | Thr | His | Leu |
|     | 530 |     |     |     |     | 535 |     |     |     |     | 540 |
| Gln | Val | Ile | Asn | Ala | Thr | Asn | Arg | Ile | Leu | Thr | Phe | Asp | Thr | Lys | Thr |
| 545 |     |     |     |     | 550 |     |     |     |     | 555 |     |     |     |     | 560 |

| Lys | Arg | Gly | Thr | Asp<br>565 | Ser | Asn | Asn | Gly | Asn<br>570 | Ile | Thr | Leu | Glu | Ala<br>575 | Asn |
|-----|-----|-----|-----|-----|-----|-----|-----|-----|-----|-----|-----|-----|-----|-----|-----|
| Lys | Asp | Thr | Ile<br>580 | Thr | Leu | Thr | Lys | Gly<br>585 | Trp | Asn | Lys | Leu | Tyr<br>590 | Val | Ser |
| Gly | Asn | Asn<br>595 | Asn | Asp | Ser | Val | Gly<br>600 | Ile | Gly | Asn | Leu | Thr<br>605 | Phe | Thr | Leu |
| Met | Pro<br>610 | Pro | Gln | Thr | Asn | Ser<br>615 | | | | | | | | | |

( 2 ) INFORMATION FOR SEQ ID NO:11:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:11:

AATTCGAGCT CGGATCGTTG AAAAAATAAT ATAGATCCTA AAATGGAA                          4 8

( 2 ) INFORMATION FOR SEQ ID NO:12:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:12:

GATCTTCCAT TTAGGATCT ATATTATTTT TTCAACGATC CGAGCTCG                          4 8

( 2 ) INFORMATION FOR SEQ ID NO:13:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:13:

AGCTTTTTTT TTTTTTTTT TTTGGCATAT AAATAATAAA TACAATAATT AATTA            5 5

( 2 ) INFORMATION FOR SEQ ID NO:14:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:14:

CGCGTAATTA ATTATTGTAT TTATTATTTA TATGCCAAAA AAAAAAAAA AAAAA            5 5

( 2 ) INFORMATION FOR SEQ ID NO:15:

( i ) SEQUENCE CHARACTERISTICS:

(A) LENGTH: 40 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic DNA"

(x i) SEQUENCE DESCRIPTION: SEQ ID NO:15:

CGCGTAAAAA TTGAAAAACT ATTCTAATTT ATTGCACTCG    40

(2) INFORMATION FOR SEQ ID NO:16:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic DNA"

(x i) SEQUENCE DESCRIPTION: SEQ ID NO:16:

GATCCGAGTG CAATAAATTA GAATAGTTTT TCAATTTTTA    40

(2) INFORMATION FOR SEQ ID NO:17:

(i) SEQUENCE CHARACTERISTICS:
(A) LENGTH: 42 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic DNA"

(x i) SEQUENCE DESCRIPTION: SEQ ID NO:17:

GATCCCGGG CGAGCTCGCT AGCGGGCCCG CATGCGGTAC CG    42

(2) INFORMATION FOR SEQ ID NO:18:

(i) SEQUENCE CHARACTERISTICS:
(A) LENGTH: 42 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic DNA"

(x i) SEQUENCE DESCRIPTION: SEQ ID NO:18:

TCGACGGATC CGCATGCGGG CCCGCTAGCG AGCTCGCCCG GG    42

(2) INFORMATION FOR SEQ ID NO:19:

(i) SEQUENCE CHARACTERISTICS:
(A) LENGTH: 39 base pairs
(B) TYPE: nucleic acid
(C) STRANDEDNESS: single
(D) TOPOLOGY: linear (i i) MOLECULE TYPE: other nucleic acid
(A) DESCRIPTION: /desc = "synthetic DNA"

(x i) SEQUENCE DESCRIPTION: SEQ ID NO:19:

TCGACCCGGT ACATTTTTAT AAAAATGTAC CCGGGGATC    39

(2) INFORMATION FOR SEQ ID NO:20:

(i) SEQUENCE CHARACTERISTICS:

(A) LENGTH: 35 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:20:

GATCCCCGGG TACATTTTTA TAAAAATGTA CCGGG    35

(2) INFORMATION FOR SEQ ID NO:21:

(i) SEQUENCE CHARACTERISTICS:
(A) LENGTH: 14 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:21:

ATTTTTATAA AAAT    14

(2) INFORMATION FOR SEQ ID NO:22:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..66

(xi) SEQUENCE DESCRIPTION: SEQ ID NO:22:

```
ATC GCG ATC CTA CTT TTA ACA GTA GTG ACC TTA GCC ATC TCT GCA GCC    48
Ile Ala Ile Leu Leu Leu Thr Val Val Thr Leu Ala Ile Ser Ala Ala
 1               5                  10                  15

GCC CTT GCA TAT AGT ATG                                             66
Ala Leu Ala Tyr Ser Met
             20
```

(2) INFORMATION FOR SEQ ID NO:23:

(i) SEQUENCE CHARACTERISTICS:
(A) LENGTH: 22 amino acids
(B) TYPE: amino acid
(D) TOPOLOGY: linear (ii) MOLECULE TYPE: protein (xi) SEQUENCE DESCRIPTION: SEQ ID NO:23:

```
Ile Ala Ile Leu Leu Leu Thr Val Val Thr Leu Ala Ile Ser Ala Ala
 1               5                  10                  15

Ala Leu Ala Tyr Ser Met
             20
```

(2) INFORMATION FOR SEQ ID NO:24:

(i) SEQUENCE CHARACTERISTICS:
(A) LENGTH: 32 base pairs
(B) TYPE: nucleic acid
(C) STRANDEDNESS: single
(D) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:24:

TTCATCACCA TTCCAAACGG TCCTTCTTGC AT 32

( 2 ) INFORMATION FOR SEQ ID NO:25:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:25:

ACTATAAATC CAAGAAACAT C 21

( 2 ) INFORMATION FOR SEQ ID NO:26:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:26:

CTTATTCATT TTAAATTAAG ATAT 24

( 2 ) INFORMATION FOR SEQ ID NO:27:

( i ) SEQUENCE CHARACTERISTICS:
( A ) LENGTH: 97 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:27:

AGCTTTTTTT TTTTTTTTT TTTGGCATAT AAATAATAAA TACAATAATT AATTACGCGT 60

AAAAATTGAA AAACTATTCT AATTTATTGC ACTCGTC 97

( 2 ) INFORMATION FOR SEQ ID NO:28:

( i ) SEQUENCE CHARACTERISTICS:
( A ) LENGTH: 93 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc = "synthetic DNA"

( x i ) SEQUENCE DESCRIPTION: SEQ ID NO:28:

GACGAGTGCA ATAAATTAGA ATAGTTTTTC AATTTTTACG CGTAATTAAT TATTGTATTT 60

ATTATTTATA TGCCAAAAAA AAAAAAAAAA AAA 93

( 2 ) INFORMATION FOR SEQ ID NO:29:

( i ) SEQUENCE CHARACTERISTICS:
( A ) LENGTH: 95 base pairs (B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:29:

```
AGCTTTTTTT TTTTTTTTT TTTGGCATAT AAATAATAAA TACAATAATT AATTACGCGT        60
AAAAATTGAA AAACTATTCT AATTTATTGC ACTCG                                  95
```

(2) INFORMATION FOR SEQ ID NO:30:

(i) SEQUENCE CHARACTERISTICS:
(A) LENGTH: 96 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:30:

```
GATCCGAGTG CAATAAATTA GAATAGTTTT TCAATTTTTA CGCGTAATTA ATTATTGTAT        60
TTATTATTTA TATGCCAAAA AAAAAAAAAA AAAAAA                                 96
```

(2) INFORMATION FOR SEQ ID NO:31:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:31:

```
GATCCAGCAT G                                                            11
```

(2) INFORMATION FOR SEQ ID NO:32:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:32:

```
GTCCATGCTG                                                              10
```

(2) INFORMATION FOR SEQ ID NO:33:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "synthetic DNA"

(xi) SEQUENCE DESCRIPTION: SEQ ID NO:33:

```
GGGATTTCGA ATTCTATGTC T                                                 21
```

( 2 ) INFORMATION FOR SEQ ID NO:34:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:34:

GTTTTCCCAG TCACGAC                    17

( 2 ) INFORMATION FOR SEQ ID NO:35:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:35:

TCTGATCGCT AGCGCCCAAC CAACCAA            27

( 2 ) INFORMATION FOR SEQ ID NO:36:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:36:

TGATTGGGCG CTAGCGATCA                20

( 2 ) INFORMATION FOR SEQ ID NO:37:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:37:

AACATAAAGC TTGTTCCAAC CCT              23

( 2 ) INFORMATION FOR SEQ ID NO:38:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "synthetic DNA"

( x i ) SEQUENCE DESCRIPTION: SEQ ID NO:38:

TGAAACAAGC TTTATGTTT                 19

( 2 ) INFORMATION FOR SEQ ID NO:39:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:39:

CAGGAAACAG CTATGAC                                                                            17

( 2 ) INFORMATION FOR SEQ ID NO:40:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:40:

CAGGAAACAG CTATGAC                                                                            17

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:41:

ATTTCAAACG GTCCTTCTTG                                                                     20

( 2 ) INFORMATION FOR SEQ ID NO:42:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:42:

AAGAAGGACC GTTTGGAATG                                                                    20

( 2 ) INFORMATION FOR SEQ ID NO:43:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "synthetic DNA"

( x i ) SEQUENCE DESCRIPTION: SEQ ID NO:43:

GTTTTCCCAG TCACGAC                                                                           17

( 2 ) INFORMATION FOR SEQ ID NO:44:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc = "synthetic DNA"

( x i ) SEQUENCE DESCRIPTION: SEQ ID NO:44:

TCCACTTAAG CTATAAATCC ATGAAAC            27

( 2 ) INFORMATION FOR SEQ ID NO:45:

( i ) SEQUENCE CHARACTERISTICS:
           ( A ) LENGTH: 23 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc = "synthetic DNA"

( x i ) SEQUENCE DESCRIPTION: SEQ ID NO:45:

ATAGCTTAAG TGGAACAAAC ACG            23

( 2 ) INFORMATION FOR SEQ ID NO:46:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc = "synthetic DNA"

( x i ) SEQUENCE DESCRIPTION: SEQ ID NO:46:

CCCTTTGTTC TAGACCAAGG            20

( 2 ) INFORMATION FOR SEQ ID NO:47:

( i ) SEQUENCE CHARACTERISTICS:
           ( A ) LENGTH: 24 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc = "synthetic DNA"

( x i ) SEQUENCE DESCRIPTION: SEQ ID NO:47:

GGTCTAGAAC AAAGGGATTG GACA            24

( 2 ) INFORMATION FOR SEQ ID NO:48:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( i i ) MOLECULE TYPE: other nucleic acid
           ( A ) DESCRIPTION: /desc = "synthetic DNA"

( x i ) SEQUENCE DESCRIPTION: SEQ ID NO:48:

TAGTAGTGGT ACCATCCATC            20

-continued (2) INFORMATION FOR SEQ ID NO:49:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:49:

GATGGTACCA CTACTATTTC ATGGACA     27

(2) INFORMATION FOR SEQ ID NO:50:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "promoter"

(xi) SEQUENCE DESCRIPTION: SEQ ID NO:50:

TTTTTTTTT TTGGCATATA AATAATAATA AATACAATAA TTAATTACGC GTAAAAATTG     60

AAAAACTATT CTAATTTATT GCACTC     86

(2) INFORMATION FOR SEQ ID NO:51:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "promoter"

(xi) SEQUENCE DESCRIPTION: SEQ ID NO:51:

TTTTTTTTT TTTTTTTTT GGCATATAAA TAATAAATAC AATAATTAAT TACGCGTAAA     60

AATTGAAAAA CTATTCTAAT TTATTGCACT C     91

RECOMBINANT AVIPOX VIRUS ENCODING POLYPEPTIDE OF *MYCOPLASMA GALLISEPTICUM*, AND UTILIZED A LIVE VACCINE

This is a rule 371 application based on the Priority date of PCT/JP99/00541 filed Mar. 31, 1994.

TECHNICAL FIELD

The present invention relates to a novel polypeptide showing antigenicity to *Mycoplasma gallisepticum*, a fused polypeptide between the said polypeptide and a signal membrane anchor, and a recombinant Avipox virus capable of expressing a polypeptide showing antigenicity to *Mycoplasma gallisepticum*, especially a polypeptide showing antigenicity on the membrane surface of a host cell, as well as use thereof.

BACKGROUND

It is expected that a polypeptide showing antigenicity to *Mycoplasma gallisepticum* can be utilized as an effective ingredient of a vaccine for *Mycoplasma gallisepticum* infections, since an egg-laying rate and a hatching rate of eggs produced by infected chickens are markedly reduced when infected with *Mycoplasma gallisepticum*. At present, the system using *Escherichia coli* or yeast is known to prepare the antigenic protein of *Mycoplasma gallisepticum* by genetic engineering (Japanese Patent Application Laid-Open No. 2-111795). In general, it is pointed out that the production of a polypeptide in the system using bacteria involves problems that firstly an antigen is expressed in a less amount and secondly, a pyrogen originating in a host cannot be removed. It is thus the actual situation that such a system has not been practically applied yet. For this reason, studies have been made on the preparation of a polypeptide expressing an antigenicity or a recombinant live vaccine, using a recombinant virus. However, as far as *Mycoplasma gallisepticum* is concerned, any recombinant virus inserted with DNA encoding said protein has not been prepared.

In a virus protein where the virus infects cells, one type of a protein expressed is transported to the cell surface and the protein is expressed on the surface of a cell membrane (hereinafter such a state is sometimes merely referred to as being expressed on the cell surface) and another type of a protein that is not expressed on the cell surface. A representative example of the former protein is a glycoprotein contained in the coat of a virus. A recombinant virus that expresses such a protein efficiently exhibits the protein on the cell surface. It is thus considered that a high antibody titer can be induced in poultry infected with this recombinant virus (Japanese Patent Application Laid-Open No. 1-157381). On the other hand, an example of the latter type of protein includes a protein originating in bacteria, such as an antigenic protein of *Mycoplasma gallisepticum*.

It is not expectable to induce a high antibody titer from such recombinant viruses that express these proteins, since they are expressed on the cell membrane surface merely in an extremely small quantity. However, if such a protein can be expressed on the cell membrane surface in a large quantity by genetic engineering, a high antibody titer will be induced. Thus, investigations have been made to express on the membrane surface such a protein that is not principally expressed on the membrane surface. For example, there is a report that DNA encoding a signal protein having the function of secreting a protein on the cell membrane surface and DNA encoding a membrane anchor protein having the function of retaining the secreted protein so as not to leave out of the cell membrane surface are ligated with the 5' end and the 3' end of DNA encoding an antigenic protein, respectively, and a recombinant vaccinia virus inserted with the resulting hybrid DNA expresses the antigenic protein on the cell membrane surface of a host (J. Viol., 64, 4776–4783 (1990) or Mol. Cell. Biol., 6, 3191–3199 (1986)). However, DNA encoding a signal and DNA encoding a membrane anchor are independently ligated with DNA encoding an antigenic protein in these examples so that it is hardly applicable practically due to complicated preparation of a recombinant virus.

DISCLOSURE OF THE INVENTION

The present inventors have made extensive studies to provide a polypeptide having antigenicity originating in Mycoplasma and showing a high antigenicity, a polypeptide having antigenicity to *Mycoplasma gallisepticum* expressed on the cell membrane surface especially in a large quantity, DNA encoding the polypeptide, a recombinant virus inserted with the same DNA and a vaccine utilizing the virus. As a result, the present invention has come to be accomplished.

BRIEF DESCRIPTION OF THE DRAWINGS

FIG. 10 shows a restriction enzyme map of DNA including the open reading frame of TM-66 polypeptide and the position of synthetic primers on ORF.

BEST MODE FOR PRACTICING THE INVENTION

A novel polypeptide which is a first aspect of the present invention and shows an antigenicity which originates in *Mycoplasma gallisepticum* having a high antigenicity, includes a polypeptide showing an antigenicity which causes an antigen-antibody reaction with sera immunized with

Figure 7:
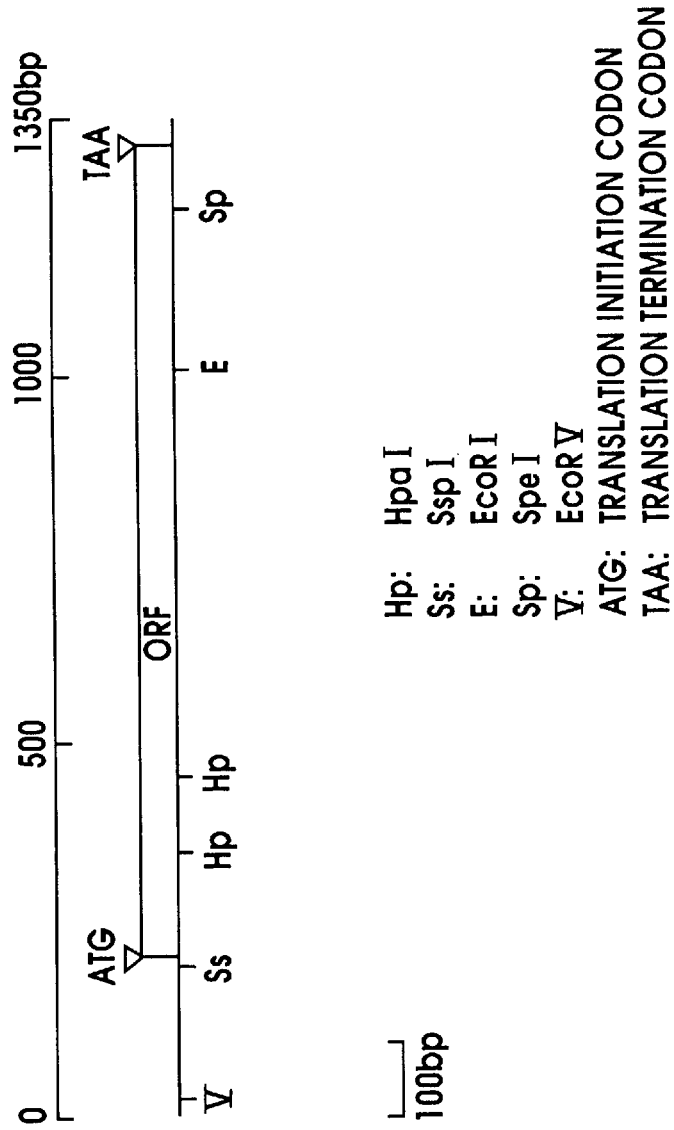
FIG. 7 shows a restriction enzyme map of DNA including the open reading frame of TTM-1 polypeptide.
Figure 8:
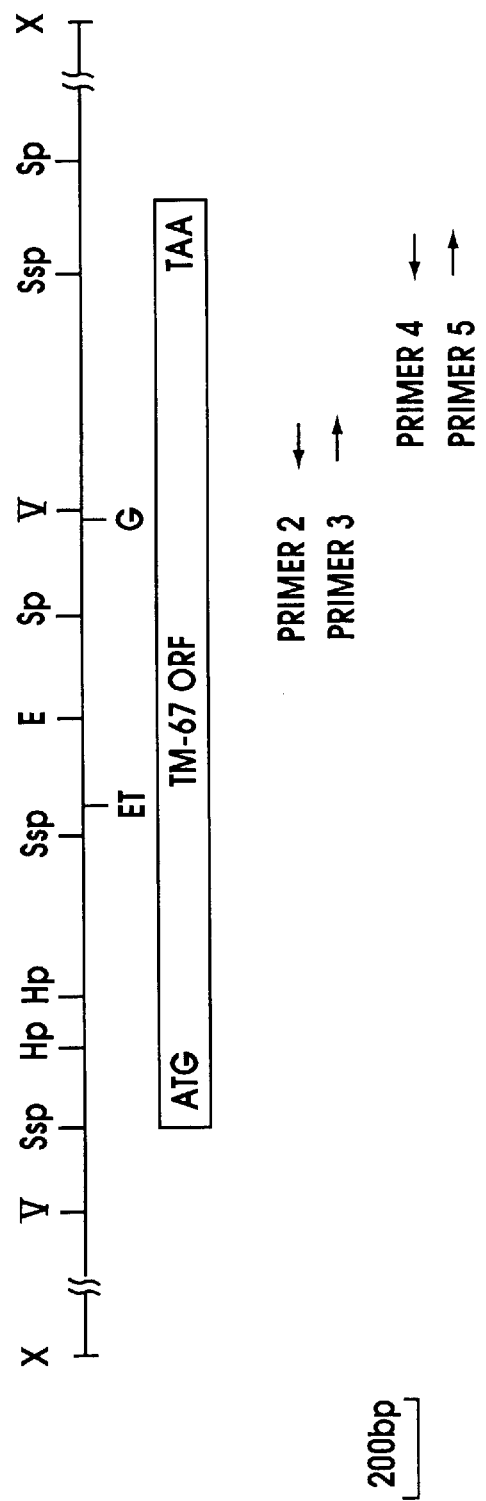
FIG. 8 shows a restriction enzyme map of DNA including the open reading frame of TM-67 polypeptide and the position of synthetic primers on ORF.

*Mycoplasma gallisepticum* or sera and which is encoded by the DNA sequence having the restriction enzyme map shown in FIG. 7 originating in *Mycoplasma gallisepticum*, or a modified polypeptide thereof. Specific examples of the polypeptide having such an polypeptide include those showing an antigenicity and having amino acid sequences of SEQ ID NOS: 1–2, 5–6, 7–8 and 9–10. The modified polypeptide showing an antigenicity referred to herein is a polypeptide in which the amino acid sequence is modified by substitution, loss, deletion, insertion or addition but which shows an antigenicity comparable to that of the aforesaid polypeptide. Taking SEQ ID NO: 1 as an example, a modified polypeptide is used to mean a polypeptide having the same antigenicity as in an antigenic protein having the amino acid sequence equivalent thereto and having a homology of at least 70% to the amino acid sequence of said polypeptide, preferably 80% or more, most preferably 90% or more. The homology referred to in the present invention is used to mean the homology determined as an index by DNA sequencing input analysis system "DNASIS" (marketed by Takara Shuzo Co.).

Hereinafter a sequence number is sometimes simply referred to as sequence in the specification. For example, Sequence No. 1 is sometimes referred to as Sequence 1.

Furthermore, the DNA which encodes the polypeptide showing an antigenicity used in the present invention includes DNA encoding a polypeptide in which the amino acid is modified by deletion, addition, insertion, loss, substitution, etc., so long as it causes an antigen-antibody reaction with sera immunized with *Mycoplasma gallisepticum* or sera and shows an antigenicity originating in *Mycoplasma gallisepticum* or an antigenicity equivalent thereto.

Avipox virus which is a second aspect of the present invention is a recombinant Avipox virus inserted with a hybrid DNA in which DNA encoding the antigenic polypeptide of *Mycoplasma gallisepticum* (hereinafter abbreviated as antigenic DNA) or DNA encoding a signal membrane anchor of Type II external membrane protein is ligated with DNA encoding a polypeptide showing an antigenicity of *Mycoplasma gallisepticum*. In order to express large quantities of the polypeptide showing an antigenicity of *Mycoplasma gallisepticum* that is not basically expressed on the surface of cell membrane, it is preferred to employ the hybrid DNA.

That is, in the second aspect of the present invention, there are provided a polypeptide showing an antigenicity of *Mycoplasma gallisepticum* (hereinafter sometimes merely referred to as antigenic protein), a fused polypeptide ligated at the N terminus of the polypeptide with a signal membrane anchor of type II outer membrane protein of a virus infected to poultry (hereinafter merely referred to as signal membrane anchor), a vaccine against *Mycoplasma gallisepticum* infections comprising as an effective ingredient the antigenic protein or the fused polypeptide, a hybrid DNA which encodes the fused polypeptide, a recombinant Avipox virus inserted into the genomic region non-essential to growth of Avipox virus (hereinafter referred to as non-essential region) with DNA encoding the antigenic protein or the hybrid DNA, and a live vaccine against *Mycoplasma gallisepticum* which comprises the Avipox virus as an effective ingredient.

The signal membrane anchor which is employed in the present invention as the second aspect is a polypeptide region having the function of transporting type II external membrane protein of a virus infected to poultry to the surface of cell membrane and expressing the transported protein on the surface of cell membrane, and is preferably derived from a virus which is non-pathogenic to human. The DNA encoding the signal membrane anchor which is employed in the present invention (hereinafter referred to as signal membrane anchor DNA) can be readily found by amino acid sequencing analysis of the hydrophobic peptide region of type II external membrane protein at the amino terminus. A specific example of the signal membrane anchor is that having the sequence shown by SEQ ID NOS: 22–23 (Mol. Cell. Biol., 10, 449–457 (1990)). This DNA codes for 22 amino acids at the amino terminus of hemagglutinin neuraminidase (hereinafter abbreviated as HN protein) of Newcastle disease virus (hereinafter abbreviated as NDV).

In order to stably exhibit the expressed antigenic protein on the cell membrane, it is effective for a hydrophilic peptide to be present at the carboxy terminal of the signal membrane anchor. Accordingly, it is preferred that DNA encoding a hydrophilic peptide be added downstream the signal membrane anchor DNA. DNA to be added comprises base pairs corresponding to 10 to 50 amino acids, preferably 20 to 30 amino acids.

Specific examples of the DNA encoding the antigenic protein in accordance with the present invention include, in addition to the four sequences as the first aspect of the present invention, DNA described in Japanese Patent Application Laid-Open No. 1-111795, a genomic DNA fragment of *Mycoplasma gallisepticum* containing the aforementioned DNA, DNA (hereinafter referred to as TTM-1) encoding a polypeptide of about 40 kilodaltons showing an antigenicity and having the sequence shown by SEQ. ID NOS: 3–4 (hereinafter referred to as TTM-1' polypeptide), DNA derived from natural *Mycoplasma gallisepticum* substantially equivalent to TTM-1' (hereinafter referred to as TTM-1), and the like. The TTM-1 and 1' are disclosed in WO 93/24646. The DNA encoding the antigenic protein may also be DNA encoding such a polypeptide that a part of the sequence is modified by substitution, loss, deletion, insertion, addition, etc. as long as it retains an antigenicity substantially equivalent to that of the antigenic protein encoded by the nucleotide sequence.

Sources for collecting such a DNA may be any of the sources so long as they belong to *Mycoplasma gallisepticum*. Specific examples include S6 strain (ATCC 15302), PG31 (ATCC 19610) and the like.

The hybrid DNA which is used in the present invention as its second aspect is the aforesaid signal membrane anchor DNA ligated with DNA encoding a polypeptide showing an antigenicity. The fused polypeptide of the present invention is a polypeptide encoded by the hybrid DNA described above which contains a part of the signal membrane anchor and a part of the polypeptide showing an antigenicity in the molecule of the polypeptide. The hybrid DNA can be produced in a conventional manner, e.g., by modifying the 3' end of the signal membrane anchor DNA and the 5' end of the DNA encoding the antigenic protein so as to form ligatable restriction enzyme digestion fragments, and ligating both DNAs according to the method for ligation using a ligase or the method for ligating both DNAs with a ligase by inserting an appropriate linker therebetween. The signal membrane anchor and the DNA encoding the polypeptide showing an antigenicity may contain therebetween, for example, DNA encoding a hydrophilic peptide, DNA encoding other antigenic protein, linker DNA, etc., so long as the signal membrane anchor DNA and the DNA encoding the polypeptide showing an antigenicity are expressed as one polypeptide. The fused polypeptide of the present invention is obtained by incubating a recombinant Avipox virus, later described, in culture cells such as chick embryo fibroblast (hereinafter referred to as CEF cells) or embryonated chorioallantoic membrane cells, etc., and purifying the desired polypeptide by a method optionally chosen from chromatography, precipitation by salting-out, density gradient centrifugation, etc. The fused polypeptide thus obtained can be used as a component vaccine which will be later described.

The recombinant Avipox virus of the present invention is a recombinant Avipox virus in which the aforesaid DNA or hybrid DNA is inserted in the non-essential region. The recombinant Avipox virus of the present invention may be constructed in a conventional manner, e.g., by the method described in Japanese Patent Application Laid-Open No. 1-168279. That is, the non-essential region of Avipox virus is incorporated into a DNA fragment, if necessary, inserted with a promoter in the non-essential region, to construct a first recombinant vector.

As the non-essential region of Avipox virus which is used in the present invention, there are a TK gene region of quail pox virus, a TK gene region of turkey pox virus and DNA fragments described in Japanese Patent Application Laid-Open 1-168279, preferably a region which causes homologous recombination with EcoRI fragment of about 7.3 Kbp, HindIII fragment of about 5.2 Kbp, EcoRI-HindIII fragment of about 5.0 Kbp, BamHI fragment of about 4.0 Kbp, described in the patent specification supra.

Examples of the vector used in the present invention include plasmids such as pBR322, pBR325, pBR327, pBR328, pUC7, pUC8, pUC9, pUC19, and the like; phages such as λ phage, M13 phage, etc.; cosmid such as pHC79 (Gene, 11, 291, 1980) and the like.

The Avipox virus used in the present invention is not particularly limited so long as it is a virus infected to poultry. Specific examples of such a virus include pigeon pox virus, fowl pox virus (hereafter abbreviated as FPV), canary pox virus, turkey pox virus, preferably turkey pox virus, pigeon pox virus and FPV, more preferably pigeon pox virus and FPV. Specific examples of the most preferred Avipox virus include FPVs such as ATCC VR-251, ATCC VR-249, ATCC VR-250, ATCC VR-229, ATCC VR-288, Nishigahara strain, Shisui strain, CEVA strain and a viral strain among CEVA strain-derived viruses which forms a large plaque when infected to chick embryo fibroblast, and a virus such as NP strain (chick embryo-conditioned pigeon pox virus Nakano strain), etc. which is akin to FPV and used as a fowlpox live vaccine strain. These strains are commercially available and readily accessible.

Then, the aforesaid antigenic DNA or hybrid DNA is inserted into the non-essential region of the first recombinant vector described above to construct a second recombinant vector. Where the hybrid DNA is employed, a promoter is generally inserted upstream the hybrid DNA. The promoter used may be a promoter having any nucleotide sequence, irrespective of a synthetic or natural promoter, as far as it effectively functions as a promoter in the system of transcription possessed by APV. Accordingly, not only a promoter inherent to APV such as a promoter of APV gene encoding thymidine kinase but also DNA derived from viruses other than APV and DNA derived from eucaryote or procaryote may also be employed in the present invention, as long as these substances meet the requirements described above. Specific examples of such a promoter include a promoter of vaccinia virus (hereinafter sometimes abbreviated as VV) described in J. Virol., 51, 662–669 (1984), more specifically a promoter of VV DNA encoding 7.5K polypeptide, a promoter of VV DNA encoding 19K polypeptide, a promoter of VV DNA encoding 42K polypeptide, a promoter of VV DNA encoding thymidine kinase, a promoter of VV DNA encoding 28K polypeptide, etc. Furthermore, there may be used a synthetic promoter obtained by modification of the Moss et al. article (J. Mol. Biol., 210, 749–776, 771–784, 1989), a promoter synthesized by Davidson, a promoter obtained by modifying a part of the Davidson promoter through deletion or change within such a range that does not lose the promoter activity (e.g., (SEQ ID NO: 50) T T T T T T T T T T T G G C A T A T A A A T A A T A A T A A A T A C A A T A A T T A A T T A C G C G T A A A A A T T G A A A A A C T A T T C T A A T T T A T T G C A C T C or (SEQ ID NO: 51) T T T T T T T T T T T T T T T T T T T G G C A T A T A A A T A A T A A A T A C A A T A A T T A A T T A C G C G T A A A A A T T G A A A A A C T A T T C T A A T T T A T T G C A C T C etc.).

Further in view of easy detection of the recombinant virus, a marker DNA such as DNA encoding β-galactosidase may also be inserted.

The recombinant Avipox virus may be constructed by transfecting the second recombinant vector described above to animal culture cells previously infected with Avipox virus and causing homologous recombination between the vector DNA and the viral genome DNA. The animal culture cells used herein may be any cells in which Avipox can grow. Specific examples of such animal culture cells are CEF cells, embryonated egg chorioallantoic membrane cells, and the like.

The desired recombinant Avipox virus is isolated from the virus infected to host cells by the method of plaque hybridization, etc. The recombinant Avipox virus may be further purified by plaque assay, etc.

The recombinant virus of the present invention constructed by the method described above can be inoculated to fowl as a live vaccine against *Mycoplasma gallisepticum* infection.

The live vaccine of the present invention is prepared by, e.g., the following method, though the process is not particularly limited. The recombinant virus of the present invention is infected to cells in which the virus can grow (hereafter referred to as host cells). After the recombinant virus grows, the cells are recovered and homogenated. The homogenate is centrifuged with a centrifuging machine to separate into the precipitates and the high titer supernatant containing the recombinant virus in a centrifuging tube. The resulting supernatant is substantially free of host cells but contains the cell culture medium and the recombinant virus and hence can be used as a live vaccine. The supernatant may be diluted by adding a pharmacologically inactive carrier, e.g., physiological saline, etc. The supernatant may be freeze-dried to be provided for use as a live vaccine. A method for administration of the live vaccine of the present invention is not particularly limited and examples of the administration include a method for scratching the skin and inoculating the live vaccine on the scratch, effecting the inoculation through injection, oral administration by mixing the live vaccine with feed or drinking water, inhalation by aerosol or spray, etc. In order to use as the live vaccine, the dosage may be the same as ordinary live vaccine; for example, approximately $10^2$ to $10^8$ plaque forming unit (hereinafter abbreviated as PFU) is inoculated per chick. Where the inoculation is effected by injection, the recombinant virus of the present invention is generally suspended in about 0.1 ml of an isotonic solvent such as physiological saline and the resulting suspension is provided for use. The live vaccine of the present invention may be stored under ordinary conditions and provided for use. For example, when the recombinant virus of the present invention is freeze-dried, it is possible to store at room temperature (20° to 22° C.). It is also possible to freeze the virus suspension at −20° to −70° C. and store the frozen suspension.

On the other hand, the component vaccine of the present invention comprises as an effective ingredient the polypeptide showing an antigenicity in accordance with the present invention, especially the fused polypeptide. The component vaccine may be administered to fowl in the same manner as in the live vaccine described above. The dose is generally in the range of approximately 1 μg to 1 mg per one subject.

According to the present invention, the polypeptide showing an Mycoplasma gallisepticum antigenicity and the fused polypeptide between the said polypeptide and the signal membrane anchor are obtained. In particular, this fused polypeptide is effective as a vaccine against Mycoplasma gallisepticum infections. By utilizing DNA encoding the fused protein, the recombinant Avipox virus which can express the polypeptide showing an Mycoplasma gallisepticum antigenicity is obtained. The recombinant Avipox virus is effective as a potent live vaccine against Mycoplasma gallisepticum infections. In addition, the novel polypeptide showing an antigenicity of the present invention and DNA encoding the same can be utilized as a component vaccine and a live vaccine, respectively.

EXAMPLES

Hereinafter the present invention will be described with reference to the examples and the reference examples but is not deemed to be limited thereto.

Reference Example 1

Obtaining of polypeptide DNA TTM-1 in which Mycoplasma gallisepticum is expressed:

(1) Preparation of genomic DNA of Mycoplasma gallisepticum

Mycoplasma gallisepticum S6 strain was cultured at 37° C. for 3 to 5 days in liquid medium prepared by supplementing 20% horse serum, 5% yeast extract, 1% glucose and a trace amount of phenol red as a pH indicator in 100 ml of PPLO broth basal medium. As Mycoplasma gallisepticum proliferated, pH of the culture broth decreased. At the point of time when the color of the pH indicator contained in the culture broth changed from red to yellow, incubation was terminated. The culture medium was centrifuged at 8000G for 20 minutes to collect the cells. The cells were then suspended in 1/10 volume of PBS based on the volume of culture medium. The suspension was again centrifuged at 10,000 rpm×G for 20 minutes to collect the cells. The collected cells were resuspended in 2.7 ml of PBS and SDS was added thereto in a final concentration of 1%. Furthermore 10 μg of RNase was added to the mixture. The mixture was incubated at 37° C. for 30 minutes to cause lysis.

The lysate was extracted 3 times with an equal volume of phenol and then 3 times with ethyl ether. The extract was precipitated with ethanol to give 200 μg of genomic DNA of Mycoplasma gallisepticum.

(2) Genomic Southern hybridization of Mycoplasma gallisepticum using TM-1 DNA as a probe After 1 μg of Mycoplasma gallisepticum DNA obtained in (1) described above was digested with XbaI, the digestion product was subjected to 0.6% low melting agarose gel electrophoresis. After the electrophoresis, the gel was immersed in an alkaline denaturation solution (0.5M NaOH, 1.5M NaCl) for 10 minutes to denature DNA and further immersed in a neutralizing solution (3M sodium acetate, pH 5.5) for 10 minutes to neutralize. Following the neutralization, the DNA was transferred onto a nylon membrane in 6-fold SSC solution (0.7M NaCl, 0.07M sodium citrate, pH 7.5). After air drying, the membrane was heated at 80° C. for 2 hours. 4-Fold SET (0.6M NaCl, 0.08M Tris-HCl, 4 mM EDTA, pH 7.8)-10-fold Denhardt-0.1% SDS-0.1% $Na_4P_2O_7$-50 μg/ml of denatured salmon sperm DNA and pUM-1 (see Japanese Patent Application Laid-Open No. 2-111795) which had been labelled in a conventional manner were added to cause hybridization at 68° C. for 14 hours. The nylon membrane was overlaid on an X ray film. Autoradiography revealed that hybridization occurred on the fragment of about 3.4 kbp.

(3) Cloning of XbaI-digested fragment of about 3.4 kbp to pUC-19 and colony hybridization After 4 μg of Mycoplasma gallisepticum DNA obtained in Example 1 (1) described above was digested with restriction enzyme XbaI, the digestion product was subject to 0.6% low melting agarose gel electrophoresis. After the electrophoresis, the fragment of about 3.4 kbp was recovered. The fragment was ligated with XbaI-digested pUC-19 using ligase and competent E. coli TG1 strain was transformed by the ligation product. The transformants were cultured at 37° C. for 15 hours in LB agar medium containing 0.003% of 5-bromo-4-chloro-3-indolyl-β-D-galactopyranoside, 0.03 mM of isopropylthio-β-D-galactopyranoside and 40 μg/ml of ampicillin. White colonies grown on the agar medium were transferred onto a nylon membrane followed by hybridization in a manner similar to (2) above. Autoradiography revealed that cloning was effected and, the thus obtained plasmid was named pUTTM1.

Figure 1:
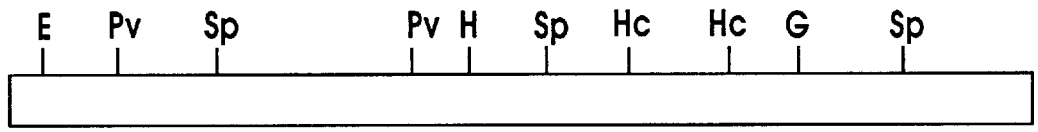
FIG. 1 shows a restriction enzyme map of DNA including the open reading frame of TM-81.
Figure 2:
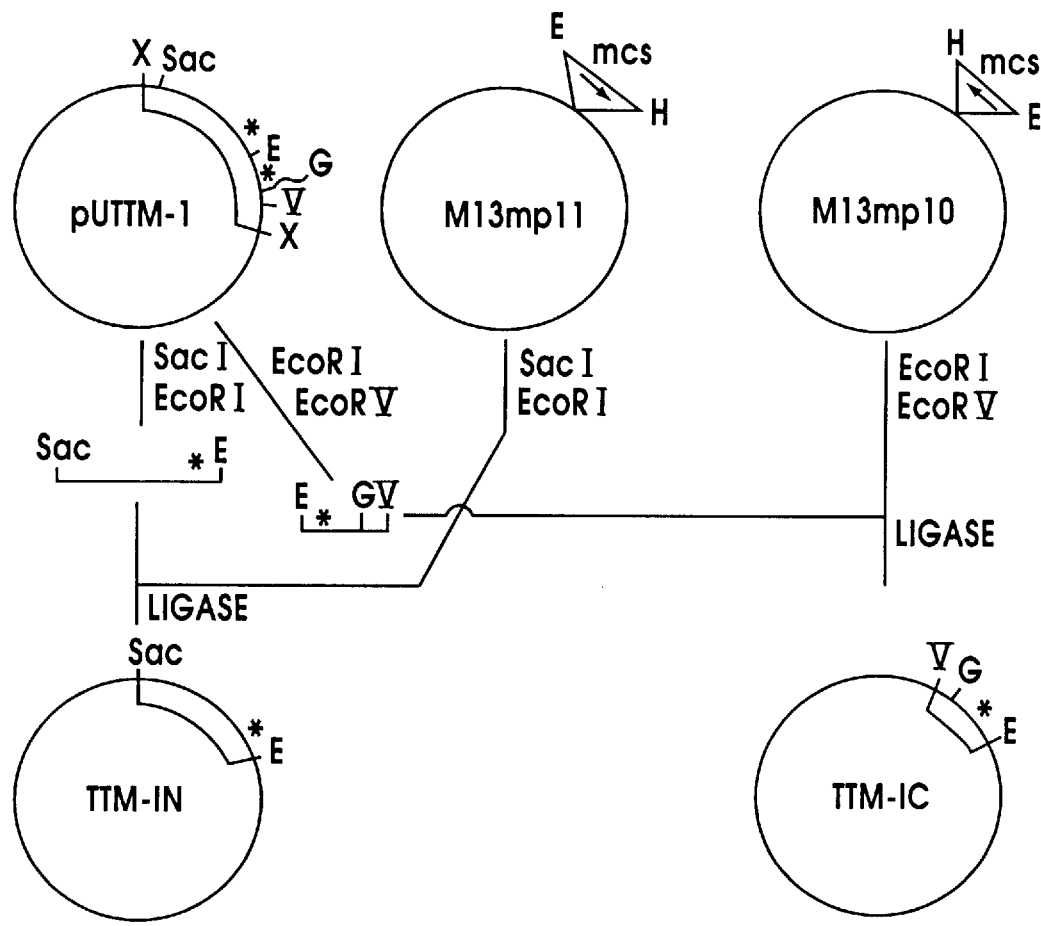
FIG. 2 shows the procedure for construction of TTM-1N and TTM-1C.

(4) Production of TTM-1' modified (TGA→TGG) not to read TTM-1-encoding protein TTMG-1 by TGA as translation termination codon (see FIG. 2)

After pUTTM-1 of (3) described above was digested with restriction enzymes SacI and EcoRI and the digestion product was then subjected to 0.8% low melting agarose gel electrophoresis. The 1.1 kbp fragment containing the 5'-end of TTM-1 was recovered by treating with phenol-chloroform and precipitating with ethanol. The fragment was ligated with the fragment obtained by digestion of M13mp11 phage with SacI and EcoRI. The ligation reaction solution was mixed at m.o.i. of 0.1 with a solution obtained by culturing E. coli TG1 at 37° C. for 24 hours, adding IPTG thereto in a final concentration of 100 mM and further supplementing IPTG in a X-gal concentration of 2%. The resulting mixture was inoculated on soft agar for solidification. Incubation was then performed at 37° C. for 24 hours. Among the phage plaques formed, recombinant phage TTM-1N containing 1.1 kbp DNA of TTM-1 was collected from the phage in which the color did not change to blue.

Likewise, pUTTM-1 was digested with EcoRI and EcoRV. After 0.8% low melting agarose gel electrophoresis, the 0.4 kbp fragment containing the 3'-end of TTM-1 was recovered from the gel. A phenol-chloroform treatment followed by ethanol precipitation gave M13mp10 phage. M13mp10 phage was ligated with the fragment obtained by digestion with EcoRI and EcoRV using ligase. The reaction solution was treated as in the cloning of the 1.1 kbp DNA. Recombinant phage TTM-1C containing 0.4 kbp DNA of TTM-1 was thus obtained.

(5) Preparation of single stranded DNA from each recombinant phage

The two recombinant phage obtained in (4) described above were added at m.o.i. of 0.1, respectively, to E. coli TG1 proliferated at 37° C. in 100 ml of 2×YT medium. After shake culture at 37° C. for 5 hours, centrifugation was performed at 5000G for 30 minutes to obtain the cell-free supernatant. A 0.2-fold volume of polyethylene glycol/sodium chloride mixture (20% polyethylene glycol #6000, 2.5M NaCl) was added to the supernatant. After settlement at 4° C. for an hour, the mixture was centrifuged at 5000G for 20 minutes to recover the precipitates. The precipitates were dissolved in 500 μl of TE buffer (10 mM Tris-HCl, 1 mM EDTA, pH 8.0). After extraction with phenol-chloroform, single stranded DNA of each recombinant phage was recovered by ethanol precipitation.

(6) Construction of site-specific mutated plasmids using artificially synthesized oligonucleotide as a primer The thus obtained DNA has TGA at the middle of the sequence. This TGA sequence is recognized as a termination codon in a normal cell so that the TGA sequence does not translate the sequence added there-after. Therefore, in order to translate the TGA portion as methionine, the basic adenine which corresponds to the third nucleotide in codon NNN must be modified to guanine. Thus, the following two oligonucleotides were synthesized.
(SEQ ID NO: 24)
3'-TACGTTCTTCCTGGCAAACCTTACCACTACTT-5'
(SEQ ID NO: 25) 3'-CTACAAAGAACCTAAATATCA-5'

The oligonucleotide shown by (SEQ ID NO: 24) is annealed to single stranded DNA of TTM-1N and the oligonucleotide shown by (SEQ ID NO: 25) to single stranded DNA of TTM-1C to cause the desired mutation by the method of Frits Eckstein et al. (Nucleic Acid Research, 8749–8764, 1985). The thus obtained recombinant phages were named TTM-1N' and TTM-1C', respectively. The TTM-1N' and TTM-1C' phage DNAs thus obtained were digested with restriction enzymes SacI-EcoRI and EcoRI-BglII, respectively. By 0.8% low melting agarose gel electrophoresis, the fragments of 1.1 kbp and 0.4 kbp were extracted from the agarose gel and recovered by ethanol precipitation. On the other hand, plasmid pUTTM-1 was also digested with SacI-BglII. The 4.8 kbp fragment bearing a vector was extracted by 0.8% low melting agarose gel electrophoresis and recovered by ethanol precipitation. The thus obtained three fragments were ligated by ligase and competent *E. coli* TG1 strain was transformed to obtain plasmid pUTTM-1' bearing TTM-1' with mutagenesis at the desired site thereof. The nucleotide sequence of TTM-1' is as shown by SEQ ID NO: 14 according to the Dideoxy method by Sanger et al. (Proc. Natl. Acad. Sci. USA, 74, 5463 (1977)). The nucleotide sequence is substantially the same as the 40 kilodalton TTM-1 polypeptide of *M. gallisepticum*.

Reference Example 2
Construction of vector pNZ1729R for insertion

The EcoRI fragment (about 7.3 kbp) of NP strain was inserted into pUC18 at the EcoRI digestion site (terminus at the multi-cloning site) to obtain plasmid pNZ133 (about 10.0 kbp). From the plasmid the HpaI-SpeI fragment (about 3.0 kbp fragment derived from NP strain) was excised out (SEQ ID NO: 11) and (SEQ ID NO: 12) (bearing FPV promoter of 17 bases and linked to a translation initiation codon for lacZ) were annealed to double strands. (SEQ ID NO: 13) annealed to the lacz gene (derived from pMC1871 an pMA001, Sirakawa et al., Gene, 28, 127–132, 1984) and (SEQ ID NO: 14), (SEQ ID NO: 15) and (SEQ ID NO: 16), (SEQ ID NO: 17) and (SEQ ID NO: 18), (SEQ ID NO: 19) and (SEQ ID NO: 20), were ligated with each other (which contains a modified synthetic promoter of poxvirus shown by nucleotide sequence: (SEQ ID NO: 51) T T T T T T T T T T T T T T T T T T T T T G G C A T A T A A A T A A T A A A T A C A A T A A T T A A T T A C G C G T A A A A A T T G A A A A A C T A T T C T A A T T T A T T G C A C T C from the next T of AGC at the 5' end of (SEQ ID NO: 12) to C before G of Sequence No. 5 at the 3' end, and further linked to the multi-cloning site and poxvirus initial transcription termination signal on the both directions (SEQ ID NO: 21) (Yuen et al., Proc. Natl. Acad. Sci., USA, 88, 6417–6421, 1989) thereby to obtain the EcoRI-HindIII fragment (about 3.5 kbp). The EcoRI-HindIII fragment was inserted into pNZ133SR to construct plasmid pNZ1729R.

Figure 3:
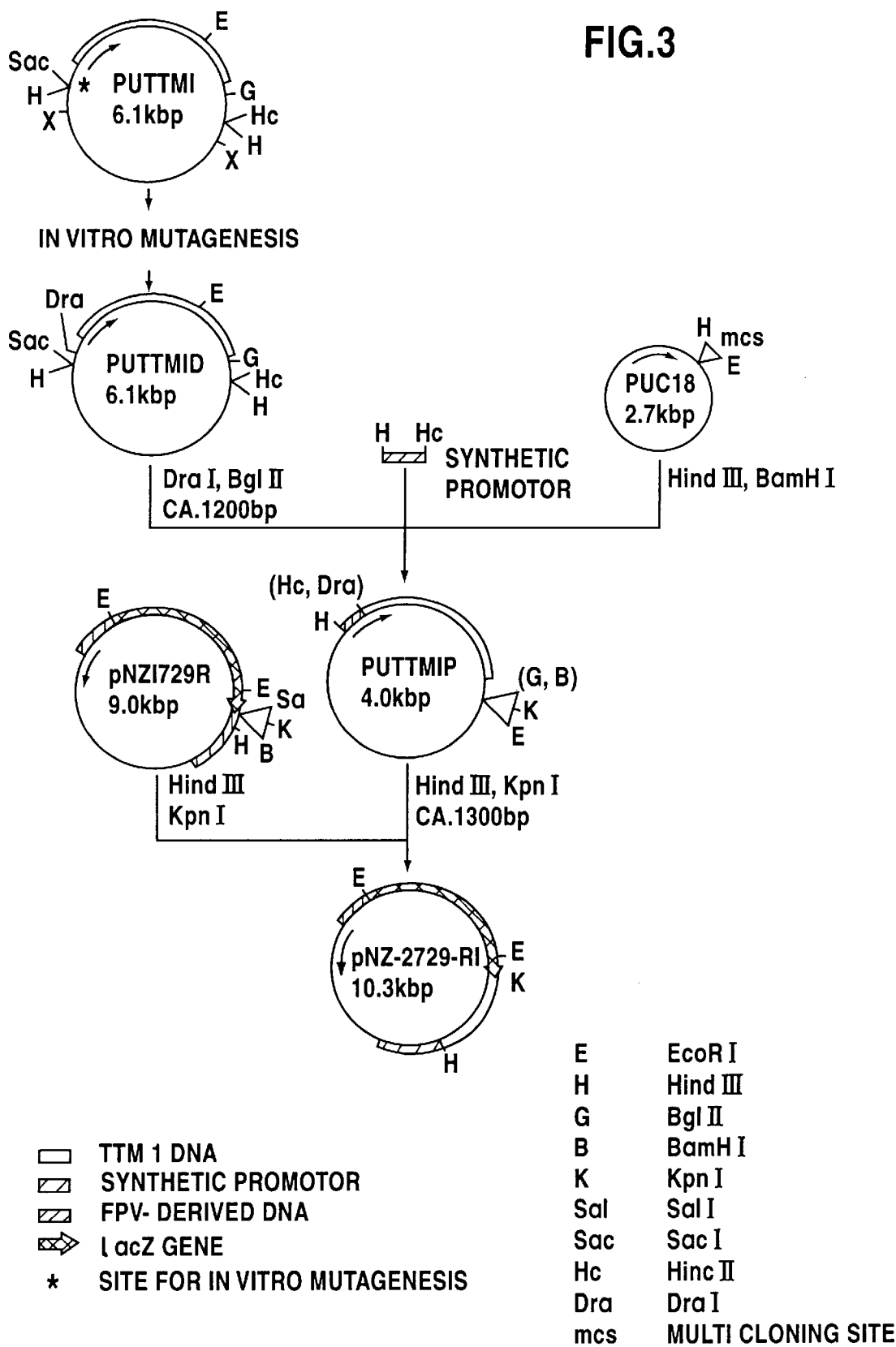
FIG. 3 shows the procedure for constructing pNZ7929-R1.
Figure 4:
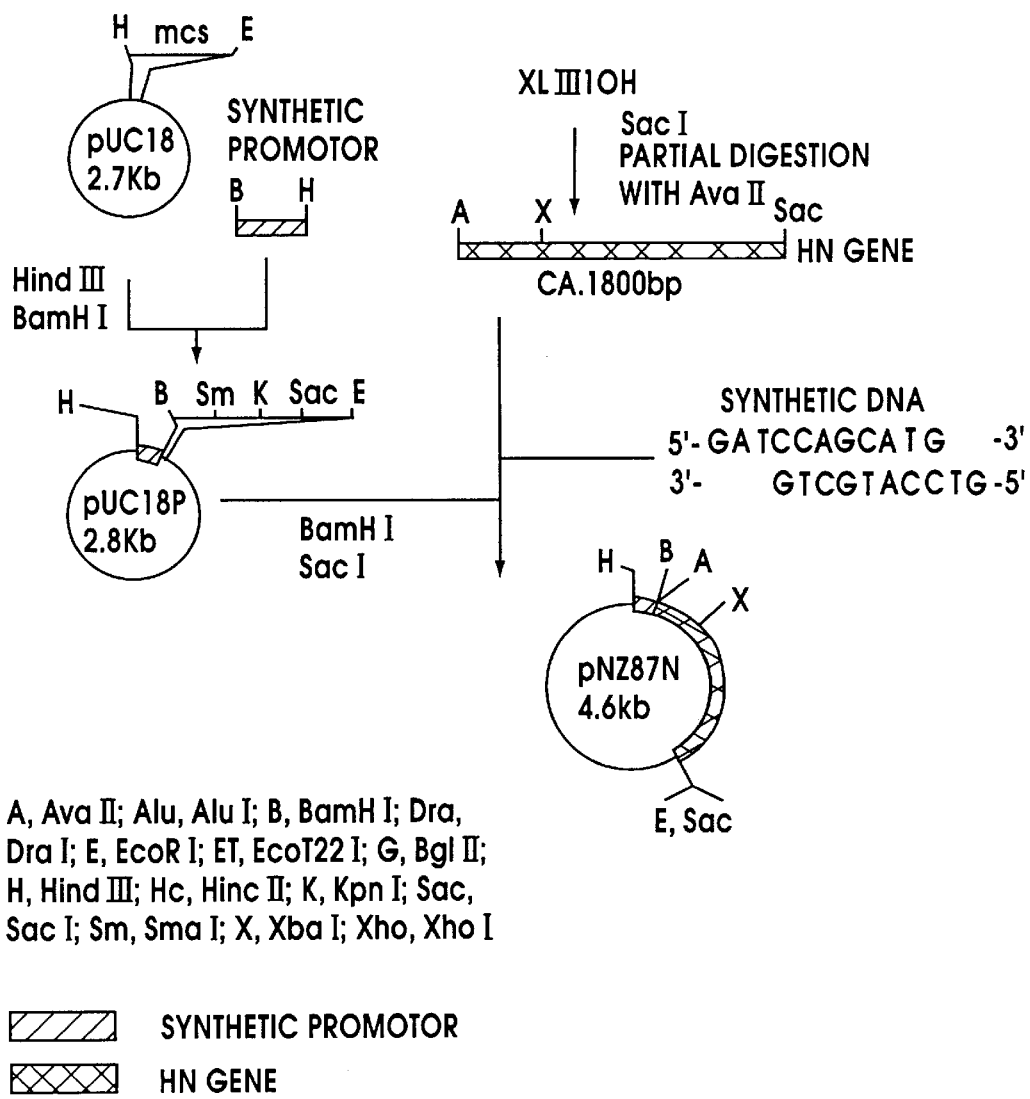
FIG. 4 shows the procedure for constructing pNZ87N (SEQ. ID NOS 31 and 32, respectively).

Example 1
Construction of plasmid pNZ7929-R1 for recombination (see FIG. 3)

(1) Construction of plasmid pUTTM1P having ligated a synthetic promoter with TTM-1' gene In order to form the restriction enzyme DraI digestion site upstream ATG corresponding to initiation codon of TTM-1' protein in plasmid pUTTM1' (see WO 93/24646) containing the full length TTM-1' DNA obtained in Reference Example 1, the following oligonucleotide was firstly prepared.
(SEQ ID NO: 26) 3'-TATAGAATTAAATTTTACTTATTC-5'

Next, after pUTTM-1' was digested with restriction enzymes SacI and EcoRI, the fragment of about 2300 bp was recovered and then ligated with the fragment obtained by digestion of M13mp10 with SacI and EcoRI to obtain recombinant phage TTM-1'. The oligonucleotide described above was annealed to single stranded TTM-1' to cause the desired variation by the method of Frits Eckstein et al. This recombinant phage DNA variant was digested with restriction enzymes SacI and EcoRI. The fragment of about 2300 bp was recovered and cloned to the vector-bearing fragment obtained by digestion of pUTTM-1' again with SacI and EcoRI to obtain pUTTM1D.

A synthetic promoter was prepared by synthesizing DNAs of (SEQ ID NO: 27) and (SEQ ID NO: 28) followed by annealing, whereby the digestion sites with restriction enzymes HindIII and HincII at the end.

(SEQ ID NO:27) 5'-AGCTTTTTTTTTTTTTTTTTTTTGGCATATAAATAATAAATACAATAATTAATTACGCGTAAAAATT.
(SEQ ID NO:28) 3'-    AAAAAAAAAAAAAAAAAAAAACCGTATATTTATTATTTATGTTATTAATTAATGCGCATTTTTAA
           HindIII GAAAAACTATTCTAATTTATTGCACTCGTC-3'
CTTTTTGATAAGATTAAATAACGTGAGCAG-5'
                                                   HincII and rendered blunt end by Klenow fragment. Furthermore, the EcoRI-HindIII fragment (multi-cloning site of 52 bp) was removed from pUC18 and rendered blunt end by Klenow fragment. The two fragments were ligated with each other to form a plasmid. After removing the EcoRV site in the HpaI-SpeI fragment, the EcoRI-HindIII fragment (multi-cloning site of 52 bp) of pUC18 is inserted therein using HindIII linker (5'-CAAGCTTG-3') and EcoRI linker (5'-GGAATTCC-3') to construct plasmid pNZ133SR.

Finally, the 1200 bp fragment obtained by digestion of pUTTM1D with restriction enzymes DraI and BglII was ligated with the synthetic promoter described above and the fragment obtained by digestion of pUC18 with HindIII and BamHI to give plasmid pUTTM1P of about 4.0 kbp.

(2) Construction of pNZ7929R1

After plasmid pUTTM1p obtained in (1) was digested with restriction enzymes HindIII and KpnI, the fragment of about 1300 bp was recovered. Next, vector pNZ1729R (EP-A-0520753) for FPV recombination obtained lo in Reference Example 2 was digested with restriction enzymes HindIII and KpnI. The two fragments were ligated with each other to obtain the desired vector pNZ7929-R1 (about 10.3 kbp) for recombination.

(3) Construction of recombinant FPV fNZ7929-R11 and purification thereof

NP strain, which is a fowlpox live vaccine strain, was infected to monolayered CEF at m.o.i.=0.1. Three hours after, these cells were peeled apart from the monolayer by a treatment with trypsin to form a cell suspension. After $2 \times 10^7$ cells in the suspension were mixed with 10 µg of plasmid pNZ7929-R1 for recombination, the mixture was suspended in Saline G (0.14M NaCl, 0.5 mM KCl, 1.1 mM $Na_2HPO_4$, 1.5 mM $KH_2PO_4$, 0.5 mM $MgCl_2$ $6H_2O$, 0.011% glucose). The suspension was subjected to electrophorasis under conditions of 3.0 kV $cm^{-1}$, 0.4 msec and 25° C., using Gene Pulser (Bio-Rad) at room temperature. The plasmid-infected cells were then cultured at 37° C. for 72 hours. The cells were lysed by freeze and thaw 3 times to recover viruses containing the recombinant virus.

The recombinant virus recovered was selected as follows. The recovered viral solution was infected to monolayered CEF and 10 ml of agar solution containing growth medium was overlaid thereon. After agar was solidified at room temperature, incubation was performed at 37° C. until plaques of FPV appeared. Then agar medium containing Bluo gal in a concentration of 200 μg/ml was overlaid on the agar followed by incubation at 37° C. for further 48 hours. Among all of the plaques, about 1% of the plaques were colored blue. These blue plaques were isolated and recovered. By the same procedures, isolation and recovery were repeated to purify the virus until all the plaques were stained to blue with Bluo gal. In general, the repeated procedures were terminated by 3 to 4 times. The purified virus was named fNZ7929-R1. In fNZ7929-R1, each position of the DNA inserted was confirmed by dot blotting hybridization and Southern blotting hybridization.

Example 2

Obtaining of 70K Protein DNA (1) Preparation of *Mycoplasma gallisepticum* genomic DNA Using *Mycoplasma gallisepticum* S6 strain, 200 μg of *Mycoplasma gallisepticum* DNA was obtained in a manner similar to Reference Example 1 (1) described above.

(2) Preparation of genomic DNA library

After 4 units of restriction enzyme AluI was added to 40 μg of *Mycoplasma gallisepticum* genomic DNA obtained in (1), incubation was conducted at 37° C. for 10 minutes for partial digestion. The partially digested genomic DNA was subjected to 0.8% low melting agarose gel electrophoresis. The DNA fragment having a strand length of approximately 1.0 kbp to 4.0 kbp was recovered from the gel. The DNA fragment was treated with phenol and then precipitated with ethanol to give 4 μg of the DNA fragment partially digested with AluI.

S-Adenosyl-L-methionine was added to 1.2 μg of the AluI-partially digested-DNA fragment in a final concentration of 80 μM and 20 units of EcoRI methylase was further added thereto to methylate the deoxyadenosine site in the EcoRI recognition sequence, thereby to render the sequence non-sensitive to EcoRI. EcoRI linker was ligated with this DNA fragment using ligase. The ligation product was then mixed with the EcoRI digestion fragment of λgt11DNA to ligate with each other by ligase. The reaction solution was used to effect in vitro packaging in a conventional manner (DNA Cloning, Vol. 1, A Practical Approach, edited by D. M. Glover). The resulting product was transfected to *Escherichia coli* Y1088 strain (Amersham) followed by incubation at 37° C. for 12 hours in LB agar medium containing 0.003% of 5-bromo-4-chloro-3-indolyl-β-D-galactopyranoside and 0.03 mM isopropylthio-β-D-galactopyranoside. Among the plaques formed, a library size was estimated by the count of white plaques to prepare DNA library of $10^6$ pfu (plaque forming unit).

(3) Immuno-screening of genomic DNA library

The phage obtained from the DNA library prepared in (2) was added to a suspension of *Escherichia coli* Y1090 strain (Amersham) in an aqueous solution of 10 mM $MgSO_4$ to form 500 to 1000 plaques on one plate of 8 cmφ to effect adsorption for 15 minutes. Furthermore 2.5 ml of LB soft agar medium warmed to 45° C. was added and overlaid on the LB agar medium followed by incubation at 42° C. for 3 to 4 hours. A nylon membrane filter was immersed in 10 mM of IPTG aqueous solution, air-dried and then overlaid on the plate described above followed by incubation at 37° C. for further 2 to 3 hours. After the incubation, the nylon membrane filter was peeled apart from the plate and washed with TBS (50 mM Tris-HCl, pH 8.0, 150 mM NaCl). The filter was immersed in 2% skimmed milk-containing TBS for 30 minutes and then treated for an hour with anti-Mycoplasma chicken serum diluted with TBS to 500-fold. Thereafter, the filter was immersed in TBS for 15 minutes to wash the filter. The filter was further washed by immersing in TBS containing 0.05% of a surfactant (Tween 20) for 10 to 15 minutes. This step was repeated 4 to 5 times. Then the filter was treated with biotinylated antibody against chicken IgG for 60 minutes. After treating with a secondary antibody, the filter was washed with PBS containing 0.05% of Tween 20 5 to 6 times and then treated for 60 minutes by immersing in horse radish peroxidase-avidin D solution. After the treatment, the filter washed with PBS containing 0.05% of Tween 20 5 to 6 times and then washed with 10 mM Tris-HCl, pH 8.0. Then, the filter was immersed in a buffer containing 4-chloronaphthol and hydrogen peroxide. By a series of these operations, only the plaques that expressed an antigenic protein originating in *Mycoplasma gallisepticum* were colored purple.

By the aforesaid immuno-screening of about $5\times10^4$ plaques, 50 positive plaques were obtained.

(4) Production of immuno-positive recombinant λgt11phage DNA

*Escherichia coli* Y1090 strain was incubated at 37° C. for 12 hours in LB medium supplemented with 50 μg/ml ampicillin. The culture broth was added to a 10-fold amount of LB medium containing mM $MgSO_4$. Then, recombinant λgt11 phage which was obtained in (3) and became positive by immuno-screening was added to the medium at m.o.i.= 0.05, followed by incubation at 37° C. for 5 to 10 hours. After lysis of *Escherichia coli*, centrifugation was carried out at 8,000 rpm for 10 minutes to obtain the supernatant. To the supernatant were added an equal volume of TM buffer (50 mM Tris-HCl, pH 7.4, 10 mM $MgSO_4$) and DNase I in a concentration of 0.016 mg/ml, followed by incubation for 15 minutes. After NaCl and polyethylene glycol (PEG 6000) were added to the culture broth in concentrations of 0.5M and 0.1 g/ml, respectively, the mixture was shaken at 0° C. for 15 minutes. After centrifugation at 10,000 rpm for 10 minutes, the supernatant was removed. The resulting pellets were dissolved in a 1/100 volume of TM buffer and an equal volume of chloroform was added thereto followed by vigorous stirring. By centrifugation at 15,000 rpm for 10 minutes, recombinant λgt11 phage was collected in the aqueous phase to obtain the phage solution.

EDTA, SDS and pronase E were added to the phage solution in final concentrations of 0.025M, 1% and 1 mg/ml, respectively. After incubation at 37° C. for 4 hours, the solution was subjected to phenol extraction and ethanol precipitation to give λgt11 phage DNA containing the cloned antigenic DNA (M-81).

(5) Construction of recombinant plasmid (pM-81)

The recombinant λgt11 phage DNA obtained in (4) was digested with restriction enzyme EcoRI, the digestion product was subjected to 0.8% low melting agarose gel electrophoresis. The genomic DNA fragment of *Mycoplasma gallisepticum* inserted into the genomic DNA of λgt11 phage at the cloning site showed a strand length of about 2.8 kbp. This DNA fragment was extracted from the agarose gel and then with phenol-chloroform (1:1) and recovered by ethanol precipitation. On the other hand, after plasmid pUC18 was digested with EcoRI, the digested pUC18 was extracted with phenol-chloroform and recovered by ethanol precipitation, in a similar manner. Then, the phosphate at the 5' end was removed by an alkaline phosphatase treatment. After pUC18 DNA was again extracted with phenol-chloroform, DNA was recovered by ethanol precipitation.

The digested pUC18 was ligated with the EcoRI digestion product (about 0.8 kbp) derived from *Mycoplasma gallisepticum* using ligase. Competent *Escherichia coli* TG1 strain was transformed with the ligation product. The transformants were cultured at 37° C. for 15 hours in LB agar medium supplemented with 0.003% of 5-bromo-4-chloro-3-indolyl-β-D-galactopyranoside, 0.03 mM of isopropylthio-β-D-galactopyranoside and 40 μg/ml of ampicillin. Among the transformed *E. coli* grown on the agar medium, white colonies were cultured at 37° C. for 15 hours in 40 μg/ml ampicillin-supplemented LB liquid medium and plasmid was extracted by the method of Birnboin & Doly [Nuc. Acid Res., 7, 1513~(1979)]. After digestion with EcoRI, the recombinant plasmid containing the same length of DNA fragment as that of the original EcoRI fragment derived from *Mycoplasma gallisepticum* was detected by 0.8% low melting agarose electrophoresis; this plasmid was named pM-81.

(6) Genomic Southern hybridization of Mycoplasma gallisepticum using M-81 DNA as a probe After 1 μg of pM81 obtained in (5) described above was digested with EcoRI and HindIII, the digestion product was subjected to 0.6% low melting agarose gel electrophoresis. After the electrophoresis, the gel was immersed in an alkaline denaturation solution (0.5M NaOH, 1.5M NaCl) for 10 minutes to denature DNA. The gel was then immersed in a neutralization solution (3M sodium acetate, pH 5.5) for 10 minutes for neutralization and then transferred onto a nylon membrane in 6-fold SSC solution (0.7M NaCl, 0.07M sodium citrate, pH 7.5). After air-drying, the nylon membrane was baked at 80° C. for 2 hours and 4-fold SET (0.6M NaCl, 0.08M Tris-HCl, 4 mM EDTA, pH 7.8)-10-fold Denhardt-0.1% SDS-0.1% $Na_4P_2O_7$-50 μg/ml of denatured salmon sperm DNA and pM-81 (M-81 gene is contained in this plasmid) labelled in a conventional manner was added thereto to perform hybridization at 68° C. for 14 hours. The nylon membrane was overlaid on an X ray film. It was confirmed by autoradiography that M-81 was hybridized to the about 5.0 kbp fragment of *Mycoplasma gallisepticum.*

(7) Cloning of EcoRI and HindIII-digested fragment of about 5.0 kbp to pUC19 and colony hybridization After 4 μg of the *Mycoplasma gallisepticum* DNA obtained in (6) described above was digested with EcoRI and HindIII, the digestion product was subjected to 0.6% low melting agarose gel electrophoresis to recover the fragment of about 5.5 kbp. The fragment was ligated with pUC-19 cleaved by digestion with EcoRI and HindIII using ligase. Competent *Escherichia coli* TG1 strain was transformed with the ligation product. The transformants were cultured at 37° C. for 15 hours in LB agar medium supplemented with 0.003% of 5-bromo-4-chloro-3-indolyl-β-D-galactopyranoside, 0.03 mM of isopropylthio-β-D-galactopyranoside and 40 μg/ml of ampicillin. White colonies grown on the medium were transferred onto a nylon membrane and hybridization was carried out in a manner similar to (2) described above. It was confirmed by autoradiography that cloning was effected and this plasmid was named pUM-81.

(8) Sequence analysis of pUM-81 insert DNA

The sequence of about 5.0 kbp fragment inserted into pUM-81 prepared in (7) above was analyzed by the dideoxy method by Sanger et al.

The restriction enzyme map of the open reading frame (hereinafter abbreviated as ORF) present in this fragment is shown in FIG. 1. The nucleotide sequence of this ORF and the amino acid sequence deduced therefrom are shown by SEQ ID NO: 1. The polypeptide deduced from this ORF was named TM-81 polypeptide.

Example 3

Construction of recombinant FPV bearing hybrid DNA in which TTM-1' protein DNA was ligated downstream the signal membrane anchor DNA (1) Cloning of the synthetic promoter to pUC18 (see FIG. 4)

The following synthetic promoters bearing the HindIII and BamHI restriction enzyme sites at both ends were synthesized.

```
                HindIII
(SEQ ID NO:29)  5'- AGCTTTTTTTTTTTTTTTTTTTTTGGCATATAAATAATAAATACAATAATTAATTACGC
(SEQ ID NO:30)  3'-         AAAAAAAAAAAAAAAAAAAAACCGTATATTTATTATTTATGTTATTAATTAATGCG
                GTAAAAATTGAAAAACTATTCTAATTTATTGCACTCG                -3'
                CATTTTTAACTTTTTGATAAGATTAAATAACGTGAGCCTAG            -5'
                                                     BamHI
```

This synthetic DNA was ligated with the digestion fragment of PUC18 with HindIII and BamHI to obtain plasmid of about 2.8 kbp named PUC18P.

(2) Ligation of a gene encoding HN protein of NDV with the synthetic promoter (see FIG. 4)

After plasmid XLIII-10H bearing HN gene of NDV was fully digested with SacI, the digestion product was then partially digested with AvaII. The fragment of about 1800 bp was recovered by 0.8% low melting agarose gel electrophoresis. In order to form the BamHI cleavage site at the AvaII site of this fragment, the following DNA was synthesized.

|  | BamHI | AvaII |
|---|---|---|
| (SEQ ID NO: 31) | 5' - GATCCAGCATG - 3' | |
| (SEQ ID NO: 32) | 3' -   GTCGTACCTG - 5' | |

Three of the synthetic DNA, the HN-bearing DNA fragment of about 1800 bp and the fragment containing the synthetic promoter recovered by 2.0% low melting agarose gel electrophoresis after full digestion of pUC18P with BamHI and SacI were ligated by ligase and these three fragments-ligated plasmid was extracted. The resulting plasmid of about 4.6 kbp was named pNZ87N.

Figure 5:
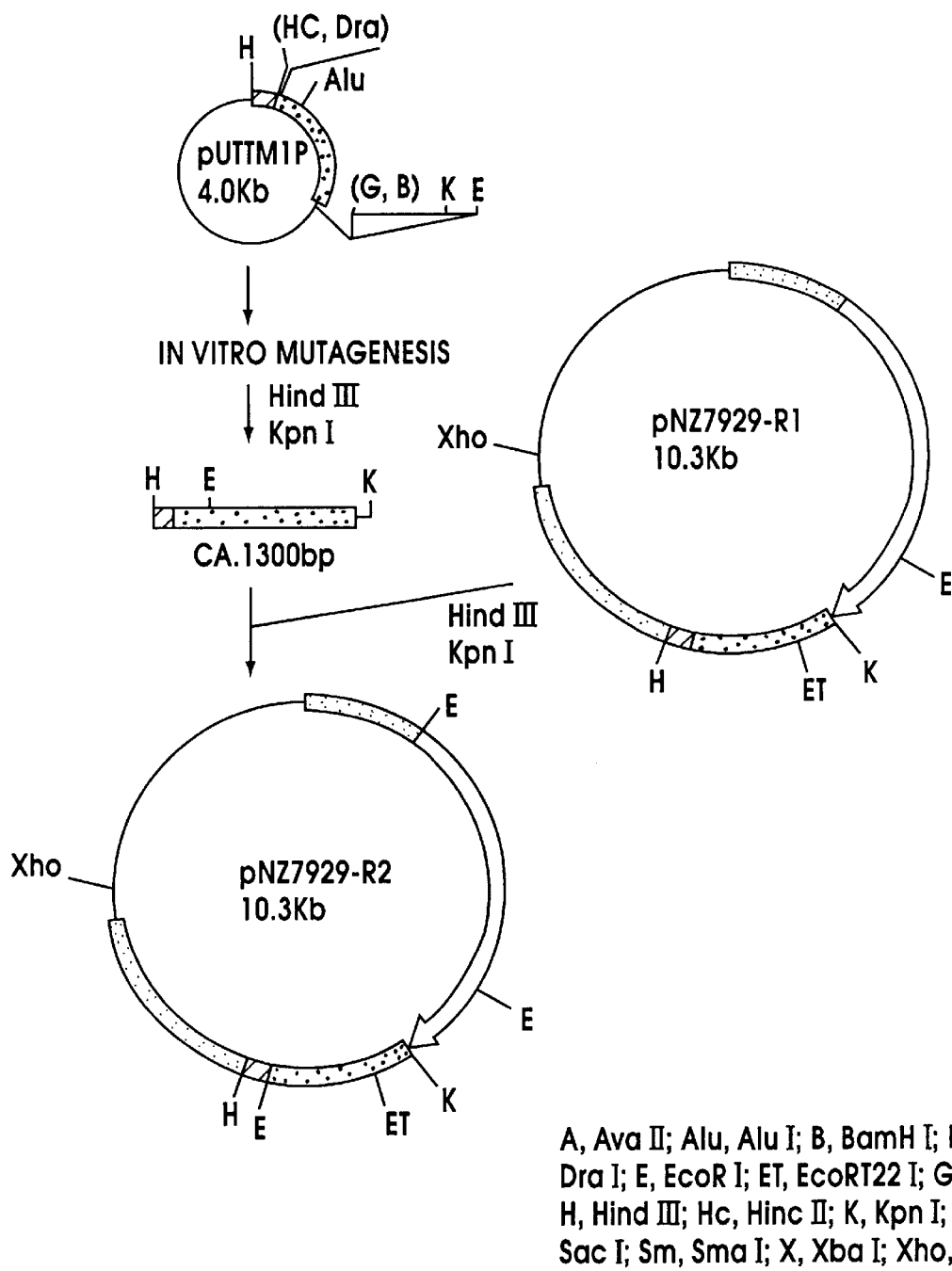
FIG. 5 shows the procedure for constructing pNZ7929-R2.

(3) Change of the AluI cleavage site of pNZ7929-R1 into the EcoRI cleavage site (see FIGS. 3 and 5)

In order to change the restriction enzyme AluI cleavage site in the 279 nucleotide portion of SEQ ID NO: 3 into the EcoRI cleavage site, the following oligonucleotide was synthesized.

(SEQ ID NO: 33) 5'-GGGATTTCGAATTCTATGTCT-3'

After pUTTM1P was digested with HindIII and KpnI, the fragment of about 1300 bp and ligated with the fragment obtained by digestion of M13mp10 with HindIII and KpnI to obtain the single stranded recombinant phage. The oligonucleotide described above was annealed to the single stranded recombinant phage to cause the desired mutation by the method of Frits Eckstein et al. After the recombinant phage DNA mutant was digested with restriction enzymes HindIII and KpnI, the fragment of about 1300 bp was recovered and ligated with the fragment obtained by digestion of pNZ1729R with restriction enzymes HindIII and KpnI using ligase to obtain plasmid pNZ7929-R2 (about 10.3 kbp) with the AluI cleavage site of pNZ7929-R1 being changed into the EcoRI cleavage site.

Figure 6A:
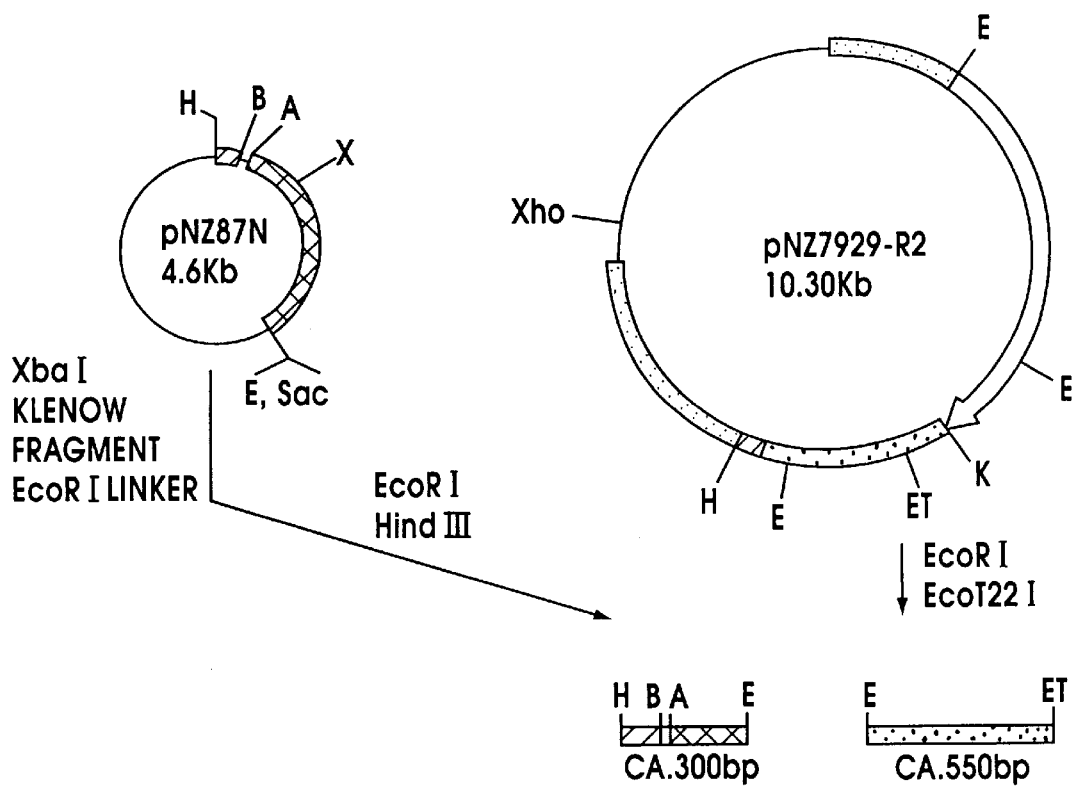
FIG. 6(A) and (B) show the procedure for constructing pNZ2929XM1.
Figure 6B:
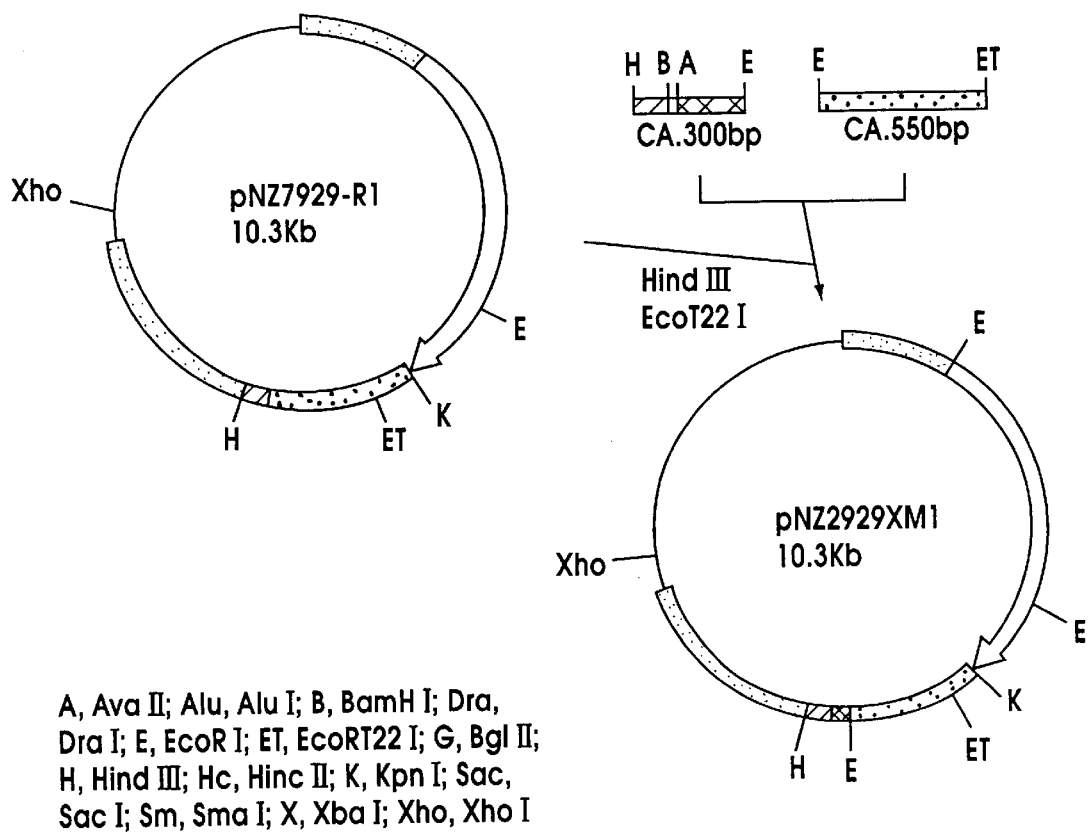

(4) Construction of plasmid pNZ2929XM1 for recombinant FPV (see FIG. 6(A) and 6(B))

Firstly pNZ87N was fully digested with restriction enzyme XbaI and the cleavage site was rendered blunt by Klenow fragment. Then EcoRI linker (5'-GGAATTCC-3') was added to and ligated with the digestion product using ligase. The plasmid was digested with EcoRI and HindIII. The fragment of about 300 bp was recovered by 1.2% low melting agarose gel electrophoresis. Next, pNZ7929R2 was digested with restriction enzyme EcoT22I and then partially digested with EcoRI. The fragment of about 550 bp which is a part of TTM-1 DNA was recovered by 0.8% low melting agarose gel electrophoresis. Furthermore, pNZ7929RI was digested with restriction enzymes EcoT22I and HindIII and the fragment of about 9.4 kbp was recovered by 8% low melting agarose gel electrophoresis. These fragments were ligated by ligase and the three fragments-ligated plasmid was extracted. The plasmid of about 10.3 kbp was named pNZ2929XM1.

(5) Construction and purification of recombinant FPV fNZ2929XM1

Construction and purification were carried out in a manner similar to Example 1 (3). The purified virus was named fNZ2929-XM1. By dot blotting hybridization and Southern blot hybridization, the location of each DNA inserted was confirmed in fNZ2929-XM1.

Example 4

Expression of TTM-1 polypeptide in cells infected with fNZ7929-R1 and fNZ2929XM1

In order to confirm that fNZ7929-R1 and fNZ2929XM1 express TTM-1 polypeptide in infected cells, immunofluorescent antibody technique using antisera against *Mycoplasma gallisepticum* S6 was employed. fN7929-R1 and fNZ2929XM1 were infected to CEF and incubation was carried out at 37° C. until plaques appeared. After fixing with cold acetone, chicken antisera (anti-S6) immunized with *Mycoplasma gallisepticum* S6 strain or *Mycoplasma gallisepticum* S6-infected chicken sera (S6 infected) and TTM-1 polypeptide-immunized chicken anti-sera (anti-TTMG-1) diluted as a primary antibody to 100 to 1000-fold were reacted. These culture cells were further reacted with anti-chicken immunoglobulin bound to a fluorescent substance (FITC) and the non-specific reaction portion was washed out. Then, microscopic observation was made under the excited fluorescent wave-length light. With respect to the infected cells where no acetone fixing was performed (namely, unfixed cells), the reactivity was likewise examined. Using FPV-NP strain and fNZ2337 (Japanese Patent Application Laid-Open No. 1-157381) as viruses for control, Newcastle disease virus-immunized chicken sera (anti-NDV) and SPF chicken sera (SPF) were used in 1000-fold as primary antibody for control. The reactivity is shown in Table 1.

TABLE 1

Reactivity of recombinant virus-infected CEF to various antisera

| Infected virus (acetone fixation) | Reactivity to primary antibody: anti-S6 | Infected S6 | anti-TTM-1 | anti-NDVSPF | |
|---|---|---|---|---|---|
| fNZ2929XM1 | | | | | |
| (acetone-fixed) | ++ | ++ | ++ | – | – |
| (non-fixed) | + | + | + | – | – |
| fNZ7929-R1 | | | | | |
| (acetone-fixed) | + | + | | – | – |
| (non-fixed) | ± | ± | ± | – | – |
| fNZ2337 | | | | | |
| (acetone-fixed) | – | – | – | + | – |
| (non-fixed) | – | – | – | + | – |
| NP | | | | | |
| (acetone-fixed) | – | – | – | – | – |
| (non-fixed) | – | – | – | – | – |
| None | | | | | |
| (acetone-fixed) | – | – | – | – | – |
| (non-fixed) | – | – | – | – | – |

++: strongly reacted
+: reacted
±: weakly reacted
–: not reacted

The results reveal that the cells infected with the recombinant viruses fNZ7929-R1 and fNZ2929XM1 of the present invention are reactive with anti-S6, S6 infection and anti-TTM-1; and that fNZ7929-R1 are reactive with anti-S6, S6 infection and anti-TTMG-1 also in non-fixed completed cells. This indicates that fNZ2929XM1 not only expresses TTMG-1 polypeptide in the infected cells but also exhibits TTM-1 polypeptide on the surface of the infected cells.

Example 5

Antibody inducing ability of recombinant FPV inoculated to chickens

After fNZ7929-R1 and fNZ2929XM1 were cultured in CEF at 37° C. for 48 hours, the procedure of freezing and thawing was repeated twice to recover the cell suspension. The cell suspension was adjusted to have a virus titer of $10^6$ pfu/ml and then inoculated to SPF chick (Line M, Nippon Seibutsu Kagaku Kenkyusho) of 7 days old at the right wing web in a dose of 10 μl. After the inoculation, generation of the pock was observed. Two weeks after the inoculation, sera were collected. The antibody titer of the sera collected was determined by ELISA. The purified TTM-1 polypeptide was dissolved in bicarbonate buffer in a concentration of 1 μg/well. After adsorbing to a 96 well microtiter plate, blocking was performed with skimmed milk to prevent the following non-specific adsorption. Next, a dilution of the sample serum was charged in each well and then horse radish peroxide-bound anti-chick immunoglobulin antibody (rabbit antibody) was added thereto as a secondary antibody. After thoroughly washing, 2,2'-azinodiethylbenzothiazoline sulfonate was added to the mixture as a substrate and a relative dilution magnification of the antibody was measured with an immuno-reader in terms of absorbance at a wavelength of 405 nm. As a primary antibody for control, anti-TTM-1 polypeptide chicken serum was used. The results are shown in Table 2.

TABLE 2

Antibody titer of fNZ2929XM1-inoculated chick to TTM-1 polypeptide

| Inoculated virus | Antibody titer to anti-TTM-1 polypeptide (dilution magnification)* |
|---|---|
| fNZ2929XM1 | 256 |
| fNZ7929-R1 | 32 |
| NP | 1 |
| ** | 1 |
| anti-TTM-1 polypeptide | 256 |

*dilution magnification when SPF chicken serum dilution is as 1
**not inoculated The results reveal that both fNZ2929XM1 and fNZ2929-R1 which are the recombinant viruses of the present invention, can induce anti-TTM-1 polypeptide antibody and can be used as a vaccine for effectively preventing fowlpox and *M digested with HindIII and PstI was ligated with the fragment obtained by digesting pUC18 with HindIII and PstI, using ligase. The resulting plasmid was extracted and named pUC18R (about 3 kbp). The fragment of about 2.5 kbp obtained by digestion of pUC19XL with HindIII and XhoI, the fragment of 180 bp obtained by digestion of pUC18R with HindIII and SpeI, and the fragment of 1.1 kbp obtained by digestion of pUC18X with XbaI and XhoI were subjected to agarose gel electrophoresis, respectively, and then recovered. These fragments were ligated using ligase. The resulting plasmid was extracted and named pTM67 (about 3.7 kbp).

Figure 9A:
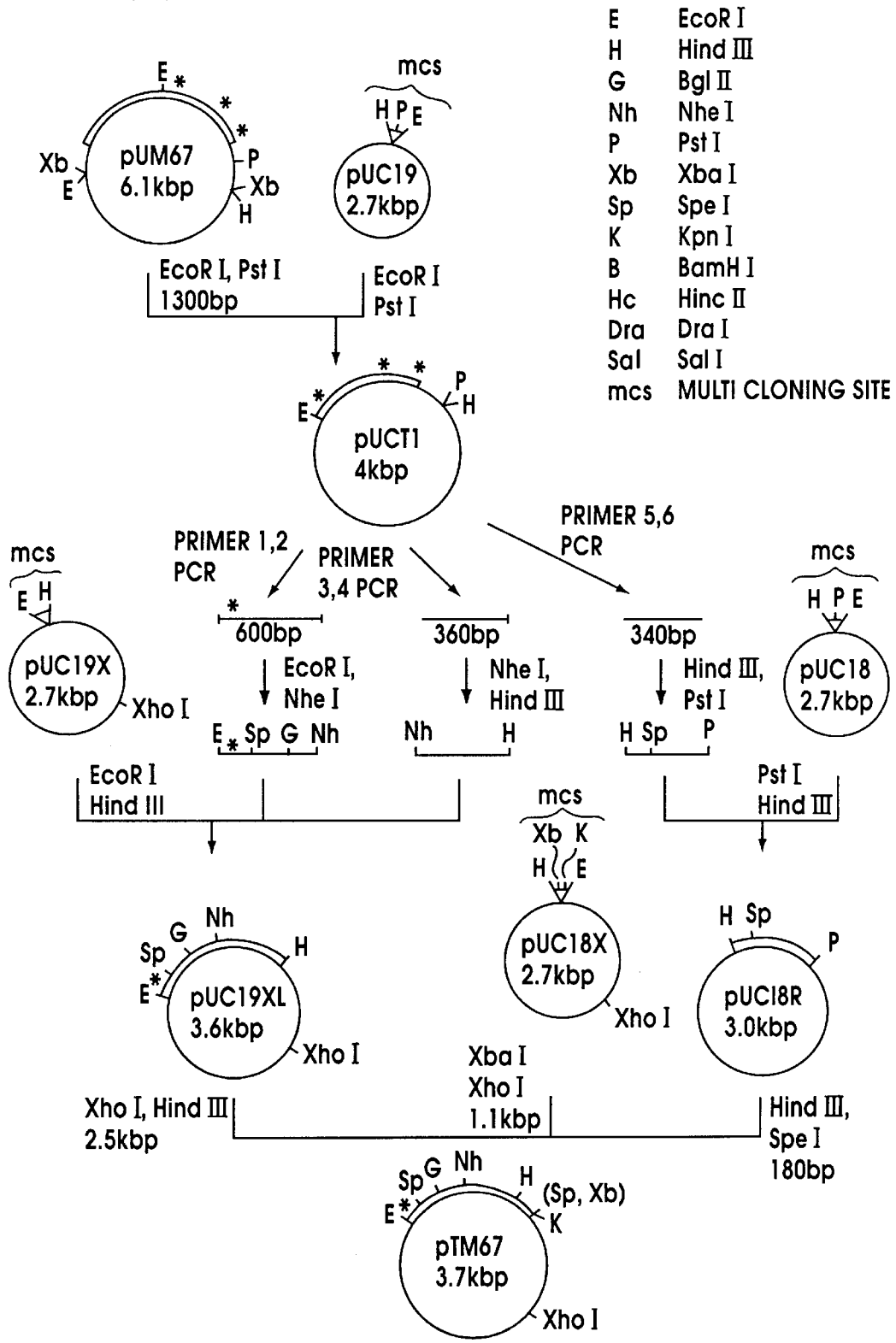
FIG. 9(A) and (B) show the procedure for constructing pHZ7929-67.
Figure 9B:
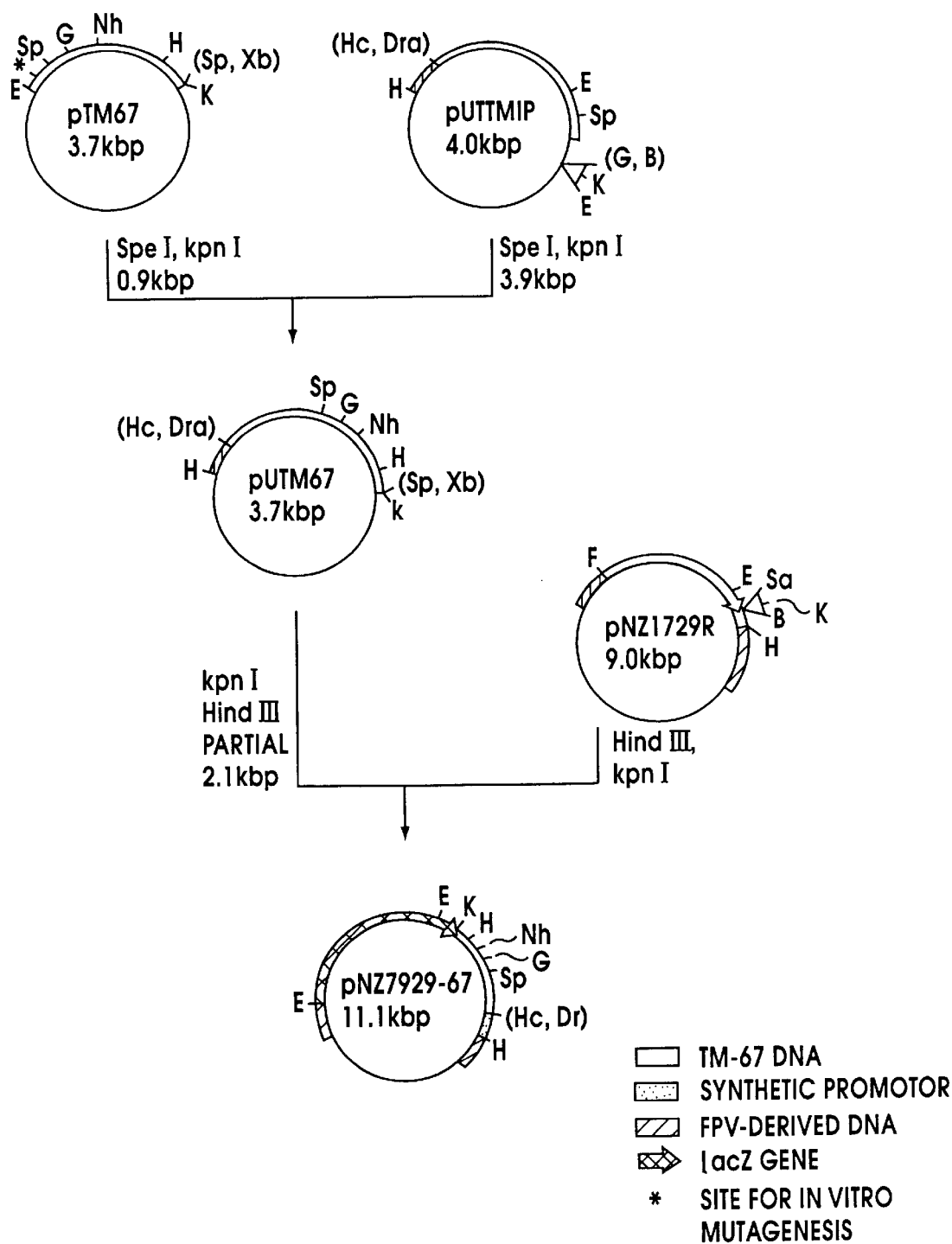

(4) Construction of pNZ7929-67 (FIG. 9 (B))

After pUTTM1P obtained in Example 1 (1) was digested with SpeI and KpnI, the digestion product was subjected to agarose gel electrophoresis to recover the fragment of 3.9 kbp. In a similar manner, after pTM67 was digested with SpeI and KpnI, the digestion product was subjected to agarose gel electrophoresis to recover the fragment of 0.9 kbp. The thus recovered fragment was ligated with the 3.9 kbp fragment described above using ligase. The resulting plasmid pUTM67 (4.8 kbp) was recovered. After this pUTM67 was digested with KpnI, the digestion product was partially digested with HindIII. The product was then subjected to agarose gel electrophoresis to recover the fragment of 2.1 kbp. The thus recovered fragment was ligated with the 9.0 kbp fragment obtained by digestion of PNZ1729R (cf. Reference Example 2) with HindIII and KpnI, using ligase. The resulting plasmid pNZ7929-67 (11.1 kbp) was recovered.

(5) Construction of recombinant Avipox virus fNZ7929-67 and purification

The procedures similar to Example 1 (3) were repeated using pNZ7929-67 obtained in (4) described above to obtain fNZ7929-67.

Example 7

Collection of recombinant Avipox virus fNZ7929-66 bearing TM-66

(1) Genomic Southern hybridization of *Mycoplasma gallisepticum* using TM-66 gene as a probe After 1 μg of the *Mycoplasma gallisepticum* DNA obtained in Reference Example (1) was digested with XbaI, the digestion product was subjected to 0.6% low melting agarose gel electrophoresis. After the electrophoresis, the gel was immersed in an alkaline denaturation solution (0.5M NaOH, 1.5M NaCl) for 10 minutes to denature DNA. The gel was then immersed in a neutralization solution (3M sodium acetate, pH 5.5) for 10 minutes for neutralization and then transferred onto a nylon membrane in 6-fold SSC solution (0.7M NaCl, 0.07M sodium citrate, pH 7.5). After air-drying, the nylon membrane was baked at 8.0° C. for 2 hours and 4-fold SET (0.6M NaCl, 0.08M Tris-HCl, 4 mM EDTA, pH 7.8)-10-fold Denhardt-0.1% SDS-0.1% Na$_4$P$_2$O$_7$-50 μg/ml of denatured salmon sperm DNA and pUM-1 (cf. Japanese Patent Application Laid-Open No. 2-111795) labelled in a conventional manner was added thereto to perform hybridization at 68° C. for 14 hours. The nylon membrane was overlaid on an X ray film. It was confirmed by autoradiography that hybridization occurred to the about 6.3 kbp fragment.

(2) Cloning of the XbaI-digested fragment of about 6.3 kbp to pUC-19 and analysis of the sequence After 4 μg of the *Mycoplasma gallisepticum* DNA obtained in Reference Example 1 (1) was digested with restriction enzyme XbaI, the digestion product was subjected to 0.6% low melting agarose gel electro-phoresis to recover the fragment of about 6.3 kbp confirmed in Example 7 (1) described above. The fragment was ligated with pUC-19 cleaved by digestion with XbaI using ligase. Competent *Escherichia coli* TG1 strain was transformed with the ligation product. The transformants were cultured at 37° C. for 15 hours in LB agar medium supplemented with 0.003% of 5-bromo-4-chloro-3-indolyl-β-D-galactopyranoside, 0.03 mM of isopropylthio-β-D-galactopyranoside and 40 μg/ml of ampicillin. White colonies grown on the medium were transferred to a nylon membrane and hybridization was carried out in a manner similar to (1) described above. Autoradiography reveals that cloning was effected and this plasmid was named pUM66 (about 9 kbp).

The about 6.3 kbp fragment inserted into pUM66 was analyzed by the dideoxy method by Sanger et al.

The restriction enzyme map of ORF present in this fragment is shown in FIG. 10 and the nucleotide sequence of this ORF and the amino acid sequence deduced therefrom are shown by SEQ ID NO: 7.

The polypeptide deduced from this ORF was named TM-66 polypeptide.

Figure 11A:
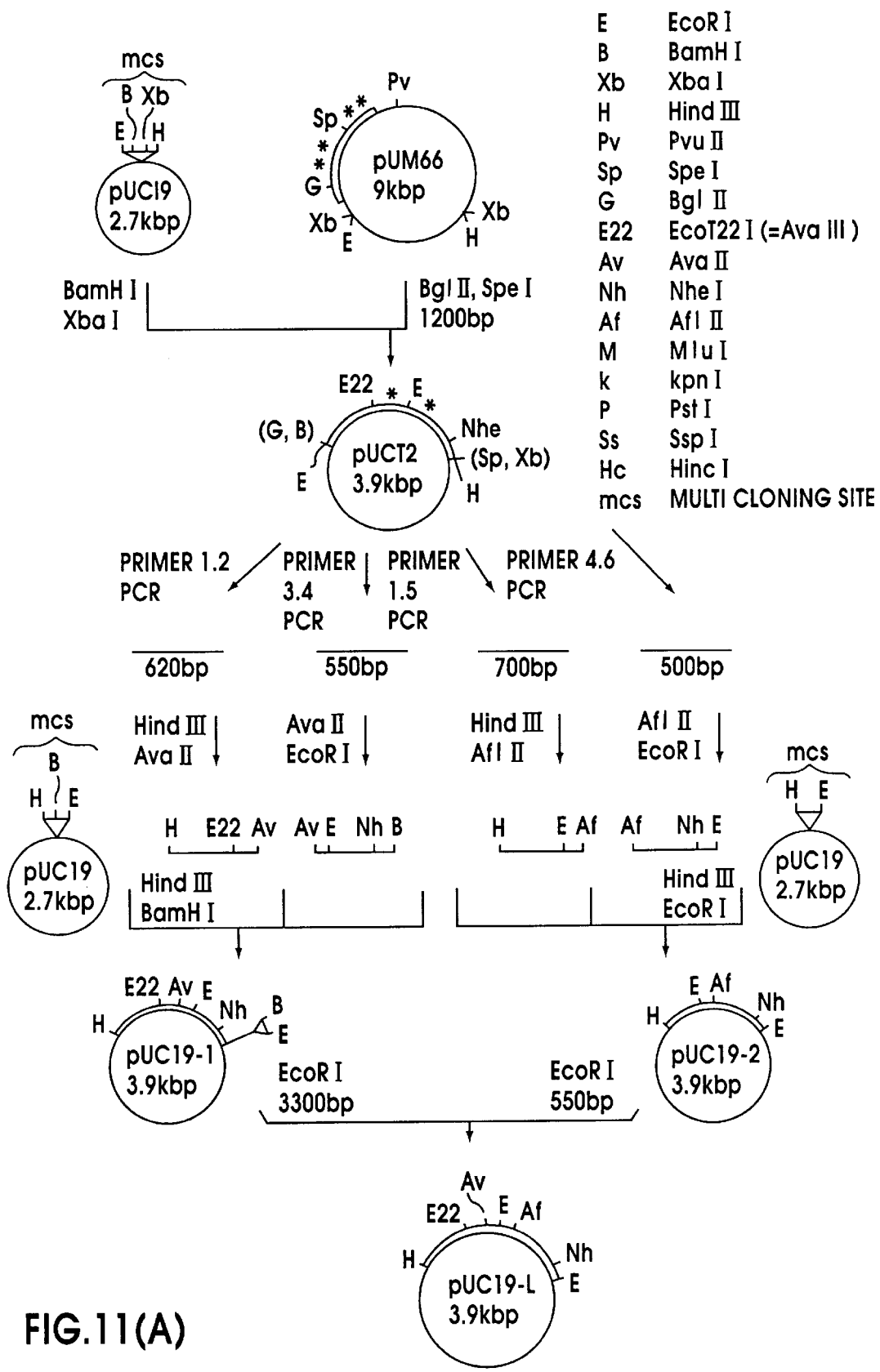
FIG. 11(A), 11(B) and 11(C) show the procedure for constructing pTM66.
Figure 11B:
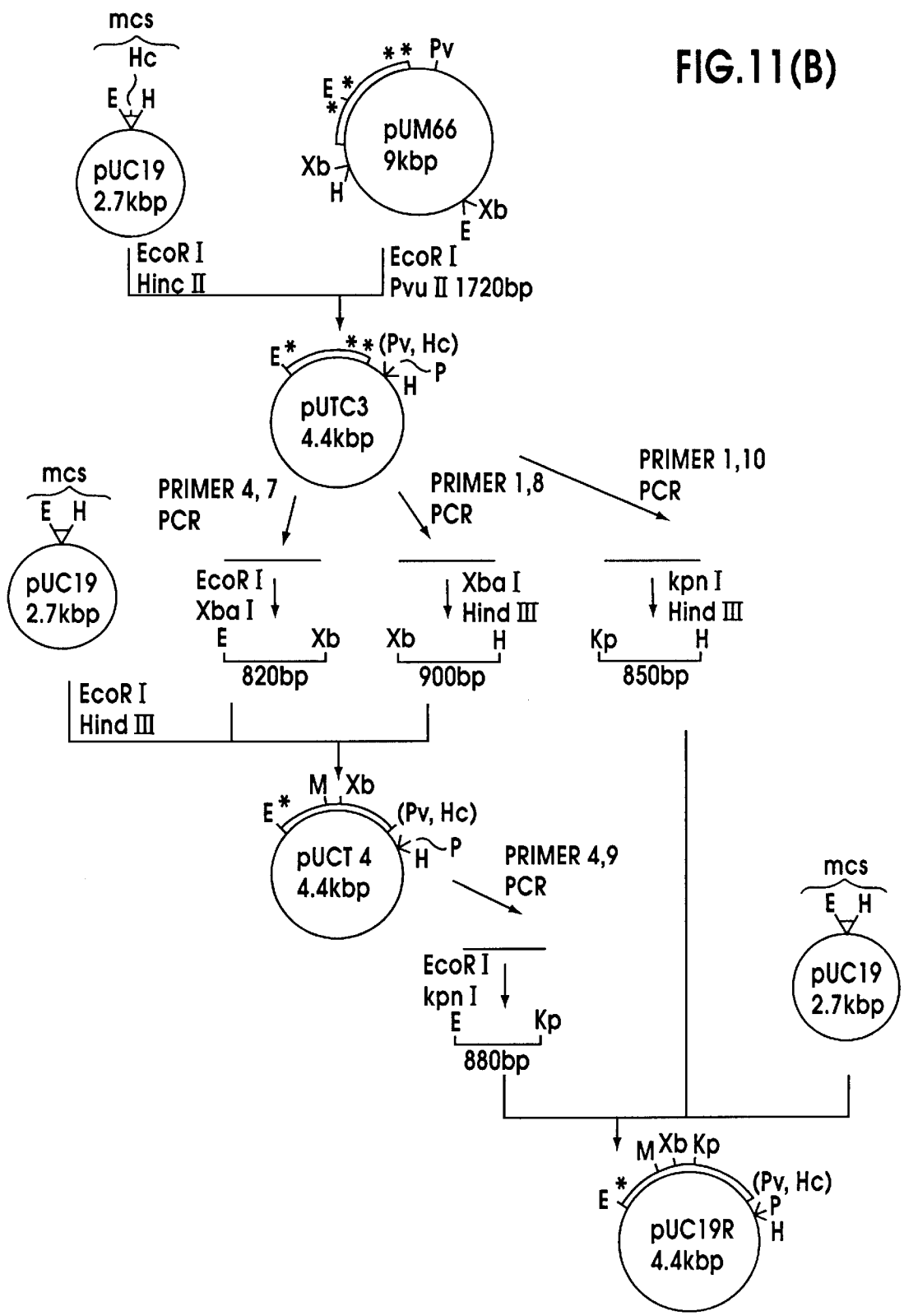
Figure 11C:
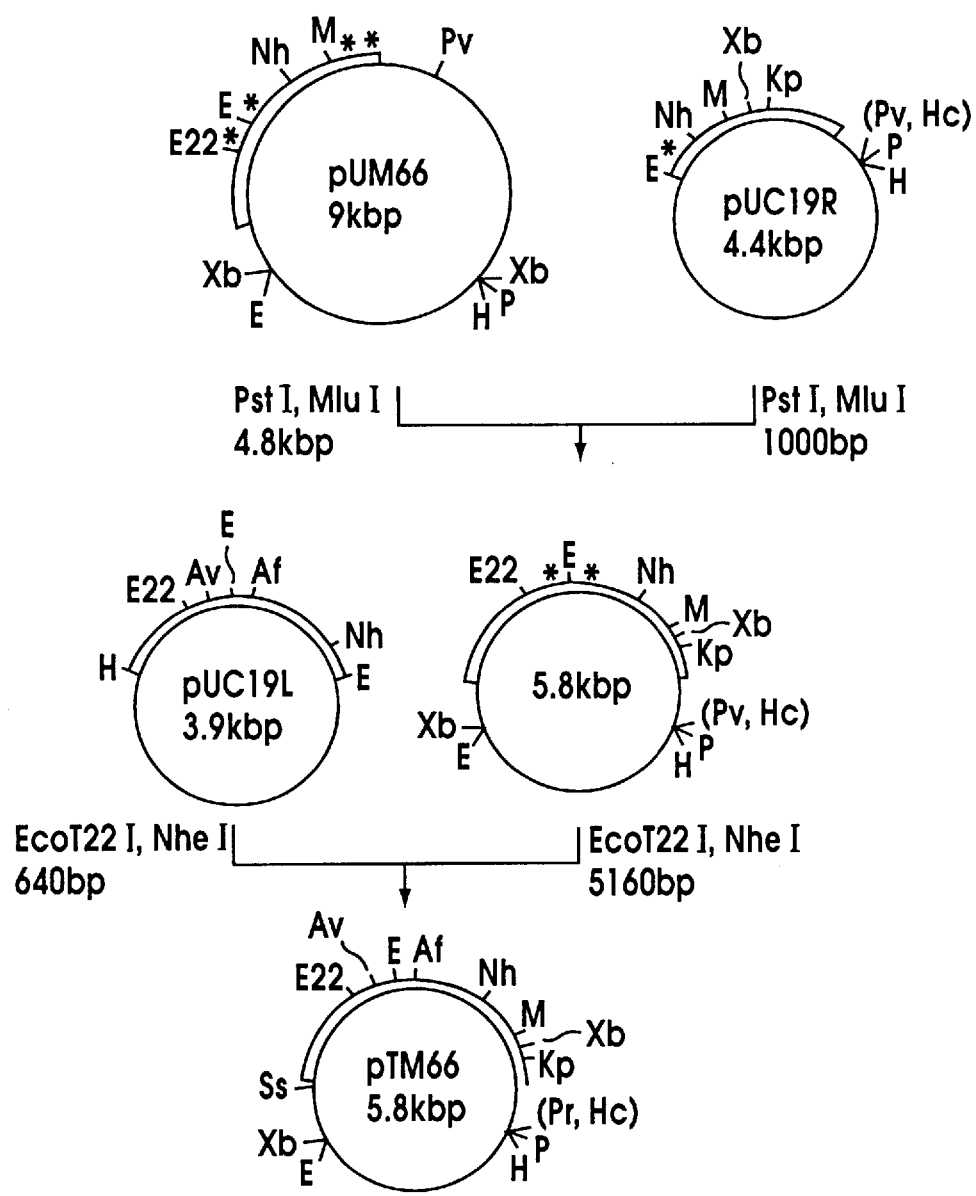

(3) Construction of pTM66 modified (TGA→TGG) not to read TGA in ORF encoding TM-66 as translation termination codon (see FIGS. 10 and 11 (A) through (C))

In order to modify the TGA codon in ORF of TM-66 to TGG codon, the change was made using polymerase chain reaction (PCR: Science, 230, 1350, 1354 (1985)) as in TM-67. DNA primers for PCR synthesized for the change are shown by SEQ ID NOS: 40–49.

Primers 1 to 10 corresponding to SEQ ID NOS: 40–49 using PCR are as follows.

```
Primer-1   5'-CAGGAAACAGCTATGAC-3'   (M13 RV primer)
Primer-2   3'-GTTCTTCCTGGCAAACTTTA-5'
                       AvaII
Primer-3   5'-AAGAAGGACCGTTTGGAATG-3'
                       AvaII
Primer-4   5'-GTTTTCCCAGTCACGAC-3'   (M13 primer)
Primer-5   3'-CAAAGTACCTAAATATCGAATTCACCT-5'
                                AflIII
Primer-6   5'-ATAGCTTAAGTGGAACAAACACG-3'
                  AflIII
Primer-7   3'-GGAACCAGATCTTGTTTCCC-5'
                      XbaI
Primer-8   5'-GGTCTAGAACAAAGGGATTGGACA-3'
               XbaI
Primer-9   3'-CTACCTACCATGGTGATGAT-5'
                      KpnI
Primer-10  5'-GATGGTACCACTACTATTTCATGGACA-3'
                  KpnI
``` pUM66 was digested with BglII and SpeI and the fragment of about 1.2 kbp was recovered from 0.5% low melting agarose. The 1.2 kbp fragment was ligated with the digestion product of pUC19 with BamHI and XbaI to obtain pUCT2 (3.9 kbp). Next, using pUCT2 as a template and using Primer-1 and Primer-2, the fragment of 620 bp was amplified following conventional procedures for PCR and then recovered; after amplification of the fragment of about 550 bp using Primer-3 and Primer-4, the amplified fragment was recovered. Furthermore, the fragment of about 620 bp was digested with HindIII and AvaII; the fragment of 550 bp was digested with AvaII and BamHI. These fragments were ligated with the digestion product of pUC19 with HindIII and BamHI by ligase, respectively. The resulting plasmid was extracted and named pUC19-1 (3.9 kbp).

Next, using pUCT2 as a template and using Primer-4 and Primer-6, the fragment of about 500 bp was amplified following conventional procedures for PCR and then recovered; after amplification of the fragment of about 700 bp using Primer-1 and Primer-5, the amplified fragment was recovered. Furthermore, the fragment of about 500 bp was digested with AflII and EcoRI; the fragment of about 700 bp was digested with HindIII and AflII. These fragments were ligated with the digestion product of pUC19 with HindIII and AflII by ligase. The resulting plasmid was extracted and named pUC19-2 (about 3.9 kbp). Furthermore, pUC19-1 was digested with EcoRI and the digestion product was subjected to 0.6% low melting agarose gel electrophoresis to recover the fragment of about 3.3 kbp. pUC19-2 was also digested with EcoRI and the digestion product was subjected to 2.0% low melting agarose gel electrophoresis to recover the fragment of about 550 bp. This fragment was ligated with the about 3.3 kbp fragment derived from pUC19-1 described above using ligase to obtain plasmid pUC19L bearing the fragment in which two TGA codons at the 5' end in ORF of TM-66 have been changed to TGG.

In order to change two TGA codons at the 3' end of ORF of TM66 to TGG, firstly pUM66 was digested with EcoRI and PvuII and the fragment of about 1720 bp was recovered from 0.6% low melting agarose gel. The recovered fragment was ligated with the digestion product of pUC19 with EcoRI and HincII to obtain plasmid pUCT3 (about 4.4 kbp). Using pUCT3 as a template and using Primer-4 and Primer-7, the fragment of about 820 bp was amplified following conventional procedures for PCR and also the fragment of about 900 bp using Primer-8 and Primer-1 was amplified likewise, and the both fragments were then recovered, respectively. After this 820 bp fragment was digested with EcoRI and XbaI, the digestion product was ligated with the aforesaid about 900 bp fragment obtained by digestion with XbaI and HindIII and the digestion product of pUC19 with HindIII and EcoRI, using ligase to obtain plasmid pUCT4 (about 4.4 kbp). Next, using pUCT-4 as a template and also using Primer-4 and Primer-9, the fragment of about 880 bp was amplified following conventional procedures for PCR and also the fragment of about 900 bp using pUCT3 as a primer and using Primer-1 and Primer-10 was amplified likewise following the conventional procedures for PCR; and the fragments were then recovered, respectively. After this 880 bp fragment was digested with EcoRI and KpnI, the digestion product was ligated with the aforesaid about 850 bp fragment obtained by digestion with HindIII and KpnI and the digestion product of pUC19 with EcoRI and HindIII, using ligase to obtain plasmid pUC19R.

In order to obtain plasmid in which TGA codons in ORF of TM-66 are all changed to TGG, pUM66 was digested with MluI and PvuII and the fragment of about 4.8 kbp was then recovered from 0.6% low melting agarose gel. The recovered fragment was ligated with the about 1.0 kbp fragment obtained by the digestion of pUC19R with MluI and PstI to obtain plasmid. This plasmid was further digested with EcoT22I and NheI. The resulting fragment of about 5.2 kbp was ligated with the fragment of about 640 bp obtained by the digestion of pUC19L with EcoT22I and NheI, using ligase to obtain plasmid bearing the full length of ORF in which TGA codons in ORF of TM-66 were all changed to TGG. This plasmid was named pTM66 (about 5.8 kbp).

Figure 12:
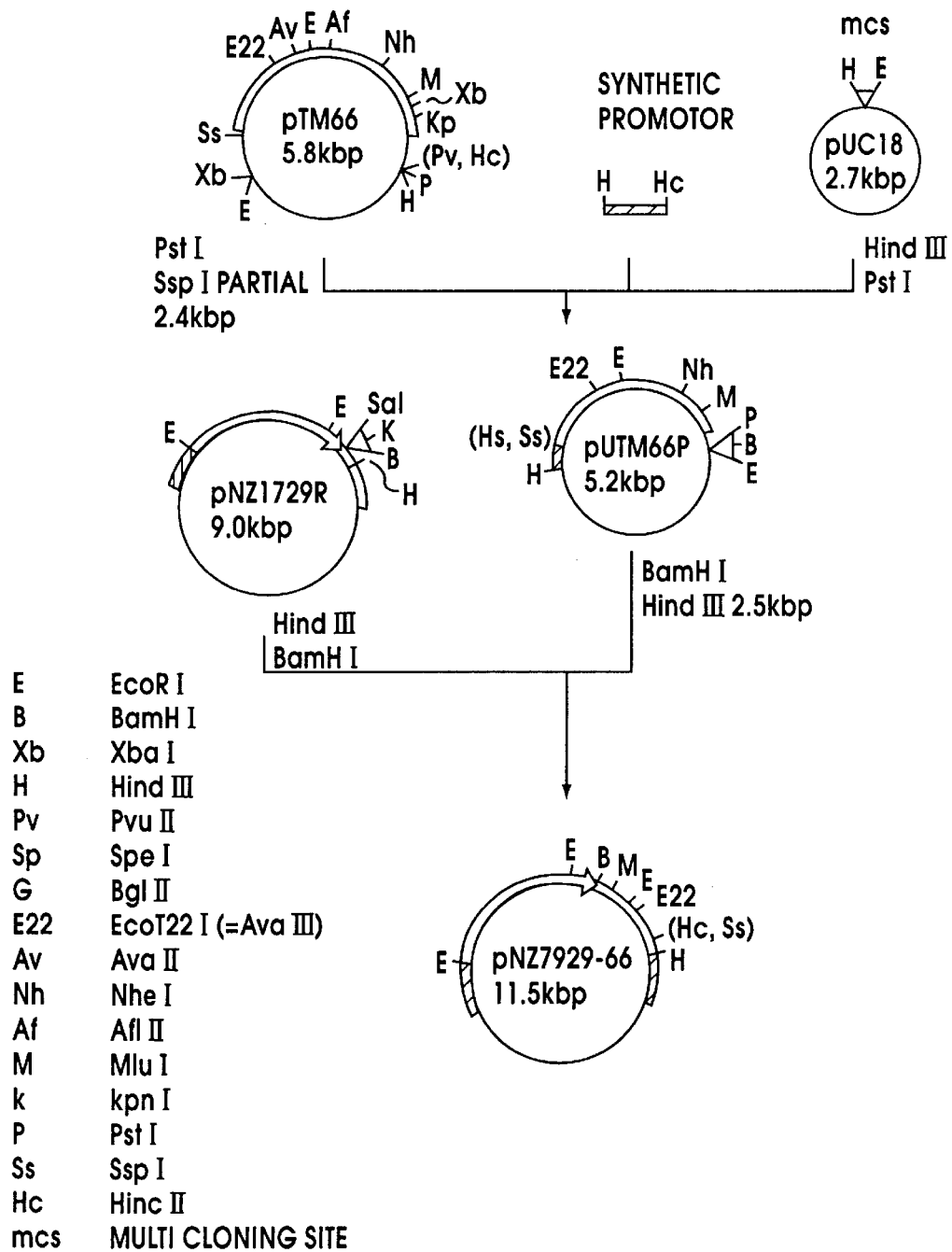
FIG. 12 shows the procedure for constructing pNZ7929-66.
Figure 13:
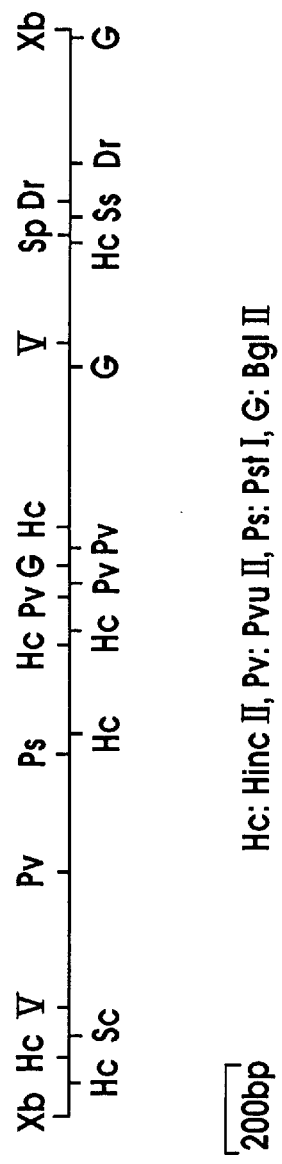
FIG. 13 shows a restriction enzyme map of DNA encoding the full length of TM-16 polypeptide.
Figure 14:
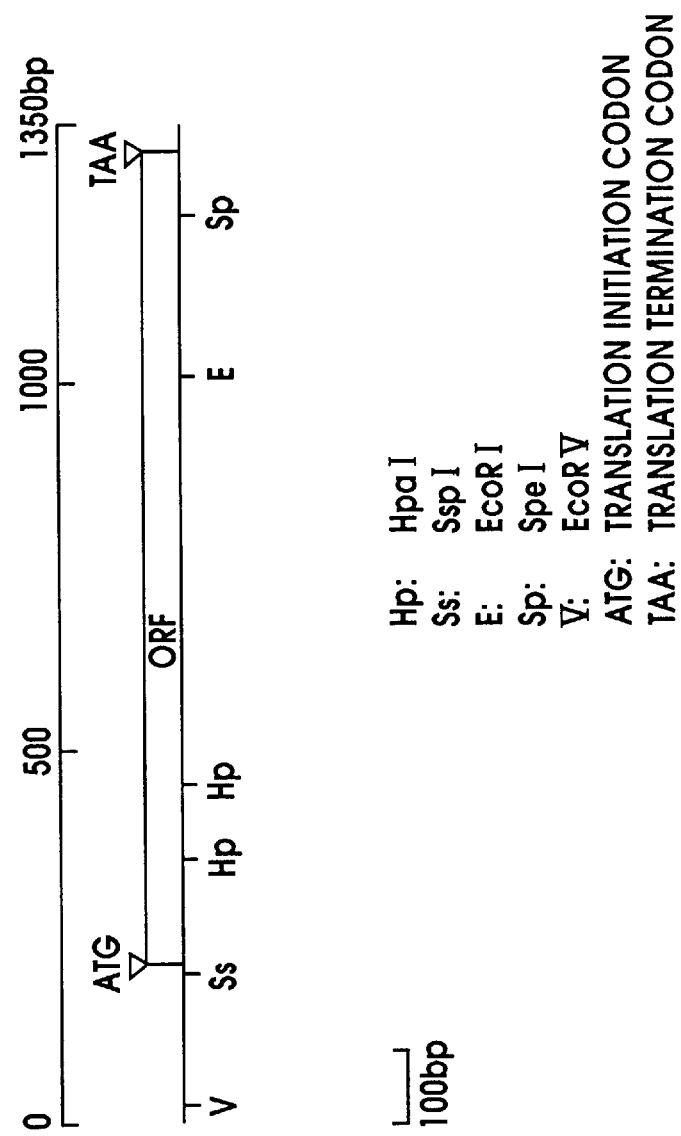
FIG. 14 shows a restriction enzyme map of the open reading frame of TM-16 polypeptide.

(4) Construction of pNZ7929–66 (FIG. 12)

After pTM66 was digested with PstI, the digestion product was partially digested with SspI to recover the fragment of about 2.4 kbp. Three of the about 2.4 kbp fragment, the fragment obtained by the digestion of the synthetic promoter in Reference Example with HindIII and HincII and the fragment obtained by the digestion of pUC18 with HindIII and PstI were ligated using ligase to obtain pUTM66P (about 5.2 kbp). Next, pUTM66P was digested with HindIII and BamHI and the digestion product was recovered from low melting agarose gel. This fragment (about 2.5 kbp) was ligated with the fragment obtained by the digestion of pNZ1729R with HindIII and BamHI, using ligase to obtain the desired plasmid pNZ7929-66 (about 11.5 kbp).

(5) Construction of fNZ7929-66 and purification

The procedures similar to Example 1 (3) were repeated using pNZ7929-66 obtained in (4) described above to obtain fNZ7929-66.

Example 8

Expression of TM-67 and TM-66 polypeptides in cells infected with fNZ7929-67 and fNZ7929-66

In order to examine that fNZ7929-67 and fNZ7929XM66 express the TM-67 and TM-66 polypeptides in infected cells, the immuno-fluorescence antibody method was carried out. fNZ7929-67 and fNZ7929-66 were infected to CEF, respectively and cultured at 37° C. until plaques appeared. Thereafter the medium was fixed with cold acetone. Using *Mycoplasma gallisepticum* S6-immunized chicken serum or *Mycoplasma gallisepticum-infected* chicken serum as a primary antibody, the medium was diluted to 100- to 1000-fold and the dilution was reacted. These culture cells were further reacted with fluorescence (FITC)-bound anti-chick immunoglobulin. After washing out the non-specific reaction portion, microscopic observation was made under fluorescence-excited wavelength. The reactivity is shown in Table 3.

TABLE 3

Reactivity of recombinant virus-infected CEF to various antisera

| Infected virus | Reactivity to primary antibody Infected | | |
|---|---|---|---|
| | anti-S6 | S6 | SPF |
| fNZ7929-67 | +++ | +++ | – |
| fNZ7929-66 | +++ | +++ | – |
| fNZ2929XM1 | ++ | ++ | – |
| NP | – | – | – |

+++: strongly reacted over the entire surface
++: strongly reacted
+: reacted
±: weakly reacted
–: not reacted The results reveal that fNZ7929-67, fNZ7929-66 and fNZ2929XM1 which are the recombinant viruses of the present invention were reactive with anti-S6 and S6 infection that are reactive with the infected cells alone.

Example 9

Activity of inhibiting the growth of an induced antibody of recombinant FPV-inoculated chick After fNZ7929-67 and fNZ7929-66 were cultured in CEF at 37° C. for 48 hours, the procedure of freezing and thawing was repeated twice to recover the cell suspension. The cell suspension was adjusted to have a virus titer of $10^6$ pfu/ml and then inoculated through a stab needle to SPF chicken (Line M, Nippon Seibutsu Kagaku Kenkyusho) of 7 days old at the right wing web in a dose of 10 μl. After the inoculation, generation of the pock was observed. Two weeks after the inoculation, sera were collected.

On the other hand, *Mycoplasma gallisepticum* S6 was inoculated on PPLO liquid medium (modified Chanock's medium) in a 10% concentration. After incubation at 37° C. for 3 days, the cell mass was removed through a membrane filter of 0.45 μm. The filtrate was diluted with PPLO liquid medium in a cell count of 103 CFU/ml and the resulting dilution was provided as the cell solution for determination of activity.

The cell solution was put in a polypropylene tube by 400 μl each and 100 μl each of standard chick serum, TMG-1 immunized serum (Japanese Patent Application Laid-Open No. 2-111795) and various sera were added thereto, respectively. By incubation at 37° C. for 2 to 5 days, growth inhibition test was conducted.

On Days 0, 1, 2, 3 and 4 after the incubation, 10 μl each was collected from the culture broth for *Mycoplasma gallisepticum* (hereinafter abbreviated as MG) growth inhibition test and spread over PPLO agar medium followed by incubation at 37° C. for 7 days. The corresponding cell count in the culture broth was deduced from the number of colonies appeared. The results of measuring the cell count on Day 3 are shown in Table 4.

TABLE 4

| Sample | Cell Count on Day 3 |
|---|---|
| SPF chicken sera | $1.3 \times 10^8$ |
| anti-TTMG-1 chicken sera | $1.8 \times 10^5$ |
| fNZ2929XMI-inoculated chicken sera | $4.5 \times 10^5$ |
| fNZ7929-67-inoculated chicken sera | $2.8 \times 10^4$ |
| fNZ7929-66-inoculated chicken sera | $3.2 \times 10^4$ |

In the culture broth of the medium in which SPF chick sera or equine sera were supplemented, there was no difference in growth rate of MG and the cell count reached saturation on Day 3 of the incubation. In the culture broth in which fNZ7929-67- or fNZ7929-66-inoculated sera were added, the growth of MG was more effectively inhibited than the case of fNZ2929XM1 or than the case of immunizing an antigen inducing an antibody for inhibiting the growth of MG as in anti-TTMG-1 chick sera. This fact indicates that TM67 polypeptide and TM66 polypeptide are antigens capable of inducing antibodies which can inhibit the growth of MG more effectively than in TTMG-1.

Example 10

Obtaining of polypeptide DNA TM-16 in which *Mycoplasma gallisepticum* is expressed (1) Preparation of *Mycoplasma gallisepticum* genomic DNA

*Mycoplasma gallisepticum* S6 strain was incubated at 37° C. for 3 to 5 days in liquid medium prepared by adding to 10 ml of PPLO broth basal medium 20% equine sera, 5% yeast extract, 1% glucose and a trace amount of Phenol Red as a pH indicator. As *Mycoplasma gallisepticum* grew, the pH of the culture medium decreased. At the time when the color of the pH indicator contained in the medium was changed from red to yellow, the incubation was terminated. After the culture medium was centrifuged at 8000G for 20 minutes, the cells were collected. The cells were suspended in PBS in a 1/10 volume of the medium. The suspension was again centrifuged at 10,000 rpm for 20 minutes and the cells were then collected. The collected cells were again suspended in 2.7 ml of PBS. After SDS was added to the suspension in a concentration of 1% and further 10 μg of RNase was added thereto, incubation was performed at 37° C. for 30 minutes for lysis.

The lysate was extracted 3 times with an equal volume of phenol and then 3 times with ethyl ether. By ethanol precipitation, 200 μg of *Mycoplasma gallisepticum* genomic DNA was obtained.

(2) Genomic Southern hybridization of *Mycoplasma gallisepticum* using M-16 DNA gene as a probe After 1 μg of the *Mycoplasma gallisepticum* DNA obtained in (1) described above was digested with XbaI, the digestion product was subjected to 0.6% low melting agarose gel electrophoresis. After the electrophoresis, the gel was immersed in an alkaline denaturation solution (0.5M NaOH, 1.5M NaCl) for 10 minutes to denature DNA. The gel was then immersed in a neutralization solution (3M sodium acetate, pH 5.5) for 10 minutes for neutralization and then transferred onto a nylon membrane in 6-fold SSC solution (0.7M NaCl, 0.07M sodium citrate, pH 7.5). After air-drying, the nylon membrane was baked at 80° C. for 2 hours and 4-fold SET (0.6M NaCl, 0.08M Tris-HCl, 4 mM EDTA, pH 7.8)-10-fold Denhardt-0.1% SDS-0.1% $Na_4P_2O_7$-50 μg/ml of denatured salmon sperm DNA and pUM-16 (M-16 gene is contained in this plasmid; cf. Japanese Patent Application Laid-Open No. 2-111795) labelled in a conventional manner was added thereto to perform hybridization at 68° C. for 14 hours. The nylon membrane was overlaid on an X ray film. It was confirmed by autoradiography that hybridization occurred to the about 5.5 kbp fragment.

(3) Cloning of XbaI-digested fragment of about 5.5 kbp to pUC-19 and colony hybridization After 4 μg of the *Mycoplasma gallisepticum* DNA obtained in (1) described above was digested with XbaI, the digestion product was subjected to 0.6% low melting agarose gel electrophoresis to recover the fragment of about 5.5 kbp. The fragment was ligated with the digestion product of pUC-19 with XbaI using ligase. Competent *Escherichia coli* TG1 strain was transformed with the ligation product. The transformants were cultured at 37° C. for 15 hours in LB agar medium supplemented with 0.003% of 5-bromo-4-chloro-3-indolyl-β-D-galactopyranoside, 0.03 mM of isopropylthio-β-D-galactopyranoside and 40 μg/ml of ampicillin. White colonies grown on the medium were transferred onto a nylon membrane and hybridization was carried out in a manner similar to (2) described above. It was confirmed by autoradiography that cloning was effected and this plasmid was named pUM16.

(8) Sequence analysis of pUM-16 insert DNA

The sequence of about 5.5 kbp fragment inserted into pUM-16 prepared in (3) described above was analyzed by the dideoxy method by Sanger et al. (Proc. Natl. Acad. Sci. USA, 74, 5463 (1977)).

The restriction enzyme map of this fragment is shown in FIG. 13. The restriction enzyme map of the open reading frame present in this fragment is also shown in FIG. 14 and the nucleotide sequence of this ORF and the amino acid sequence deduced therefrom are shown by SEQ ID NOS: 5–6. The polypeptide deduced from this ORF was named TM-16 polypeptide.

Hereinafter the sequences employed in the present invention are described as sequence listing. The sequences used for the primers are described basically from the 3' end. However, the primers depicted from the 5' end in the body of the specification are described from the 5' end to conform to the description.

We claim:

1. A recombinant Avipox virus comprising DNA encoding a polypeptide of *Mycoplasma gallisepticum*, wherein said DNA encoding a polypeptide of *Mycoplasma gallisepticum* comprises SEQ ID NO:1, SEQ ID NO:3, SEQ ID NO:5, SEQ ID NO:7, or SEQ ID NO:9, or a degenerate sequence thereof.

2. The recombinant Avipox virus according to claim 1, wherein DNA of a virus that infects poultry encoding a signal membrane anchor of type II expernal membrane protein is inserted at the terminus of the DNA encoding a polypeptide of *Mycoplasma gallisepticum*.

3. The recombinant Avipox virus according to any one of claims 1 and 2 wherein said inserted DNA encoding a polypeptide of *Mycoplasmna gallisepticum comprises SEQ ID NO:*1, SEQ ID NO:5, SEQ ID NO:7, or SEQ ID NO:9.

4. The recombinant Avipox virus according to any one of claims 1 and 2, wherein said DNA encoding a polylpeptide of *Mycoplasma gallisepticum* comprises SEQ ID NO:5, or a degenerate nucleotide sequence thereof.

5. A live vaccine for poultry *Mycoplasma gallisepticum* infection comnprising a recombinant Avipox virus according to any one of claims 1, 2, 3, and 4.

6. A substantially pure antigenic protein which is reactive with *Mycoplasma gallisepticum*-inmumiized sera or *Mycoplasma gallispeticum*-infected sera and encoded by a gene derived from *Mycoplasma gallisepticum* comprising the nucleotide sequence of SEQ ID NO;1 ol a degenerate sequence thereto.

7. An isolated DNA encoding an anitigenic protein according to claim 6.

8. A substantially pure antigenic protein which is reactive with *Mycoplasma gallisepticum*-immunized sera or *Mycoplasma gallispeticum*-infected sera and encoded by a gene derived from *Mycoplasma gallisepticum* comprising the nucleotide sequence of SEQ ID NO:9 or a degenerate sequence thereto.

9. An isolated DNA encoding an antigenic protein according to claim 8.

10. A substantially pure antigenic protein which is reactive with *Mycoplasma gallisepticum*-imrunied sera or *Mycoplasma gallispeticum*-infected sera and encoded by a gene derived from *Mycoplasma gallisepticum* comprising the nucleotide sequence of SEQ ID NO:7 or a degenerate sequence thereto.

11. An isolated DNA encoding an antigenic protein according to claim 10.

12. A fused protein comprising a polypeptide of *Mycoplasma gallisepticum* ligated at the 5' end thereof with a signal membrane anchor of type II external membrane protein of a virus that infects poultry, wherein said polypeptide of *Mycoplasma gallisepticum* is encoded by DNA comprising SEQ ID NO:1, SEQ ID NO:3, SEQ ID NO:5, SEQ ID NO:7, or SEQ ID NO:9, or a degenerate sequence thereof, and the signal membrane anchor is encoded by DNA comprising SEQ ID NO:22 or a degenerate sequence thereof.

13. A hybrid DNA encoding the fused protein according to claim 12.

14. A component vaccine comprising a protein according to claim 6, 8, 10, or 12.

15. A recombinant Avipox virus comprising DNA encoding a polypeptide of *Mycoplasma gallisepticum*, wherein said DNA encoding a polypeptide of *Mycoplasma gallisepticum* comprises SEQ ID NO;3, SEQ ID NO:7, or SEQ ID NO:9, or a degenerate sequence thereof.

16. The recombinant Avipox virus according to claim 15, wherein DNA of a virus that infects poultry encoding a signal membrane anchor of type II external membrane protein is inserted at the terminus of the DNA encoding a polypeptide of *Mycoplasma gallisepticum*.

17. A live vaccine for poultry *Mycoplasma gallisepticum* infection comprising a live recombinant Avipox vinrs according to claim 16.

18. A live vaccine for poultry *Mycoplasma gallisepticum* infection comprising a live recombinant Avipox virus according to claim 16.

19. A substantially pure antigenic protein which is reactive with *Mycoplasma gallisepticum*-immunized sera or *Mycoplasma gallisepticum*-infected sera and encoded by a gene derived from *Mycoplasma gallisepticum* comprising the nucleotide sequence of SEQ ID NO:5 or a degenerate sequence thereof.

20. An isolated DNA encoding an antigenic protein according to claim 19.

21. A fused protein according to claim 12, wherein a hydrophilic sequence having between 10 and 50 amino acids is present at the carboxy terminal of the signal membrane anchor.

* * * * *